(12) United States Patent
Kondo et al.

(10) Patent No.: US 6,610,514 B2
(45) Date of Patent: *Aug. 26, 2003

(54) YEAST VECTOR AND METHOD OF PRODUCING PROTEINS USING THE SAME

(75) Inventors: Keiji Kondo, Yokohama (JP); Yutaka Miura, Yokohama (JP)

(73) Assignee: Kirin Beer Kabushiki Kaisha, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 09/908,855

(22) Filed: Jul. 20, 2001

(65) Prior Publication Data

US 2002/0115220 A1 Aug. 22, 2002

Related U.S. Application Data

(62) Division of application No. 09/242,690, filed as application No. PCT/JP97/02924 on Aug. 22, 1997, now Pat. No. 6,284,536.

(30) Foreign Application Priority Data

Aug. 23, 1996 (JP) ............................................... 8-241062

(51) Int. Cl.$^7$ ........................... C12P 21/02; C12N 1/19; C12N 15/63; C12N 15/81
(52) U.S. Cl. ............................... 435/69.1; 435/254.22; 435/320.1; 435/471; 435/483
(58) Field of Search ............................ 435/69.1, 320.1, 435/471, 483, 254.22

(56) References Cited

U.S. PATENT DOCUMENTS 5,849,524 A 12/1998 Kondo et al.
6,284,534 B1 * 9/2001 Kondo et al. ............. 435/320.1

FOREIGN PATENT DOCUMENTS

JP 5-70494 A 3/1993
WO 83/03259 9/1983

OTHER PUBLICATIONS

Lopes, T., et al., "High–Copy–Number Integration into the Ribosomal DNA of *Saccharonmyces cerevisiae*: A New Vector for High–Level Expression," *Gene*, vol. 79, pp. 199–206 (1989).
Bergkamp, R., et al., "Multiple–Copy Integration of the á–galactosidase Gene from *Cyamopis tetragonoloba* into the Ribosomal DNA of *Kluyveromyces lactis*," *Curr. Genet.*, vol. 21, pp. 365–370 (1992).

Le Dall, M., et al., "Multiple–Copy Integration in the Yeast *Yarrowia Lipolytica*," *Curr. Genet.*, vol. 26, pp. 38–44 (1994).

Lopes, T., et al., "Mechanism of High–Copy–Number Integration of pMIRY–type Vectors into the Ribosomal DNA of *Saccharomyces cerevisiae*," *Gene*, vol. 105 , pp. 83–90 (1991).

Lopes, T., et al., "Factors Affecting the Mitotic Stability of High–Coy–Number Integration into the Ribosomal DNA of *Saccharomyces cerevisiae*," *Yeast*, vol. 12, pp. 467–477 (1996).

Kobayashi, K., et al., "Gene Analysis of Trehalose–Producing Enzymes from Hypertherophilic Archaea in Sulfolobales," *Biosci. Biotech. Biochem.*, vol. 60, No. 10, pp. 1720–1723 (1996).

Woudt, L., et al., "Structural and Putative Regulatory Sequences of the Gene Encoding RIbosomal Protein L25 in *Candida utilis*," *Curr. Genet.*, vol. 12, pp. 193–198 (1987).

Kondo, K., et al., "High–Level Expression of a Sweet Protein, Monellin, in the Food Yeast *Candida utilis*," *Nature Biotechnology*, vol. 15, No. 5, pp. 453–457 (1987).

Kondo, K., et al., "A Transformation System for the Yeast *Candida utilis*: Use of a Modified Endogenous Ribosomal Protein Gene as a Drug–Resistant Marker and Ribosomal DNA as an Integration Target for Vector DNA," *Journal of Bacteriology*, vol. 177, No. 24, pp. 7171–7177 (1995).

* cited by examiner

*Primary Examiner*—Terry McKelvey
(74) *Attorney, Agent, or Firm*—Foley & Lardner

(57) ABSTRACT

An object of the present invention is to provide a vector which can be integrated into a yeast chromosome in a high number of copies. Another object of the present invention is to provide a modified vector which can be integrated into the yeast chromosome in a high number of copies and of which expression units stably maintain on the chromosome. The vector according to the present invention comprises a marker gene for selecting transformants, a shortened promoter sequence which is operably linked to the marker gene and a sequence homologous to the chromosomal DNA of *Candida utilis*, and optionally a heterologous gene or a gene derived from *C. utilis*, wherein the vector is linearized by cleaving within said homologous DNA sequence or at both ends of the homologous DNA sequence with restriction enzymes, and wherein the heterologous gene or the gene derived from *C. utilis* can be integrated into the chromosomal DNA of *C. utilis* by homologous recombination.

43 Claims, 29 Drawing Sheets

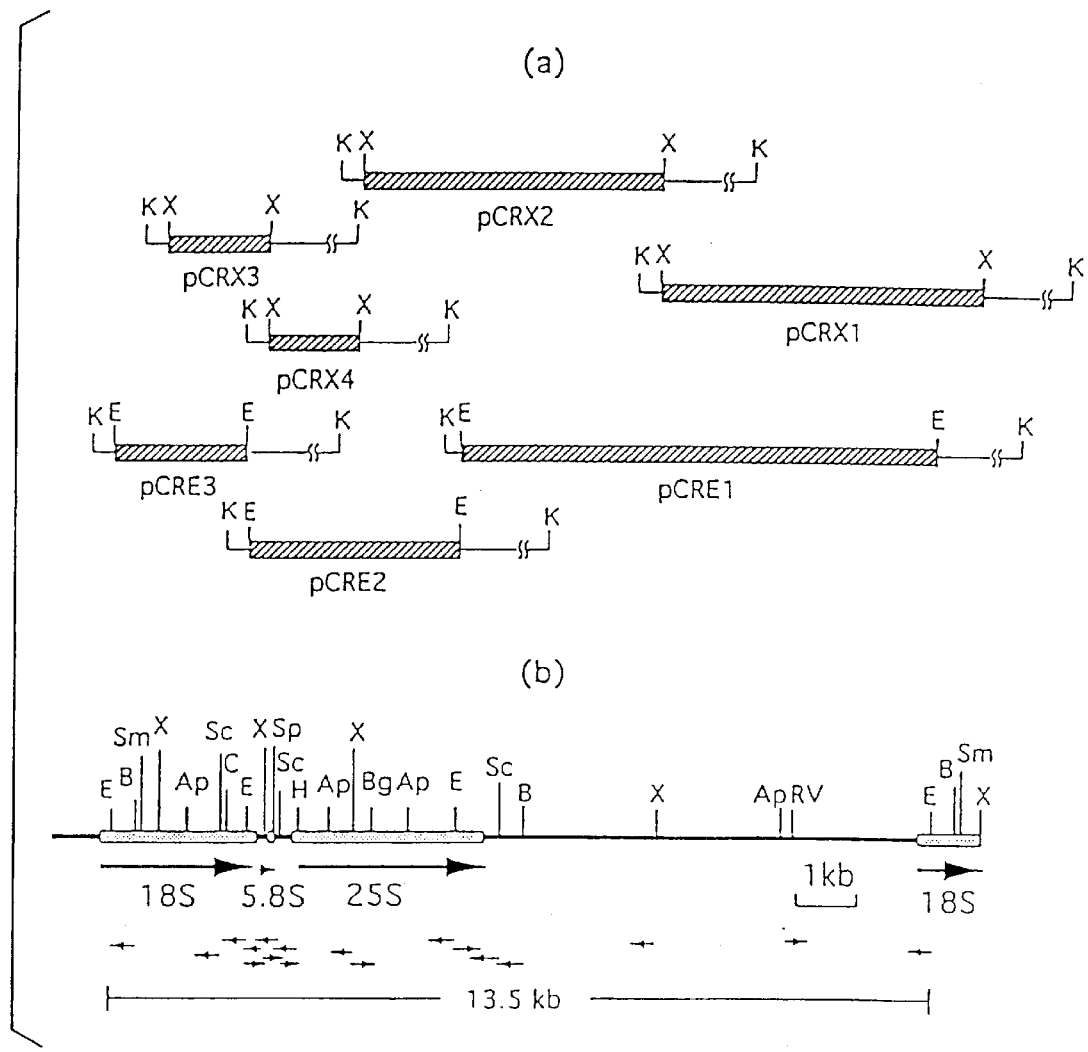
F I G. 2

```
   1 AAGCTTATGG AGGAGATTGG GAAGATTGAA CGAGGTGAGA TGGACACGTT GCTGATTGAC
  61 GAGATCGGCA AGAAGGAGGC ACCTGTGGTG AAACCACTTA CACCCGACGT GGATAGTAAT
 121 GTAACAGGGG AACCGACTGG ACATAGTTCT ACGACACCAC CACCGGTGGA ACAGGACTCG
 181 AGCACAACCA CGAGGAAGAG AGCACAAGAC GATGGTGAGG AAAACACAAG GAAGAAGCCC
 241 AAGGTTGAGG CAGAGAAAAA GGCAGAGCAA GAGGCAGAGA AAGAGGCAGA GAAAGAGGCA
 301 GAGAAAGAGG CAGAGCAAGA GGCAGAGAAA GAGGCTCCGC GTGCAGTGCC GAACAAGAGA
 361 CTACAACACA TTGCTACTCC TCTCATCGAG AGCATCTCGT CATACAAGTA CGCCTCAGCG
 421 TTTCTACACC CTGTTAACGA GTCCAGTGCA CCCAACTATT ACTCTCTGAT CAAGAAACCA
 481 AGGGATCTGA AGACCATCAA ACAGATGGTC AAGGACGGAC GTATACAGAC CAATCTTGAG
 541 CTGGAGAGGG AGATCTTGCT GATGTTTGCC AATGCCATCA TGTACAACAA GACCGGGACG
 601 GATATCTACG AGTGGACCAA GGAGATGCAG CCGGAAGTTG ACAAGCTCAT CGAGCTGTTT
 661 AACGAGAGTA AATAGGATAC AGGCTAGAGA TCAAAAGAAG AATAGAAACA GCTCGATAAA
 721 ACGGTATTGT AAGTGGTATG TACAAAGGGG TGTGTCTTGC TCAACGTCTT TGCATCTGCT
 781 GAGTCAAAGC AGCGTTCTGC TCTTGGAATC TAAGACCGAC TCTTTCCGAA TGCTTGAGGA
 841 ACTTTTCAGA GCACTTCAAC ACACAGGATT CCTCCTTTGA TGATAGCTTT TCAGAGGTGA
 901 AGTCGTTGAC ACAGTCGCTG AAACAACGCT CAACGAGGTT GGAATAAAGA CGCATAAAGT
 961 CCTTCATCTG CTTCTGCTCA ACAAGCTGCT GGAACTGCTG CTGCTCTTTT GGGTTCAATT
1021 GGTCCATCCT TGCTACTTTT CCGCCTAGTT TCGATTCCGA TTCTGATAGA GAAGCCCAGC
1081 TATGAATGGA AGAAATTTTT CACTTTTGTA TGTCCTTTTT TTCACGCTTC GTTGCTTCGG
1141 ACAAAAAAAT AGTGGAGGCA CTCGGTGGAG GGAAGCTATC CTCGAGATGA AAAATTTCAA
1201 GCTCATCTCA TCGTCCAAGT GGGACAGCAA GCTGAGGCTT CTGAAGAGGT TGAGGAAAAT
1261 GGTCACCACG TTATCGTACA CAGAGAGGGC ATCGCAGCAC CCTTCGCCAC TTGCTAAGCG
1321 TCTGTTTTCG CTTATGGAGT CCAAGAAGAC GAACCTGTGT GCCAGTGTCG ATGTTCGTAC
1381 CACAGAGGAG TTGCTCAAGC TCGTTGATAC GCTTGGTCCT TATATCTGTC TGTTGAAGAC
1441 GCATATTGAT ATCATTGATG ACTTCTCTAT GGAGTCTACT GTGGCTCCAC TGTTGGAGCT
1501 TTCAAAGAAG CACAATTTCC TCATCTTTGA GGACCGTAAG TTTGCTGATA TCGGCAACAC
1561 CGTCAAGGCA CAGTACGCCG GTGGTGCGTT CAAGATTGCG CAATGGGCAG ATATCACCAA
1621 CGCCCACGGT GTCACCGGTG CAGGTATCGT CAAGGGGTTG AAGGAGGCTG CACAGGAAAC
1681 CACGGATGAG CCAAGAGGGC TGTTGATGCT TGCGGAGCTG AGCTCCAAGG GCTCCTTGGC
1741 CCACGGGACA TATACCGAGG AGACCGTGGA GATTGCCAAA ACTGATAAGG ACTTTTGTAT
1801 TGGATTCATC GCACAGAGAG ACATGGGTGG CAGAGAAGAT GGGTTCGACT GGATCATCAT
1861 GACACCAGGC GTGGGACTCG ACGATAAGGG CGACTCCCTG GCCAACAGT ACAGAACTGT
1921 CGATGAGGTT GTCAGTGGTG GCTCTGACAT CATCATCGTT GGTAGAGGCT TGTTTGGAAA
1981 GGGAAGAGAT CCAACAGTGG AAGGTGAGCG TTATAGAAAA GCAGGCTGGG ATGCTTATCT
2041 CAAGAGATGC TCAGCTCAAT AAGCGTTGAG CTCTGGCTTG TATAGGTTCA CTTGTATAAA
2101 ATGTTCATTA CTGTTTTCGG AAGTTGTAGA TTGCCATTTT TGCGCAAATT GACGCCAGTC
2161 TTTTTTTGCG CCAAATGTCA GTTTTTTGC GCCAAAATTT ACTTCATCTT ATACAACTGC
2221 AAAAACCATC CAATCCAATC CAGAAAGGAC TGATCAATGG TGGTGATTGA CTCAAGTTCT
2281 GATGCTACAC AACAGACAGA GCTCTCTAAA AAGAATTCGA TATCAAGCTT
```

FIG. 5

```
     1260        1270        1280        1290        1300
       *    *    *    *    *    *    *    *    *    *
     ATG GTC ACC ACG TTA TCG TAC ACA GAG AGG GCA TCG CAG CAC CCT TCG
     Met Val Thr Thr Leu Ser Tyr Thr Glu Arg Ala Ser Gln His Pro Ser
        1310         1320        1330        1340        1350
         *    *    *    *    *    *    *    *    *
     CCA CTT GCT AAG CGT CTG TTT TCG CTT ATG GAG TCC AAG AAG ACG AAC
     Pro Leu Ala Lys Arg Leu Phe Ser Leu Met Glu Ser Lys Lys Thr Asn
        1360         1370        1380        1390        1400
      *    *    *    *    *    *    *    *    *    *
     CTG TGT GCC AGT GTC GAT GTT CGT ACC ACA GAG GAG TTG CTC AAG CTC
     Leu Cys Ala Ser Val Asp Val Arg Thr Thr Glu Glu Leu Leu Lys Leu
          1410         1420        1430        1440        1450
       *    *    *    *    *    *    *    *    *    *
     GTT GAT ACG CTT GGT CCT TAT ATC TGT CTG TTG AAG ACG CAT ATT GAT
     Val Asp Thr Leu Gly Pro Tyr Ile Cys Leu Leu Lys Thr His Ile Asp
             1460         1470        1480         1490
        *    *    *    *    *    *    *    *    *
     ATC ATT GAT GAC TTC TCT ATG GAG TCT ACT GTG GCT CCA CTG TTG GAG
     Ile Ile Asp Asp Phe Ser Met Glu Ser Thr Val Ala Pro Leu Leu Glu
1500         1510        1520        1530        1540
    *    *    *    *    *    *    *    *    *    *
     CTT TCA AAG AAG CAC AAT TTC CTC ATC TTT GAG GAC CGT AAG TTT GCT
     Leu Ser Lys Lys His Asn Phe Leu Ile Phe Glu Asp Arg Lys Phe Ala
        1550         1560        1570        1580        1590
         *    *    *    *    *    *    *    *    *
     GAT ATC GGC AAC ACC GTC AAG GCA CAG TAC GCC GGT GGT GCG TTC AAG
     Asp Ile Gly Asn Thr Val Lys Ala Gln Tyr Ala Gly Gly Ala Phe Lys
        1600         1610        1620        1630        1640
      *    *    *    *    *    *    *    *    *    *
     ATT GCG CAA TGG GCA GAT ATC ACC AAC GCC CAC GGT GTC ACC GGT GCA
     Ile Ala Gln Trp Ala Asp Ile Thr Asn Ala His Gly Val Thr Gly Ala
          1650         1660        1670        1680        1690
       *    *    *    *    *    *    *    *    *    *
     GGT ATC GTC AAG GGG TTG AAG GAG GCT GCA CAG GAA ACC ACG GAT GAG
     Gly Ile Val Lys Gly Leu Lys Glu Ala Ala Gln Glu Thr Thr Asp Glu
             1700         1710        1720        1730
        *    *    *    *    *    *    *    *    *
     CCA AGA GGG CTG TTG ATG CTT GCG GAG CTG AGC TCC AAG GGC TCC TTG
     Pro Arg Gly Leu Leu Met Leu Ala Glu Leu Ser Ser Lys Gly Ser Leu
1740         1750        1760        1770        1780
    *    *    *    *    *    *    *    *    *    *
     GCC CAC GGG ACA TAT ACC GAG GAG ACC GTG GAG ATT GCC AAA ACT GAT
     Ala His Gly Thr Tyr Thr Glu Glu Thr Val Glu Ile Ala Lys Thr Asp
```

FIG. 6

```
        1790         1800         1810         1820          1830
   *     *     *     *     *     *     *     *     *
 AAG   GAC   TTT   TGT   ATT   GGA   TTC   ATC   GCA   CAG   AGA   GAC   ATG   GGT   GGC   AGA
 Lys   Asp   Phe   Cys   Ile   Gly   Phe   Ile   Ala   Gln   Arg   Asp   Met   Gly   Gly   Arg
       1840         1850         1860         1870          1880
   *     *     *     *     *     *     *     *     *     *
 GAA   GAT   GGG   TTC   GAC   TGG   ATC   ATC   ATG   ACA   CCA   GGC   GTG   GGA   CTC   GAC
 Glu   Asp   Gly   Phe   Asp   Trp   Ile   Ile   Met   Thr   Pro   Gly   Val   Gly   Leu   Asp
       1890         1900         1910         1920          1930
   *     *     *     *     *     *     *     *     *     *
 GAT   AAG   GGC   GAC   TCC   CTG   GGC   CAA   CAG   TAC   AGA   ACT   GTC   GAT   GAG   GTT
 Asp   Lys   Gly   Asp   Ser   Leu   Gly   Gln   Gln   Tyr   Arg   Thr   Val   Asp   Glu   Val
       1940         1950         1960         1970
   *     *     *     *     *     *     *     *     *
 GTC   AGT   GGT   GGC   TCT   GAC   ATC   ATC   ATC   GTT   GGT   AGA   GGC   TTG   TTT   GGA
 Val   Ser   Gly   Gly   Ser   Asp   Ile   Ile   Ile   Val   Gly   Arg   Gly   Leu   Phe   Gly
1980         1990         2000         2010          2020
   *     *     *     *     *     *     *     *     *     *
 AAG   GGA   AGA   GAT   CCA   ACA   GTG   GAA   GGT   GAG   CGT   TAT   AGA   AAA   GCA   GGC
 Lys   Gly   Arg   Asp   Pro   Thr   Val   Glu   Gly   Glu   Arg   Tyr   Arg   Lys   Ala   Gly
  2030         2040         2050
   *     *     *     *     *     *
 TGG   GAT   GCT   TAT   CTC   AAG   AGA   TGC   TCA   GCT   CAA   TAA
 Trp   Asp   Ala   Tyr   Leu   Lys   Arg   Cys   Ser   Ala   Gln   ***
```

FIG. 7

```
   1 GGATCCAATC GTTGAAAGTG ATCAAGCTGA TTACAAAAGT AAGTATGAAA AGAGCCAATG
  61 TTGAGAGTCT CAGGAACCAC ATCGACTTCT TCGTGCCATC CTCCCACATT CTGAAGCCCA
 121 AGAACCCACA AATCATCAAA CACCAACACG ATGCGGACGC CAACCCGAGT TGTAACGCCA
 181 CAAAGTACGG GTACGACCCT GTTCCAGGAG GGCTCACGCC GCAATCAACA ACCAAAGTCG
 241 CCACGATCAA CGCCAGTATC AAGTAAAAGA AGAATAGCAT CTCCAGTCTT CCGATAGCTG
 301 TGTACTTCGA TCTGACGTTG TAGATGATGA TGATCATGAT CACGAGGGCA CCAATGTTGA
 361 CAAAGGCGTT ACCAATCTGG AATATCACGG TATTGGCAAC GTCTATCGGA CGGGCGTAGC
 421 ACTCAGGGAT GATCCCTTCG TTCAGGTGCG TGAACTGCTC GTTCGTCGTT GCCTTCACAA
 481 CCTGGCACAA CGGGAGCGGC GTGTTGTGGC ATAGCGAGTT GAAATCACCG AATGCCATTG
 541 TGTTTTATCG TTAGGGAGAC CTGTTTGAAG CTGACAGCGG GATGAAGATG AGGAAGGAGA
 601 GCACAACAGC TGAGCGGAAG TCTCTGTGAT GCTTGGTGGA CCGGGTGTAG GTGGAATCTC
 661 CCTGGTGAGC GTACTTGCAA CGGTGCTCAG CGACTTCTTC TCGAGAGGAA ACGTAAACAA
 721 AGAGGTTTCA ATGTTGATGT TGATGTGTAT TTTTGTTACA AAAGCAGAAA TTGTAAACAA
 781 AAAGGTATAA TTAGGGCTCT GGTGTAATGA TGGGCACGTG ACGTTACCGT GCTGGTCGAT
 841 TTTAGGGCTA TTGGTTCGCG TCCCGCTGGT GTCCGGGTTA GCGTGTCAAT GTGGCGCCTC
 901 CCGATTATTA CATAAGAAAA CACCCACCCA CGCAACACCT GGTGTCTGGA TGTTGACGCT
 961 TTGTATGCGT GTGTGTGTTT TTTCTTCCGT CTTGTTGGGC CACTCTGCGC GAGCGTTGGC
1021 GACTCACCGG TGAAATTTAT CGAAAACTTT CAGGCTCAGG CCCTTTTCAA CACTACCCTT
1081 TGAGATCACA TCAAGCAGTA ATCAAACACA ATGGGTATGT GGGAAACGAC GACGTGTGCG
1141 GTGTGTGAAT GCCATTAGTG GGATATGTGG TAGTCTCGAG CGTGGATATT ATCGATAGGG
1201 ATGGTGCTTG TTCTATACGT CTTGCTGGGA AGGAAGAAAG CGATGAAGTA TGTGGGAAGA
1261 AGGGGTGGTT TAAGAGAGGA AGTAGACATG TAACAAGTGT GTTCAGAGAA CAAGGACGGA
1321 AATATCACCT ATATGACGTA CACATCACGA ACTGCTCCTG GAGGAAGCGA CAAGATGAAT
1381 ATCAACAGGC ATCATCATAT CTCTACAATG GCTCGTTCCC AAAGCACACG CACAAACAAA
1441 TCCGAGACTT TTGTACTAAC AGCTGTATCT CTGACAAATA GTTAACGTTC CAAAGACCAG
1501 AAGAACCTAC TGTAAGGGTA AGGAGTGCAG AAAGCACACT CAACACAAGG TTACCCAGTA
1561 CAAGGCTGGT AAGGCTTCCC TCTTTGCCCA GGGTAAGCGT CGTTATGACC GTAAGCAATC
1621 CGGTTACGGT GGTCAAACCA AGCCAGTTTT CCACAAAAAG GCTAAAACCA CCAAGAAGGT
1681 TGTTTTGCGT TTGGAGTGTG TTGTCTGCAA GACCAAGGCC CAATTGGCTT TGAAGCGTTG
1741 TAAGCACTTC GAGTTGGGTG GTGACAAGAA GCAAAAGGGT CAAGCTTTGC AATTCTAAGC
1801 TTAAGACAAT TGTTGAAAGT TTTATTATTA TCACTACACT GTGTTTTTGA TGTCATCTAA
1861 TGTAAAAGCG TTTATATTAC CACTTGGTTC GGTATCCTGT AGAAGAATAC GGCCTGTAGC
1921 GTAGCATTCC CACAGGAGGA TCACAGCAAC ATAGACCAAA CAATGTCACG CACGGGGATC
1981 GAACGCGGAA CCAAACCTCT CCCTCCTCCC CCTTTCACCG CGGTTATTTT GTTATGGGCA
2041 CACACAGGGG AAGGAAAAAA ATGCACACAC GCACAAAAGC GAGCTC
```

FIG. 9

```
              10          20         30         40        50
               .     .     .    .    .    .    .    .    .    .
        ATG G GTATGT GGGAAACGAC GACGTGTGCG GTGTGTGAAT GCCATTAGTG
        Met Val>
              60          70         80         90       100        110
               .     .     .    .    .    .    .    .    .    .   .    .
        GGATATGTGG TAGTCTCGAG CGTGGATATT ATCGATAGGG ATGGTGCTTG TTCTATACGT
             120         130        140        150       160        170
              .    .     .    .    .    .    .    .    .    .    .    .
        CTTGCTGGGA AGGAAGAAAG CGATGAAGTA TGTGGGAAGA AGGGGTGGTT TAAGAGAGGA
             180         190        200        210       220        230
              .    .     .    .    .    .    .    .    .    .    .    .
        AGTAGACATG TAACAAGTGT GTTCAGAGAA CAAGGACGGA AATATCACCT ATATGACGTA
             240         250        260        270       280        290
              .    .    .    .    .    .    .    .    .    .    .    .
        CACATCACGA ACTGCTCCTG GAGGAAGCGA CAAGATGAAT ATCAACAGGC ATCATCATAT
             300         310        320        330       340        350
              .    .    .    .    .    .    .    .    .    .    .    .
        CTCTACAATG GCTCGTTCCC AAAGCACACG CACAAACAAA TCCGAGACTT TTGTACTAAC
             360         370        380        390       400
              .    .    .    .    .    .    .    .    .    .
        AGCTGTATCT CTGACAAATA G TT AAC GTT CCA AAG ACC AGA AGA ACC TAC TGT
                                  Asn Val Pro Lys Thr Ser Ser Thr Tyr Cys
               410         420        430        440        450
                .    .    .    .    .    .    .    .    .    .
        AAG GGT AAG GAG TGC AGA AAG CAC ACT CAA CAC AAG GTT ACC CAG TAC
        Lys Gly Lys Glu Cys Ser Lys His Thr Gln His Lys Val Thr Gln Tyr
                460         470        480        490
                 .    .    .    .    .    .    .    .    .
        AAG GCT GGT AAG GCT TCC CTC TTT GCC CAG GGT AAG CGT CGT TAT GAC
        Lys Ala Gly Lys Ala Ser Leu Phe Ala Gln Gly Lys Arg Arg Tyr Asp
        500         510        520        530        540
          .    .    .    .    .    .    .    .    .    .    .
        CGT AAG CAA TCC GGT TAC GGT GGT CAA ACC AAG CCA GTT TTC CAC AAA
        Arg Lys Gln Ser Gly Tyr Gly Gly Gln Thr Lys Pro Val Phe His Lys
        550         560        570        580        590
          .    .    .    .    .    .    .    .    .    .
        AAG GCT AAA ACC ACC AAG AAG GTT GTT TTG CGT TTG GAG TGT GTT GTC
        Lys Ala Lys Thr Thr Lys Lys Val Val Leu Arg Leu Glu Cys Val Val
            600         610        620        630        640
             .    .    .    .    .    .    .    .    .    .
        TGC AAG ACC AAG GCC CAA TTG GCT TTG AAG CGT TGT AAG CAC TTC GAG
        Cys Lys Thr Lys Ala Gln Leu Ala Leu Lys Arg Cys Lys His Phe Glu
             650         660        670        680
              .    .    .    .    .    .    .    .    .
        TTG GGT GGT GAC AAG AAG CAA AAG GGT CAA GCT TTG CAA TTC TAA
        Leu Gly Gly Asp Lys Lys Gln Lys Gly Gln Ala Leu Gln Phe ***
```

FIG. 10 a

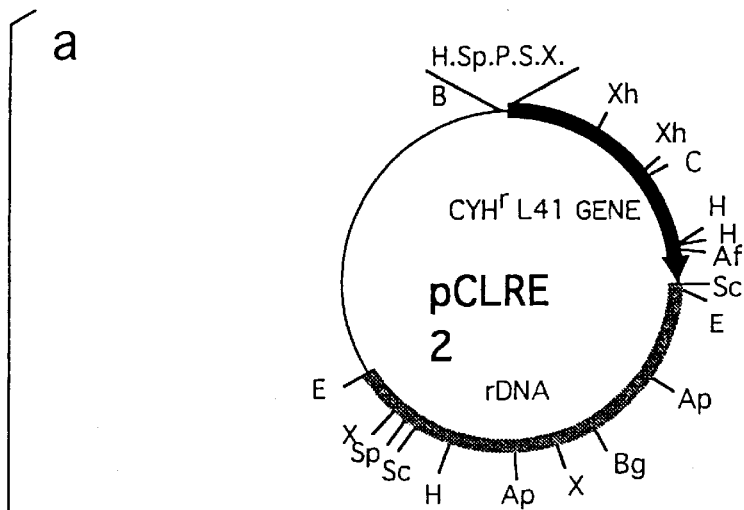

b
```
     -1110                                GGATCCAATCGTTGAAAGTGATCAAGCTGA
                                          BamHI
     -1080  TTACAAAAGTAAGTATGAAAAGAGCCAATGTTGAGAGTCTCAGGAACCACATCGACTTCT
     -1020  TCGTGCCATCCTCCCACATTCTGAAGCCCAAGAACCCACAAATCATCAAACACCAACACG
      -960  ATGCGGACGCCAACCCGAGTTGTAACGCCACAAAGTACGGGTACGACCCTGTTCCAGGAG
      -900  GGCTCACGCCGCAATCAACAACCAAAGTCGCCACGATCAACGCCAGTATCAAGTAAAAGA
      -840  AGAATAGCATCTCCAGTCTTCCGATAGCTGTGTACTTCGATCTGACGTTGTAGATGATGA
      -780  TGATCATGATCACGAGGGCACCAATGTTGACAAAGGCGTTACCAATCTGGAATATCACGG
      -720  TATTGGCAACGTCTATCGGACGGGCGTAGCACTCAGGGATGATCCCTTCGTTCAGGTGCG
      -660  TGAACTGCTCGTTCGTCGTTGCCTTCACAACCTGGCACAACGGGAGCGGCGTGTTGTGGC
      -600  ATAGCGAGTTGAAATCACCGAATGCCATTGTGTTTTATCGTTAGGGAGACCTGTTTGAAG
      -540  CTGACAGCGGGATGAAGATGAGGAAGGAGAGCACAACAGCTGAGCGGAAGTCTCTGTGAT
      -480  GCTTGGTGGACCGGGTGTAGGTGGAATCTCCCTGGTGAGCGTACTTGCAACGGTGCTCAG

-420  CGACTTCTT CTCGAG AGGAAACGTAAACAAAGAGGTTTCAATGTTGATGTTGATGTGTAT
            ↑pCLRE11 XhoI
      -360  TTTTGTTACAAAAGCAGAAATTGTAAACAAAAAGGTATAATTAGGGCTCTGGTGTAATGA

-300  TGGGCACGTGACGTTACCGTGCTGGTCGATTTTAGGGCTATTGGTTCGCGTCCCGCTGGT

-240  GTCCGGGTTAGCGTGTCAATGTGGCGCCTCCCGATTATTACATAAGAAAACACCCACCCA
                                                  pCLRE15 ↑          ↑pCLRE16
      -180  CGCAACACCTGGTGTCTGGATGTTGACGCTTTGTATGCGTGTGTGTGTTTTTTCTTCCGT

-120  CTTGTTGGGCCACTCTGCGCGAGCGTTGGCGACTCACCGGTGAAATTTATCGAAAACTTT
                                                   ↑pCLRE17
       -60  CAGGCTCAGGCCCTTTTCAACACTACCCTTTGAGATCACATCAAGCAGTAATCAAACACA
                    ↑pCLRE18
         1  ATG
            ↑pCLRE19
```

FIG. 13

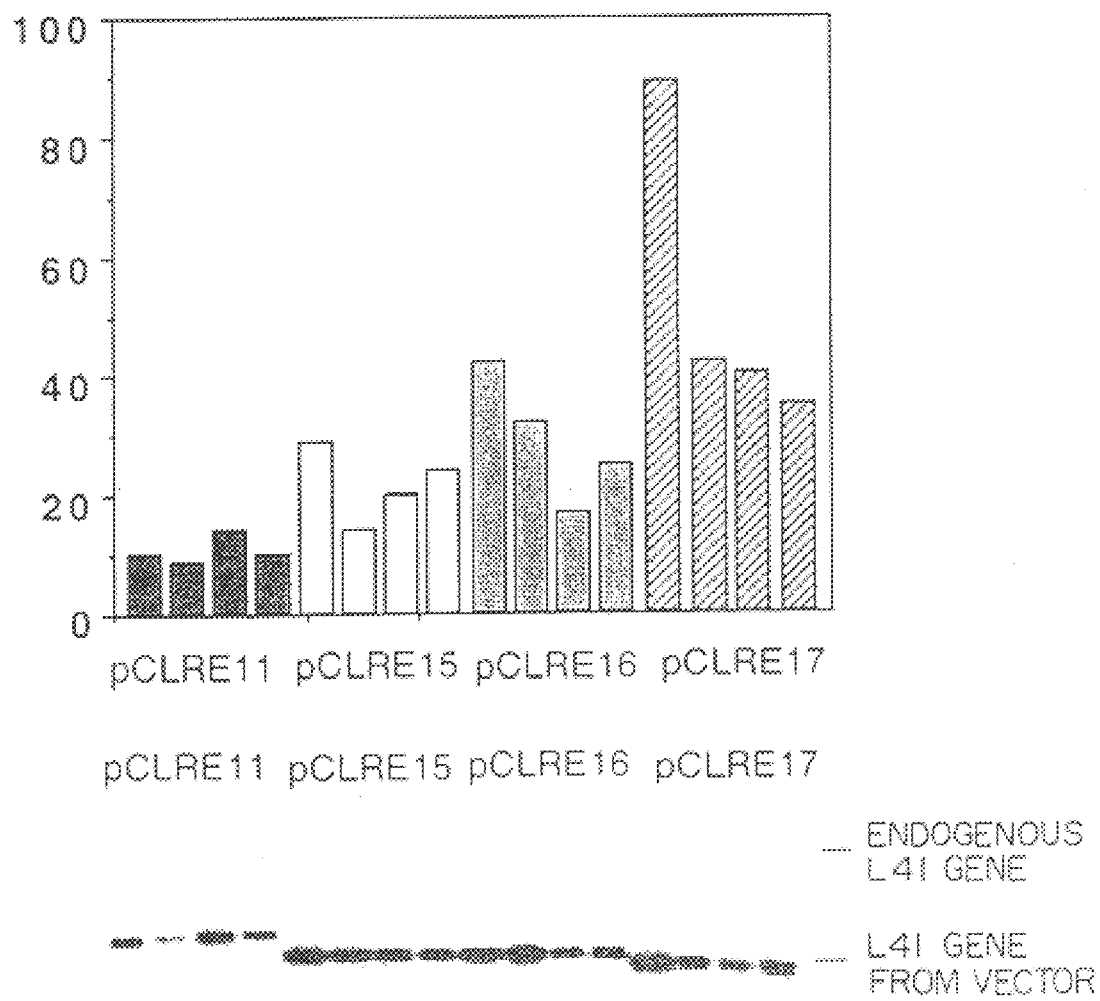
F I G. 14

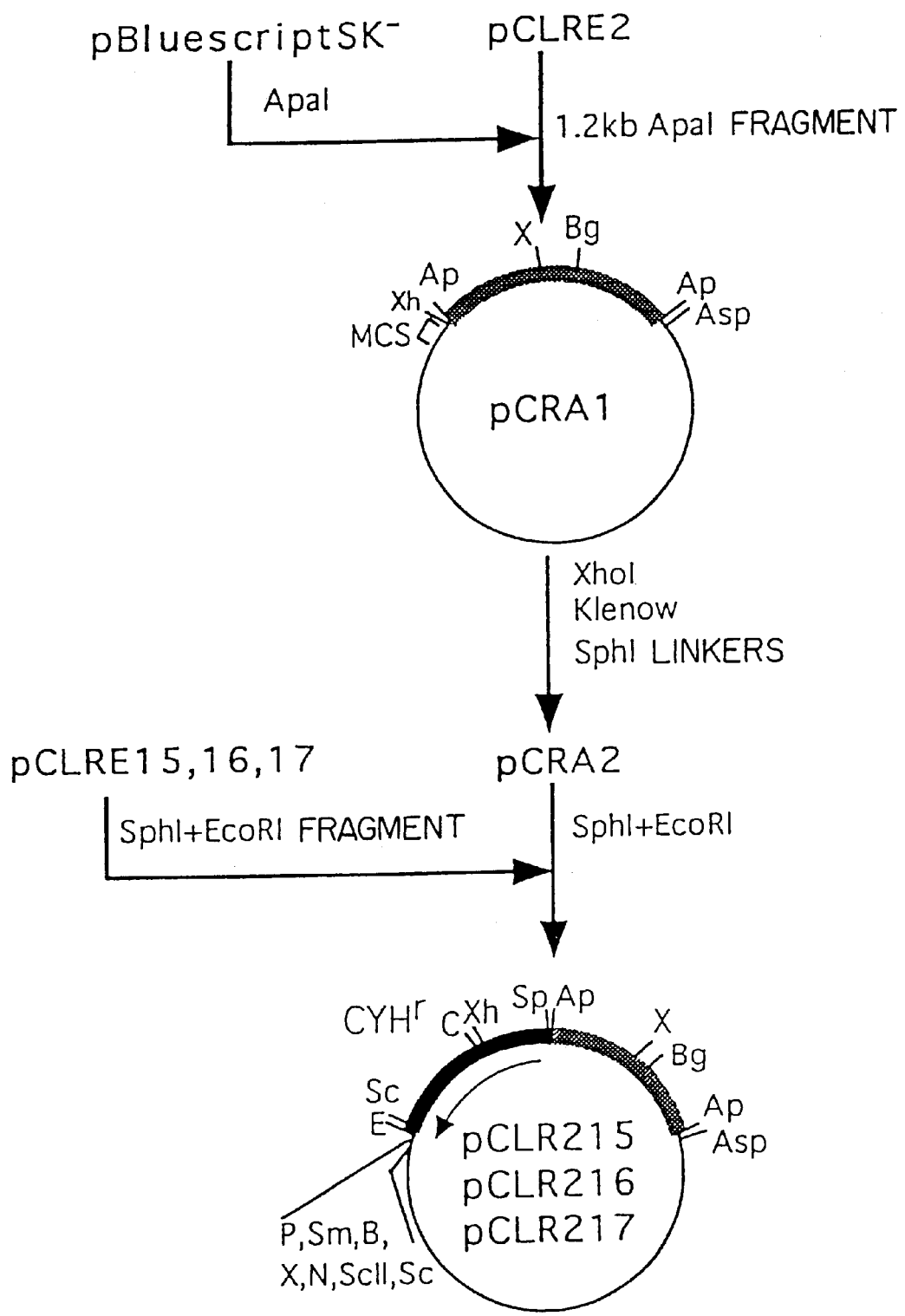
F I G. 15

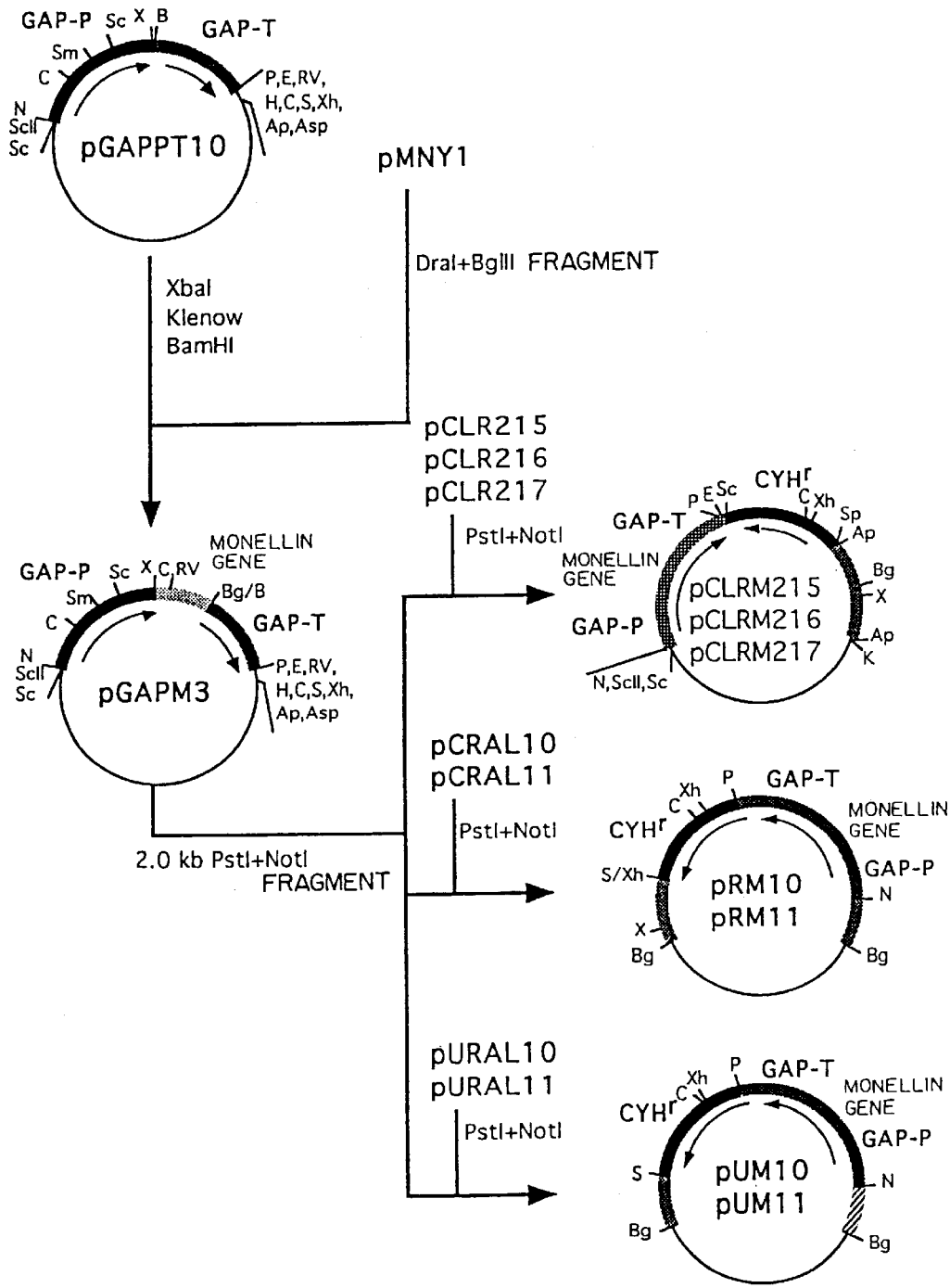
F I G. 20

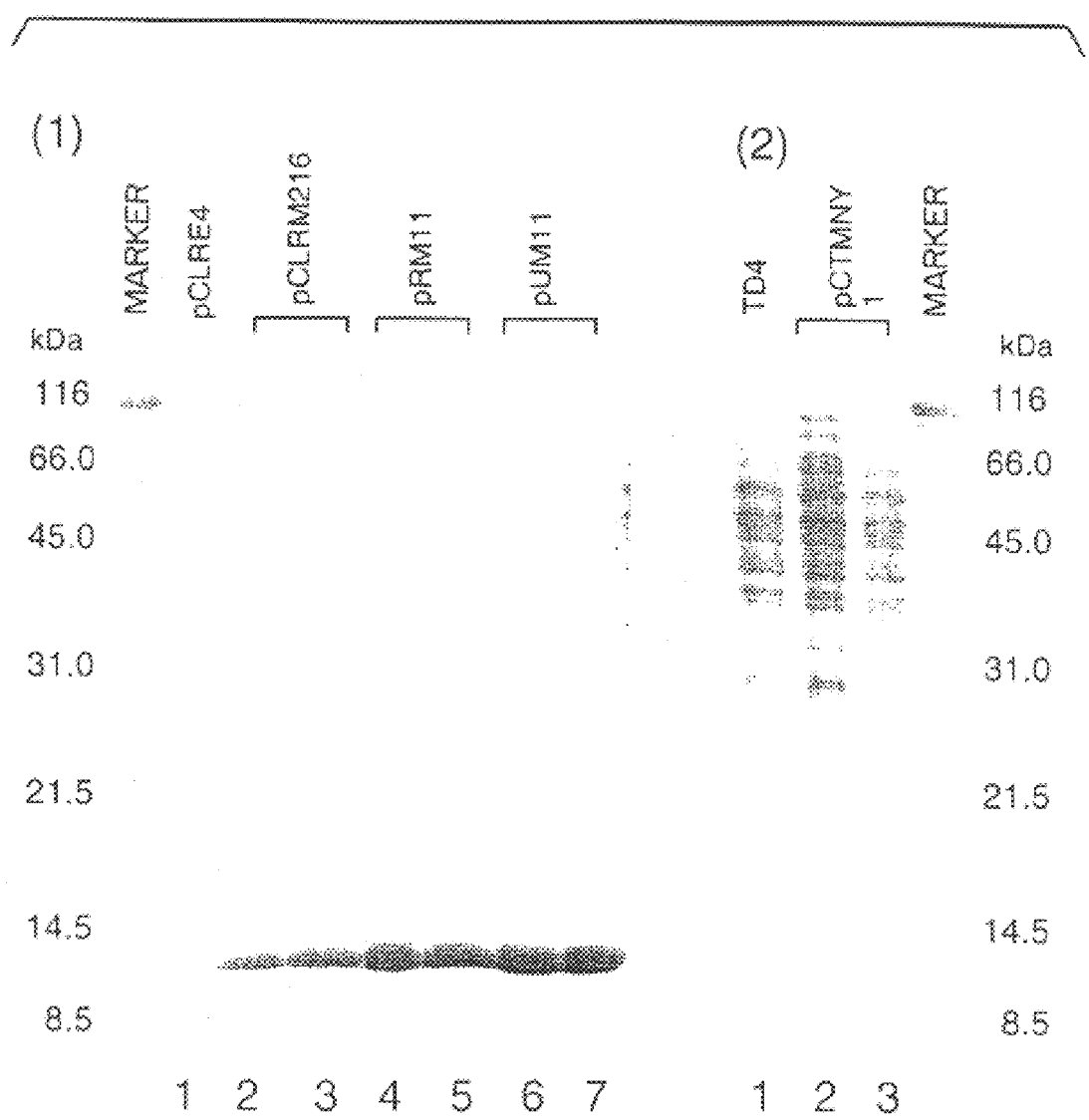
F I G. 21

A-1-1
GGTCTAGATATGACCTTCGCTTACAAGATCGATGGTAACGAGGTTATCTTCACTTTGTGGGCTCCATACCAAAAGTCCGTTAAGTTGAAG

A-1-2
ATACCAAAAGTCCGTTAAGTTGAAGGTCTTGGAGAAGGGTTTGTACGAGATGGAGAGAGACGAGAAGGGTTACTTCACCATCACTTTGA

A-1C-1
GGCCTTGGACTCTTGGATGATTTGAGATGGACCGTGGACACCCTCTGGTTGGTATCTGGAAGCTGGGTCTGGGATCTCGGAAGCATCGTC

A-1C-2
GGTCTGGGATCTCGGAAGCATCGTCCAAAACGTACTTGTATCTGTCTCTGACCTTGACGTTGTTCAAAGTGATGGTGAAGTAACCCTT

A-2-1
AACCAAGGAGTTCAACAACGAGACCTTCTTGAAGAAGGAGGACTTGATCATCTACGAGATCCACGTCGGTACTTTCACCCCAGAGGGTACTTTCGAGGGT

A-2-2
CCCCAGAGGGTACTTTCGAGGGTGTCATCAGAAAGTTGGACTACTTGAAGGATTTGGGTATCACCGCTATCGAGATCATGCCAATCGCTCAATTCCCAGG

A-2C-1
AAGTAGACAACGTCCAAGATAACACCCAAACCCTTCTTGTGAGCCTCATCAACCAACTTTCTGAAACCCTCTGGACCACCGTAGGAGTTTTGGACAGCGT

A-2C-2
ACCGTAGGAGTTTTGGACAGCGTACAAGTAAACACCATCGTAACCCCAGTCTCTCTTACCTGGGAATTGAGCGATTGGCATGATCTCGATAGCGGTGATA

F I G. 24

A-3-1
ATGTCTACAACCATGTTGGTCCAGAGGGTAACTACATGGTTAAGTTGGGTCCATACTTCAGT
CAAAAGTACAAG

A-3-2
CATACTTCAGTCAAAAGTACAAGACCCCATGGGGTTTGACCTTCAACTTCGACGACGCTGA
GTCCGATGAGGTCAGAAAG

A-3C-1
AGCTCGAGGATGTGCTTTGGAGAGGTGTCGATGATAGCGTGGACAGCGTCCAATCTGAAAC
CATCAACGTTGTAC

A-3C-2
AACCATCAACGTTGTACTCCTTGATCCAGTATTCAACGTTCTCCAAGATGAACTTTCTGACC
TCATCGGACTC

A-4-1
TCCTCGAGGAGATCGCTGATGTTGTCCACAAGTACAACAGAATCGTTATCGCTGAGTCCGA
CTTGAACG

A-4-2
GCTGAGTCCGACTTGAACGACCCACGTGTTGTTAACCCAAAGGAGAAGTGTGGTTACAAC
ATCGACGC

A-4C-1
TGGATATCGTCCAAGTTACCGAAGTCAGTGTAGTAACCTTGTCTCTCACCGGTCAAGTAAG
CGTGGATA

A-4C-2
GGTCAAGTAAGCGTGGATAGAGTGGTGGAAATCGTCAACCCATTGAGCGTCGATGTTGTAA
CCACAC

F I G. 25

A-5-1
CAGATATCGTTAAGTCCTACAAGGACGTCTTCGTTTACGATGGTAAGTACTCCAACTTCAGA
AGAAAGACCCACGGTGAGCCAGTTGGTGAGTTGGATGG

A-5C-1
AAGTCGACGAGCTTAATGATTCTCTCACCCTTACCTCTGTTACCGACTTGATCGTGGTTTTGG
ATGTAAACGACGAAGTTACAACCATCCAACTCACCAA

A-6-1
TCGTCGACAGAGAGTCCTACAAGATCGCTGCTGCTTTGTACTTGTTGTCTCCATACATCCCA
ATGATCTTCATGGG

A-6-2
CATCCCAATGATCTTCATGGGTGAGGAGTACGGTGAGGAGAACCCATTCTACTTCTTCTCTG

ACTTCTCCGACTCC

A-6C-1
TCATCGATCTTCCAAGACAACTTGGAAGCGTTGAAGGTGGACTCGTCTTGTGGATCAGTGTC
TTGACCGTTCTCC

A-6C-2
CAGTGTCTTGACCGTTCTCCTTCTTTCTACCCTCTCTAACACCTTGGATCAACTTGGAGTCGG
AGAAGTCAGAGAAG

A-7-1
AGATCGATGAGGAGATTTTCAGTTTCTACAAGATCCTTATCAAGATGAGAAAGGAGTTGTCC
ATCGCTTGTGACAGAAGAGT

A-7-2
CCATCGCTTGTGACAGAAGAGTCAACGTTGTCAACGGTGAGAACTGGTTGATCATCAAGGG
TAGAGAATACTTCTCCTTGTACGTCTTCAG

A-7C-1
CGAGATCTGCTACAACTTGTACAAAGCGAAACCCTTGTCGAACTCGTACTTACCCTCCTCG
ATGTGTTGTGGGAAACTGT

A-7C-2
CGATGTGTTGTGGGAAACTGTTGTTGGAAGACAACAACAAGGTACCACTGTACTTAACCTC
GATGGAGGACTTACTGAAGACGTACAAGGAG

F I G. 26

SEQUENCE LISTING

```
<160> NUMBER OF SEQ ID NOS: 66

<210> SEQ ID NO 1
<211> LENGTH: 192
<212> TYPE: DNA
<213> ORGANISM: Candida utilis

<400> SEQUENCE: 1
aacacccacc cacgcaacac ctggtgtctg gatgttgacg ctttgtatgc gtgtgtgtgt      60
tttttcttcc gtcttgttgg gccactctgc gcgagcgttg gcgactcacc ggtgaaattt     120
atcgaaaact ttcaggctca ggcccttttc aacactaccc tttgagatca catcaagcag    180
taatcaaaca ca                                                         192

<210> SEQ ID NO 2
<211> LENGTH: 184
<212> TYPE: DNA
<213> ORGANISM: Candida utilis

<400> SEQUENCE: 2
cccacgcaac acctggtgtc tggatgttga cgctttgtat gcgtgtgtgt gttttttctt      60
ccgtcttgtt gggccactct gcgcgagcgt tggcgactca ccggtgaaat ttatcgaaaa    120
ctttcaggct caggcccttt tcaacactac cctttgagat cacatcaagc agtaatcaaa    180
caca                                                                  184

<210> SEQ ID NO 3
<211> LENGTH: 82
<212> TYPE: DNA
<213> ORGANISM: Candida utilis

<400> SEQUENCE: 3
ggtgaaattt atcgaaaact ttcaggctca ggcccttttc aacactaccc tttgagatca     60
catcaagcag taatcaaaca ca                                              82

<210> SEQ ID NO 4
<211> LENGTH: 291
<212> TYPE: DNA
<213> ORGANISM: Artificial Sequence
<220> FEATURE:
<223> OTHER INFORMATION: Description of Artificial Sequence: Synthetic
      DNA
<221> NAME/KEY: CDS
<222> LOCATION: (1)..(291)
```

<400> SEQUENCE: 4

```
atg ggc gag tgg gaa atc atc gat atc ggt cca ttc act caa aac ttg      48
Met Gly Glu Trp Glu Ile Ile Asp Ile Gly Pro Phe Thr Gln Asn Leu
  1               5                  10                  15 ggt aaa ttc gct gtt gat gaa gaa aac aag att ggc caa tac ggt aga      96
Gly Lys Phe Ala Val Asp Glu Glu Asn Lys Ile Gly Gln Tyr Gly Arg
             20                  25                  30 ttg acc ttt aac aag gtt atc aga cca tgc atg aag aag act att tac     144
Leu Thr Phe Asn Lys Val Ile Arg Pro Cys Met Lys Lys Thr Ile Tyr
         35                  40                  45 gaa aac gaa ggt ttt aga gaa att aag ggt tac gaa tac caa ttg tac     192
Glu Asn Glu Gly Phe Arg Glu Ile Lys Gly Tyr Glu Tyr Gln Leu Tyr
 50                  55                  60 gta tac gct tct gac aag ttg ttc cgt gct gac att tcc gaa gac tac     240
Val Tyr Ala Ser Asp Lys Leu Phe Arg Ala Asp Ile Ser Glu Asp Tyr
 65                  70                  75                  80 aag aca cgt ggt cgt aag ttg ttg aga ttc aac ggt cca gtc cca cca     288
Lys Thr Arg Gly Arg Lys Leu Leu Arg Phe Asn Gly Pro Val Pro Pro
                 85                  90                  95 cca                                                                  291
Pro
```

<210> SEQ ID NO 5
<211> LENGTH: 97
<212> TYPE: PRT
<213> ORGANISM: Artificial Sequence
<220> FEATURE:
<223> OTHER INFORMATION: Description of Artificial Sequence: Synthetic protein

<400> SEQUENCE: 5

```
Met Gly Glu Trp Glu Ile Ile Asp Ile Gly Pro Phe Thr Gln Asn Leu
  1               5                  10                  15

Gly Lys Phe Ala Val Asp Glu Glu Asn Lys Ile Gly Gln Tyr Gly Arg
             20                  25                  30

Leu Thr Phe Asn Lys Val Ile Arg Pro Cys Met Lys Lys Thr Ile Tyr
         35                  40                  45

Glu Asn Glu Gly Phe Arg Glu Ile Lys Gly Tyr Glu Tyr Gln Leu Tyr
 50                  55                  60

Val Tyr Ala Ser Asp Lys Leu Phe Arg Ala Asp Ile Ser Glu Asp Tyr
 65                  70                  75                  80

Lys Thr Arg Gly Arg Lys Leu Leu Arg Phe Asn Gly Pro Val Pro Pro
                 85                  90                  95

Pro
```

<210> SEQ ID NO 6
<211> LENGTH: 97
<212> TYPE: PRT
<213> ORGANISM: Candida utilis

<400> SEQUENCE: 6

```
Met Gly Glu Trp Glu Ile Ile Asp Ile Gly Pro Phe Thr Gln Asn Leu
  1               5                  10                  15

Gly Lys Phe Ala Val Asp Glu Glu Asn Lys Ile Gly Gln Tyr Gly Arg
             20                  25                  30

Leu Thr Phe Asn Lys Val Ile Arg Pro Cys Met Lys Lys Thr Ile Tyr
         35                  40                  45

Glu Glu Asn Gly Phe Arg Glu Ile Lys Gly Tyr Glu Tyr Gln Leu Tyr
 50                  55                  60
```

Val Tyr Ala Ser Asp Lys Leu Phe Arg Ala Asp Ile Ser Glu Asp Tyr
 65                  70                  75                  80

Lys Thr Arg Gly Arg Lys Leu Leu Arg Phe Asn Gly Pro Val Pro Pro
                 85                  90                  95

Pro

<210> SEQ ID NO 7
<211> LENGTH: 282
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 7
ggtctagata tgaccttcgc ttacaagatc gatggtaacg aggttatctt cactttgtgg    60
gctccatacc aaaagtccgt taagttgaag gtcttggaga agggtttgta cgagatggag   120
agagacgaga agggttactt caccatcact tgaacaacg tcaaggtcag agacagatac    180
aagtacgttt tggacgatgc ttccgagatc ccagacccag cttccagata ccaaccagag   240
ggtgtccacg gtccatctca aatcatccaa gagtccaagg cc                      282

<210> SEQ ID NO 8
<211> LENGTH: 312
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 8
aaccaaggag ttcaacaacg agaccttctt gaagaaggag gacttgatca tctacgagat    60
ccacgtcggt actttcaccc cagagggtac tttcgagggt gtcatcagaa agttggacta   120
cttgaaggat ttgggtatca ccgctatcga gatcatgcca atcgctcaat tcccaggtaa   180
gagagactgg ggttacgatg gtgtttactt gtacgctgtc caaaactcct acggtggtcc   240
agagggtttc agaaagttgg ttgatgaggc tcacaagaag ggtttgggtg ttatcttgga   300
cgttgtctac tt                                                       312

<210> SEQ ID NO 9
<211> LENGTH: 241
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 9
atgtctacaa ccatgttggt ccagagggta actacatggt taagttgggt ccatacttca    60
gtcaaaagta caagacccca tgggggttga ccttcaactt cgacgacgct gagtccgatg   120
aggtcagaaa gttcatcttg gagaacgttg aatactggat caaggagtac aacgttgatg   180
gtttcagatt ggacgctgtc cacgctatca tcgacacctc tccaaagcac atcctcgagg   240
a                                                                   241

<210> SEQ ID NO 10
<211> LENGTH: 214
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 10
tcctcgagga gatcgctgat gttgtccaca agtacaacag aatcgttatc gctgagtccg    60
acttgaacga cccacgtgtt gttaacccaa aggagaagtg tggttacaac atcgacgctc   120
aatgggttga cgatttccac cactctatcc acgcttactt gaccggtgag agacaaggtt   180
actacactga cttcggtaac ttggacgata tcgt                                214

<210> SEQ ID NO 11
<211> LENGTH: 184
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 11
acgatatcgt taagtcctac aaggacgtct tcgtttacga tggtaagtac tccaacttca    60
gaagaaagac ccacggtgag ccagttggtg agttggatgg ttgtaacttc gtcgtttaca   120
tccaaaacca cgatcaagtc ggtaacagag gtaagggtga gagaatcatt aagctcgtcg   180
actt                                                                 184

<210> SEQ ID NO 12
<211> LENGTH: 241
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 12
tcgtcgacag agagtcctac aagatcgctg ctgctttgta cttgttgtct ccatacatcc    60
caatgatctt catgggtgag gagtacggtg aggagaaccc attctacttc ttctctgact   120
tctccgactc caagttgatc caaggtgtta gagagggtag aaagaaggag aacggtcaag   180
acactgatcc acaagacgag tccaccttca acgcttccaa gttgtcttgg aagatcgatg   240
a                                                                    241

<210> SEQ ID NO 13
<211> LENGTH: 284
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 13
agatcgatga ggagattttc agtttctaca agatccttat caagatgaga aaggagttgt    60
ccatcgcttg tgacagaaga gtcaacgttg tcaacggtga gaactggttg atcatcaagg   120
gtagagaata cttctccttg tacgtcttca gtaagtcctc catcgaggtt aagtacagtg   180
gtaccttgtt gttgtcttcc aacaacagtt tcccacaaca catcgaggag ggtaagtacg   240
agttcgacaa gggtttcgct ttgtacaagt tgtagcagat ctgg                    284

<210> SEQ ID NO 14
<211> LENGTH: 1680
<212> TYPE: DNA

<213> ORGANISM: Artificial Sequence
<220> FEATURE:
<223> OTHER INFORMATION: Description of Artificial Sequence: Synthetic DNA
<221> NAME/KEY: CDS
<222> LOCATION: (1)..(1677)

<400> SEQUENCE: 14

| | | | | | | | | | | | | | | | | |
|---|---|---|---|---|---|---|---|---|---|---|---|---|---|---|---|---|
| atg | acc | ttc | gct | tac | aag | atc | gat | ggt | aac | gag | gtt | atc | ttc | act | ttg | 48 |
| Met | Thr | Phe | Ala | Tyr | Lys | Ile | Asp | Gly | Asn | Glu | Val | Ile | Phe | Thr | Leu | |
| 1 | | | | 5 | | | | | 10 | | | | | 15 | | |
| tgg | gct | cca | tac | caa | aag | tcc | gtt | aag | ttg | aag | gtc | ttg | gag | aag | ggt | 96 |
| Trp | Ala | Pro | Tyr | Gln | Lys | Ser | Val | Lys | Leu | Lys | Val | Leu | Glu | Lys | Gly | |
| | | | 20 | | | | | 25 | | | | | 30 | | | |
| ttg | tac | gag | atg | gag | aga | gac | gag | aag | ggt | tac | ttc | acc | atc | act | ttg | 144 |
| Leu | Tyr | Glu | Met | Glu | Arg | Asp | Glu | Lys | Gly | Tyr | Phe | Thr | Ile | Thr | Leu | |
| | | 35 | | | | | 40 | | | | | 45 | | | | |
| aac | aac | gtc | aag | gtc | aga | gac | aga | tac | aag | tac | gtt | ttg | gac | gat | gct | 192 |
| Asn | Asn | Val | Lys | Val | Arg | Asp | Arg | Tyr | Lys | Tyr | Val | Leu | Asp | Asp | Ala | |
| | 50 | | | | | 55 | | | | | 60 | | | | | |
| tcc | gag | atc | cca | gac | cca | gct | tcc | aga | tac | caa | cca | gag | ggt | gtc | cac | 240 |
| Ser | Glu | Ile | Pro | Asp | Pro | Ala | Ser | Arg | Tyr | Gln | Pro | Glu | Gly | Val | His | |
| 65 | | | | | 70 | | | | | 75 | | | | | 80 | |
| ggt | cca | tct | caa | atc | atc | caa | gag | tcc | aag | gag | ttc | aac | aac | gag | acc | 288 |
| Gly | Pro | Ser | Gln | Ile | Ile | Gln | Glu | Ser | Lys | Glu | Phe | Asn | Asn | Glu | Thr | |
| | | | | 85 | | | | | 90 | | | | | 95 | | |
| ttc | ttg | aag | aag | gag | gac | ttg | atc | atc | tac | gag | atc | cac | gtc | ggt | act | 336 |
| Phe | Leu | Lys | Lys | Glu | Asp | Leu | Ile | Ile | Tyr | Glu | Ile | His | Val | Gly | Thr | |
| | | | 100 | | | | | 105 | | | | | 110 | | | |
| ttc | acc | cca | gag | ggt | act | ttc | gag | ggt | gtc | atc | aga | aag | ttg | gac | tac | 384 |
| Phe | Thr | Pro | Glu | Gly | Thr | Phe | Glu | Gly | Val | Ile | Arg | Lys | Leu | Asp | Tyr | |
| | | 115 | | | | | 120 | | | | | 125 | | | | |
| ttg | aag | gat | ttg | ggt | atc | acc | gct | atc | gag | atc | atg | cca | atc | gct | caa | 432 |
| Leu | Lys | Asp | Leu | Gly | Ile | Thr | Ala | Ile | Glu | Ile | Met | Pro | Ile | Ala | Gln | |
| | 130 | | | | | 135 | | | | | 140 | | | | | |
| ttc | cca | ggt | aag | aga | gac | tgg | ggt | tac | gat | ggt | gtt | tac | ttg | tac | gct | 480 |
| Phe | Pro | Gly | Lys | Arg | Asp | Trp | Gly | Tyr | Asp | Gly | Val | Tyr | Leu | Tyr | Ala | |
| 145 | | | | | 150 | | | | | 155 | | | | | 160 | |
| gtc | caa | aac | tcc | tac | ggt | ggt | cca | gag | ggt | ttc | aga | aag | ttg | gtt | gat | 528 |
| Val | Gln | Asn | Ser | Tyr | Gly | Gly | Pro | Glu | Gly | Phe | Arg | Lys | Leu | Val | Asp | |
| | | | | 165 | | | | | 170 | | | | | 175 | | |
| gag | gct | cac | aag | aag | ggt | ttg | ggt | gtt | atc | ttg | gac | gtt | gtc | tac | aac | 576 |
| Glu | Ala | His | Lys | Lys | Gly | Leu | Gly | Val | Ile | Leu | Asp | Val | Val | Tyr | Asn | |
| | | | 180 | | | | | 185 | | | | | 190 | | | |
| cat | gtt | ggt | cca | gag | ggt | aac | tac | atg | gtt | aag | ttg | ggt | cca | tac | ttc | 624 |
| His | Val | Gly | Pro | Glu | Gly | Asn | Tyr | Met | Val | Lys | Leu | Gly | Pro | Tyr | Phe | |
| | | 195 | | | | | 200 | | | | | 205 | | | | |
| agt | caa | aag | tac | aag | acc | cca | tgg | ggt | ttg | acc | ttc | aac | ttc | gac | gac | 672 |
| Ser | Gln | Lys | Tyr | Lys | Thr | Pro | Trp | Gly | Leu | Thr | Phe | Asn | Phe | Asp | Asp | |
| | 210 | | | | | 215 | | | | | 220 | | | | | |
| gct | gag | tcc | gat | gag | gtc | aga | aag | ttc | atc | ttg | gag | aac | gtt | gaa | tac | 720 |
| Ala | Glu | Ser | Asp | Glu | Val | Arg | Lys | Phe | Ile | Leu | Glu | Asn | Val | Glu | Tyr | |
| 225 | | | | | 230 | | | | | 235 | | | | | 240 | |
| tgg | atc | aag | gag | tac | aac | gtt | gat | ggt | ttc | aga | ttg | gac | gct | gtc | cac | 768 |
| Trp | Ile | Lys | Glu | Tyr | Asn | Val | Asp | Gly | Phe | Arg | Leu | Asp | Ala | Val | His | |
| | | | | 245 | | | | | 250 | | | | | 255 | | |
| gct | atc | atc | gac | acc | tct | cca | aag | cac | atc | ctc | gag | gag | atc | gct | gat | 816 |
| Ala | Ile | Ile | Asp | Thr | Ser | Pro | Lys | His | Ile | Leu | Glu | Glu | Ile | Ala | Asp | |
| | | | 260 | | | | | 265 | | | | | 270 | | | |
| gtt | gtc | cac | aag | tac | aac | aga | atc | gtt | atc | gct | gag | tcc | gac | ttg | aac | 864 |
| Val | Val | His | Lys | Tyr | Asn | Arg | Ile | Val | Ile | Ala | Glu | Ser | Asp | Leu | Asn | |

|  |  |  |  |  |  |  |  |  |  |  |  |  |  |  |  |
|---|---|---|---|---|---|---|---|---|---|---|---|---|---|---|---|
|  |  | 275 |  |  |  |  | 280 |  |  |  |  | 285 |  |  |  |
| gac | cca | cgt | gtt | gtt | aac | cca | aag | gag | aag | tgt | ggt | tac | aac | atc | gac | 912 |
| Asp | Pro | Arg | Val | Val | Asn | Pro | Lys | Glu | Lys | Cys | Gly | Tyr | Asn | Ile | Asp |  |
|  | 290 |  |  |  |  | 295 |  |  |  |  | 300 |  |  |  |  |  |
| gct | caa | tgg | gtt | gac | gat | ttc | cac | cac | tct | atc | cac | gct | tac | ttg | acc | 960 |
| Ala | Gln | Trp | Val | Asp | Asp | Phe | His | His | Ser | Ile | His | Ala | Tyr | Leu | Thr |  |
| 305 |  |  |  |  | 310 |  |  |  |  | 315 |  |  |  |  | 320 |  |
| ggt | gag | aga | caa | ggt | tac | tac | act | gac | ttc | ggt | aac | ttg | gac | gat | atc | 1008 |
| Gly | Glu | Arg | Gln | Gly | Tyr | Tyr | Thr | Asp | Phe | Gly | Asn | Leu | Asp | Asp | Ile |  |
|  |  |  |  | 325 |  |  |  |  | 330 |  |  |  |  | 335 |  |  |
| gtt | aag | tcc | tac | aag | gac | gtc | ttc | gtt | tac | gat | ggt | aag | tac | tcc | aac | 1056 |
| Val | Lys | Ser | Tyr | Lys | Asp | Val | Phe | Val | Tyr | Asp | Gly | Lys | Tyr | Ser | Asn |  |
|  |  |  | 340 |  |  |  |  | 345 |  |  |  |  | 350 |  |  |  |
| ttc | aga | aga | aag | acc | cac | ggt | gag | cca | gtt | ggt | gag | ttg | gat | ggt | tgt | 1104 |
| Phe | Arg | Arg | Lys | Thr | His | Gly | Glu | Pro | Val | Gly | Glu | Leu | Asp | Gly | Cys |  |
|  |  | 355 |  |  |  |  | 360 |  |  |  |  | 365 |  |  |  |  |
| aac | ttc | gtc | gtt | tac | atc | caa | aac | cac | gat | caa | gtc | ggt | aac | aga | ggt | 1152 |
| Asn | Phe | Val | Val | Tyr | Ile | Gln | Asn | His | Asp | Gln | Val | Gly | Asn | Arg | Gly |  |
|  | 370 |  |  |  |  | 375 |  |  |  |  | 380 |  |  |  |  |  |
| aag | ggt | gag | aga | atc | att | aag | ctc | gtc | gac | aga | gag | tcc | tac | aag | atc | 1200 |
| Lys | Gly | Glu | Arg | Ile | Ile | Lys | Leu | Val | Asp | Arg | Glu | Ser | Tyr | Lys | Ile |  |
| 385 |  |  |  |  | 390 |  |  |  |  | 395 |  |  |  |  | 400 |  |
| gct | gct | gct | ttg | tac | ttg | ttg | tct | cca | tac | atc | cca | atg | atc | ttc | atg | 1248 |
| Ala | Ala | Ala | Leu | Tyr | Leu | Leu | Ser | Pro | Tyr | Ile | Pro | Met | Ile | Phe | Met |  |
|  |  |  |  | 405 |  |  |  |  | 410 |  |  |  |  | 415 |  |  |
| ggt | gag | gag | tac | ggt | gag | gag | aac | cca | ttc | tac | ttc | ttc | tct | gac | ttc | 1296 |
| Gly | Glu | Glu | Tyr | Gly | Glu | Glu | Asn | Pro | Phe | Tyr | Phe | Phe | Ser | Asp | Phe |  |
|  |  |  | 420 |  |  |  |  | 425 |  |  |  |  | 430 |  |  |  |
| tcc | gac | tcc | aag | ttg | atc | caa | ggt | gtt | aga | gag | ggt | aga | aag | aag | gag | 1344 |
| Ser | Asp | Ser | Lys | Leu | Ile | Gln | Gly | Val | Arg | Glu | Gly | Arg | Lys | Lys | Glu |  |
|  |  | 435 |  |  |  |  | 440 |  |  |  |  | 445 |  |  |  |  |
| aac | ggt | caa | gac | act | gat | cca | caa | gac | gag | tcc | acc | ttc | aac | gct | tcc | 1392 |
| Asn | Gly | Gln | Asp | Thr | Asp | Pro | Gln | Asp | Glu | Ser | Thr | Phe | Asn | Ala | Ser |  |
|  | 450 |  |  |  |  | 455 |  |  |  |  | 460 |  |  |  |  |  |
| aag | ttg | tct | tgg | aag | atc | gat | gag | gag | att | ttc | agt | ttc | tac | aag | atc | 1440 |
| Lys | Leu | Ser | Trp | Lys | Ile | Asp | Glu | Glu | Ile | Phe | Ser | Phe | Tyr | Lys | Ile |  |
| 465 |  |  |  |  | 470 |  |  |  |  | 475 |  |  |  |  | 480 |  |
| ctt | atc | aag | atg | aga | aag | gag | ttg | tcc | atc | gct | tgt | gac | aga | aga | gtc | 1488 |
| Leu | Ile | Lys | Met | Arg | Lys | Glu | Leu | Ser | Ile | Ala | Cys | Asp | Arg | Arg | Val |  |
|  |  |  |  | 485 |  |  |  |  | 490 |  |  |  |  | 495 |  |  |
| aac | gtt | gtc | aac | ggt | gag | aac | tgg | ttg | atc | atc | aag | ggt | aga | gaa | tac | 1536 |
| Asn | Val | Val | Asn | Gly | Glu | Asn | Trp | Leu | Ile | Ile | Lys | Gly | Arg | Glu | Tyr |  |
|  |  |  | 500 |  |  |  |  | 505 |  |  |  |  | 510 |  |  |  |
| ttc | tcc | ttg | tac | gtc | ttc | agt | aag | tcc | tcc | atc | gag | gtt | aag | tac | agt | 1584 |
| Phe | Ser | Leu | Tyr | Val | Phe | Ser | Lys | Ser | Ser | Ile | Glu | Val | Lys | Tyr | Ser |  |
|  |  | 515 |  |  |  |  | 520 |  |  |  |  | 525 |  |  |  |  |
| ggt | acc | ttg | ttg | ttg | tct | tcc | aac | aac | agt | ttc | cca | caa | cac | atc | gag | 1632 |
| Gly | Thr | Leu | Leu | Leu | Ser | Ser | Asn | Asn | Ser | Phe | Pro | Gln | His | Ile | Glu |  |
|  | 530 |  |  |  |  | 535 |  |  |  |  | 540 |  |  |  |  |  |
| gag | ggt | aag | tac | gag | ttc | gac | aag | ggt | ttc | gct | ttg | tac | aag | ttg | tag | 1680 |
| Glu | Gly | Lys | Tyr | Glu | Phe | Asp | Lys | Gly | Phe | Ala | Leu | Tyr | Lys | Leu |  |  |
| 545 |  |  |  |  | 550 |  |  |  |  | 555 |  |  |  |  |  |  |

<210> SEQ ID NO 15
<211> LENGTH: 559
<212> TYPE: PRT
<213> ORGANISM: Artificial Sequence
<220> FEATURE:
<223> OTHER INFORMATION: Description of Artificial Sequence: Synthetic protein

```
<400> SEQUENCE: 15

Met Thr Phe Ala Tyr Lys Ile Asp Gly Asn Glu Val Ile Phe Thr Leu
 1               5                  10                  15

Trp Ala Pro Tyr Gln Lys Ser Val Lys Leu Lys Val Leu Glu Lys Gly
                20                  25                  30

Leu Tyr Glu Met Glu Arg Asp Glu Lys Gly Tyr Phe Thr Ile Thr Leu
            35                  40                  45

Asn Asn Val Lys Val Arg Asp Arg Tyr Lys Tyr Val Leu Asp Asp Ala
 50                  55                  60

Ser Glu Ile Pro Asp Pro Ala Ser Arg Tyr Gln Pro Glu Gly Val His
 65                  70                  75                  80

Gly Pro Ser Gln Ile Ile Gln Glu Ser Lys Glu Phe Asn Asn Glu Thr
                85                  90                  95

Phe Leu Lys Lys Glu Asp Leu Ile Ile Tyr Glu Ile His Val Gly Thr
            100                 105                 110

Phe Thr Pro Glu Gly Thr Phe Glu Gly Val Ile Arg Lys Leu Asp Tyr
            115                 120                 125

Leu Lys Asp Leu Gly Ile Thr Ala Ile Glu Ile Met Pro Ile Ala Gln
130                 135                 140

Phe Pro Gly Lys Arg Asp Trp Gly Tyr Asp Gly Val Tyr Leu Tyr Ala
145                 150                 155                 160

Val Gln Asn Ser Tyr Gly Gly Pro Glu Gly Phe Arg Lys Leu Val Asp
                165                 170                 175

Glu Ala His Lys Lys Gly Leu Gly Val Ile Leu Asp Val Val Tyr Asn
            180                 185                 190

His Val Gly Pro Glu Gly Asn Tyr Met Val Lys Leu Gly Pro Tyr Phe
            195                 200                 205

Ser Gln Lys Tyr Lys Thr Pro Trp Gly Leu Thr Phe Asn Phe Asp Asp
210                 215                 220

Ala Glu Ser Asp Glu Val Arg Lys Phe Ile Leu Glu Asn Val Glu Tyr
225                 230                 235                 240

Trp Ile Lys Glu Tyr Asn Val Asp Gly Phe Arg Leu Asp Ala Val His
                245                 250                 255

Ala Ile Ile Asp Thr Ser Pro Lys His Ile Leu Glu Glu Ile Ala Asp
            260                 265                 270

Val Val His Lys Tyr Asn Arg Ile Val Ile Ala Glu Ser Asp Leu Asn
            275                 280                 285

Asp Pro Arg Val Val Asn Pro Lys Glu Lys Cys Gly Tyr Asn Ile Asp
290                 295                 300

Ala Gln Trp Val Asp Asp Phe His His Ser Ile His Ala Tyr Leu Thr
305                 310                 315                 320

Gly Glu Arg Gln Gly Tyr Tyr Thr Asp Phe Gly Asn Leu Asp Asp Ile
                325                 330                 335

Val Lys Ser Tyr Lys Asp Val Phe Val Tyr Asp Gly Lys Tyr Ser Asn
            340                 345                 350

Phe Arg Arg Lys Thr His Gly Glu Pro Val Gly Glu Leu Asp Gly Cys
            355                 360                 365

Asn Phe Val Val Tyr Ile Gln Asn His Asp Gln Val Gly Asn Arg Gly
370                 375                 380

Lys Gly Glu Arg Ile Ile Lys Leu Val Asp Arg Glu Ser Tyr Lys Ile
385                 390                 395                 400

Ala Ala Ala Leu Tyr Leu Leu Ser Pro Tyr Ile Pro Met Ile Phe Met
                405                 410                 415
```

```
Gly Glu Glu Tyr Gly Glu Asn Pro Phe Tyr Phe Ser Asp Phe
            420                 425                 430

Ser Asp Ser Lys Leu Ile Gln Gly Val Arg Glu Gly Arg Lys Lys Glu
            435                 440                 445

Asn Gly Gln Asp Thr Asp Pro Gln Asp Glu Ser Thr Phe Asn Ala Ser
            450                 455                 460

Lys Leu Ser Trp Lys Ile Asp Glu Glu Ile Phe Ser Phe Tyr Lys Ile
465                 470                 475                 480

Leu Ile Lys Met Arg Lys Glu Leu Ser Ile Ala Cys Asp Arg Arg Val
                485                 490                 495

Asn Val Val Asn Gly Glu Asn Trp Leu Ile Ile Lys Gly Arg Glu Tyr
            500                 505                 510

Phe Ser Leu Tyr Val Phe Ser Lys Ser Ile Glu Val Lys Tyr Ser
            515                 520                 525

Gly Thr Leu Leu Leu Ser Ser Asn Asn Ser Phe Pro Gln His Ile Glu
            530                 535                 540

Glu Gly Lys Tyr Glu Phe Asp Lys Gly Phe Ala Leu Tyr Lys Leu
545                 550                 555

<210> SEQ ID NO 16
<211> LENGTH: 15
<212> TYPE: DNA
<213> ORGANISM: Artificial Sequence
<220> FEATURE:
<223> OTHER INFORMATION: Description of Artificial Sequence: Sequence
      which is common to intron

<400> SEQUENCE: 16
gtatgttact aacag                                                        15

<210> SEQ ID NO 17
<211> LENGTH: 23
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 17
tgtggaaaac ttgcttggtt tga                                               23

<210> SEQ ID NO 18
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 18
agcggccgct                                                              10

<210> SEQ ID NO 19
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 19
cctgcaggaa acgtaaacaa agaggtttca                                        30
```

<210> SEQ ID NO 20
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 20
cctgcaggcc cacgcaacac ctggtgtctg                             30

<210> SEQ ID NO 21
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 21
ggtcgactcg cttttgtgcg tgtgtgcatt                             30

<210> SEQ ID NO 22
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 22
gggtcgacat gtcaccacgt tatcgtacac                             30

<210> SEQ ID NO 23
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 23
ggagatctgc ccattgcgca atctt                                  25

<210> SEQ ID NO 24
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 24
ggagatctca ccaacgccca cggtgt                                 26

<210> SEQ ID NO 25
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 25
ggggtaccta gccaccactg acaacctcat                             30

<210> SEQ ID NO 26
<211> LENGTH: 27
<212> TYPE: DNA
<213> ORGANISM: Artificial Sequence
<220> FEATURE:
<223> OTHER INFORMATION: Description of Artificial Sequence: Primer

```
<400> SEQUENCE: 26
cctgcagacc ggtgaaattt atcgaaa                                    27

<210> SEQ ID NO 27
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 27
gagatctgat gatgcctgtt gatattcatc                                 30

<210> SEQ ID NO 28
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 28
gagatctcta caatggctcg ttccca                                     26

<210> SEQ ID NO 29
<211> LENGTH: 36
<212> TYPE: DNA
<213> ORGANISM: Artificial Sequence
<220> FEATURE:
<223> OTHER INFORMATION: Description of Artificial Sequence: Primer

<400> SEQUENCE: 29
cctgcagggc ggccgctttt gtgcgtgtgt gcattt                          36

<210> SEQ ID NO 30
<211> LENGTH: 38
<212> TYPE: DNA
<213> ORGANISM: Artificial Sequence
<220> FEATURE:
<223> OTHER INFORMATION: Description of Artificial Sequence: Primer

<400> SEQUENCE: 30
agcggccgct agcttacagc gagcactcaa atctgccc                        38

<210> SEQ ID NO 31
<211> LENGTH: 41
<212> TYPE: DNA
<213> ORGANISM: Artificial Sequence
<220> FEATURE:
<223> OTHER INFORMATION: Description of Artificial Sequence: Primer

<400> SEQUENCE: 31
gggatcctct agatatgttg tttgtaagtg tgttttgtat c                    41

<210> SEQ ID NO 32
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 32
ggggatccat tgtatgactt ttatttatgg                                 30

<210> SEQ ID NO 33
<211> LENGTH: 28
```

```
<212> TYPE: DNA
<213> ORGANISM: Artificial Sequence
<220> FEATURE:
<223> OTHER INFORMATION: Description of Artificial Sequence: Primer

<400> SEQUENCE: 33
ccctgcaggg ataaagctga agaataat                                       28

<210> SEQ ID NO 34
<211> LENGTH: 2330
<212> TYPE: DNA
<213> ORGANISM: Candida utilis

<400> SEQUENCE: 34
aagcttatgg aggagattgg gaagattgaa cgaggtgaga tggacacgtt gctgattgac    60
gagatcggca agaaggaggc acctgtggtg aaaccactta cacccgacgt ggatagtaat   120
gtaacagggg aaccgactgg acatagttct acgacaccac caccggtgga acaggactcg   180
agcacaacca cgaggaagag agcacaagac gatggtgagg aaaacacaag gaagaagccc   240
aaggttgagg cagagaaaaa ggcagagcaa gaggcagaga agaggcagag aaagaggca    300 gagaaagagg cagagcaaga ggcagagaaa gaggctccgc gtgcagtgcc gaacaagaga   360
ctacaacaca ttgctactcc tctcatcgag agcatctcgt catacaagta cgcctcagcg   420
tttctacacc ctgttaacga gtccagtgca cccaactatt actctctgat caagaaacca   480
agggatctga agaccatcaa acagatggtc aaggacggac gtatacagac caatcttgag   540
ctggagaggg agatcttgct gatgtttgcc aatgccatca tgtacaacaa gaccgggacg   600
gatatctacg agtggaccaa ggagatgcag ccggaagttg acaagctcat cgagctgttt   660
aacgagagta aataggatac aggctagaga tcaaagaag aatagaaaca gctcgataaa    720
acggtattgt aagtggtatg tacaaagggg tgtgtcttgc tcaacgtctt tgcatctgct   780
gagtcaaagc agcgttctgc tcttggaatc taagaccgac tctttccgaa tgcttgagga   840 actttcaga gcacttcaac acacaggatt cctcctttga tgatagcttt tcagaggtga    900
agtcgttgac acagtcgctg aaacaacgct caacgaggtt ggaataaaga cgcataaagt   960
ccttcatctg cttctgctca caagctgct ggaactgctg ctgctctttt gggttcaatt   1020
ggtccatcct tgctactttt ccgcctagtt tcgattccga ttctgataga gaagcccagc   1080
tatgaatgga agaaattttt cacttttgta tgtcctttt ttcacgcttc gttgcttcgg   1140
acaaaaaaat agtggaggca ctcggtggag ggaagctatc ctcgagatga aaaatttcaa   1200
gctcatctca tcgtccaagt gggacagcaa gctgaggctt ctgaagaggt tgaggaaaat   1260
ggtcaccacg ttatcgtaca cagagagggc atcgcagcac ccttcgccac ttgctaagcg   1320
tctgttttcg cttatggagt ccaagaagac gaacctgtgt gccagtgtcg atgttcgtac   1380
cacagaggag ttgctcaagc tcgttgatac gcttggtcct tatatctgtc tgttgaagac   1440
gcatattgat atcattgatg acttctctat ggagtctact gtggctccac tgttggagct   1500
ttcaaagaag cacaatttcc tcatctttga ggaccgtaag tttgctgata tcggcaacac   1560
cgtcaaggca cagtacgccg gtggtgcgtt caagattgcg caatgggcag atatcaccaa   1620 cgcccacgt gtcaccggtg caggtatcgt caaggggttg aaggaggctg cacaggaaac   1680
cacggatgag ccaagagggc tgttgatgct tgcggagctg agctccaagg gctccttggc   1740
ccacgggaca tataccgagg agaccgtgga gattgccaaa actgataagg acttttgtat   1800
tggattcatc gcacagagag acatgggtgg cagagaagat gggttcgact ggatcatcat   1860
```

-continued

```
gacaccaggc gtgggactcg acgataaggg cgactccctg gccaacagt acagaactgt    1920 cgatgaggtt gtcagtggtg gctctgacat catcatcgtt ggtagaggct tgtttggaaa    1980
gggaagagat ccaacagtgg aaggtgagcg ttatagaaaa gcaggctggg atgcttatct    2040
caagagatgc tcagctcaat aagcgttgag ctctggcttg tataggttca cttgtataaa    2100
atgttcatta ctgttttcgg aagttgtaga ttgccatttt tgcgcaaatt gacgccagtc    2160 ttttttttgcg ccaaatgtca gttttttttgc gccaaaattt acttcatctt atacaactgc    2220
aaaaaccatc caatccaatc cagaaaggac tgatcaatgg tggtgattga ctcaagttct    2280
gatgctacac aacagacaga gctctctaaa aagaattcga tatcaagctt               2330
```

<210> SEQ ID NO 35
<211> LENGTH: 804
<212> TYPE: DNA
<213> ORGANISM: Candida utilis
<220> FEATURE:
<221> NAME/KEY: CDS
<222> LOCATION: (1)..(801)

<400> SEQUENCE: 35

```
atg gtc acc acg tta tcg tac aca gag agg gca tcg cag cac cct tcg    48
Met Val Thr Thr Leu Ser Tyr Thr Glu Arg Ala Ser Gln His Pro Ser
 1               5                  10                  15 cca ctt gct aag cgt ctg ttt tcg ctt atg gag tcc aag aag acg aac    96
Pro Leu Ala Lys Arg Leu Phe Ser Leu Met Glu Ser Lys Lys Thr Asn
             20                  25                  30 ctg tgt gcc agt gtc gat gtt cgt acc aca gag gag ttg ctc aag ctc    144
Leu Cys Ala Ser Val Asp Val Arg Thr Thr Glu Glu Leu Leu Lys Leu
         35                  40                  45 gtt gat acg ctt ggt cct tat atc tgt ctg ttg aag acg cat att gat    192
Val Asp Thr Leu Gly Pro Tyr Ile Cys Leu Leu Lys Thr His Ile Asp
     50                  55                  60 atc att gat gac ttc tct atg gag tct act gtg gct cca ctg ttg gag    240
Ile Ile Asp Asp Phe Ser Met Glu Ser Thr Val Ala Pro Leu Leu Glu
 65                  70                  75                  80 ctt tca aag aag cac aat ttc ctc atc ttt gag gac cgt aag ttt gct    288
Leu Ser Lys Lys His Asn Phe Leu Ile Phe Glu Asp Arg Lys Phe Ala
                 85                  90                  95 gat atc ggc aac acc gtc aag gca cag tac gcc ggt ggt gcg ttc aag    336
Asp Ile Gly Asn Thr Val Lys Ala Gln Tyr Ala Gly Gly Ala Phe Lys
            100                 105                 110 att gcg caa tgg gca gat atc acc aac gcc cac ggt gtc acc ggt gca    384
Ile Ala Gln Trp Ala Asp Ile Thr Asn Ala His Gly Val Thr Gly Ala
        115                 120                 125 ggt atc gtc aag ggg ttg aag gag gct gca cag gaa acc acg gat gag    432
Gly Ile Val Lys Gly Leu Lys Glu Ala Ala Gln Glu Thr Thr Asp Glu
    130                 135                 140 cca aga ggg ctg ttg atg ctt gcg gag ctg agc tcc aag ggc tcc ttg    480
Pro Arg Gly Leu Leu Met Leu Ala Glu Leu Ser Ser Lys Gly Ser Leu
145                 150                 155                 160 gcc cac ggg aca tat acc gag gag acc gtg gag att gcc aaa act gat    528
Ala His Gly Thr Tyr Thr Glu Glu Thr Val Glu Ile Ala Lys Thr Asp
                165                 170                 175 aag gac ttt tgt att gga ttc atc gca cag aga gac atg ggt ggc aga    576
Lys Asp Phe Cys Ile Gly Phe Ile Ala Gln Arg Asp Met Gly Gly Arg
            180                 185                 190 gaa gat ggg ttc gac tgg atc atc atg aca cca ggc gtg gga ctc gac    624
Glu Asp Gly Phe Asp Trp Ile Ile Met Thr Pro Gly Val Gly Leu Asp
        195                 200                 205 gat aag ggc gac tcc ctg ggc caa cag tac aga act gtc gat gag gtt    672
```

| | | | | | | | | | | | | |
|---|---|---|---|---|---|---|---|---|---|---|---|---|
|Asp|Lys|Gly|Asp|Ser|Leu|Gly|Gln|Gln|Tyr|Arg|Thr|Val|Asp|Glu|Val|
| |210| | | |215| | | |220| | | | | | |

| | | | | | | | | | | | | |
|---|---|---|---|---|---|---|---|---|---|---|---|---|
|gtc|agt|ggt|ggc|tct|gac|atc|atc|atc|gtt|ggt|aga|ggc|ttg|ttt|gga| 720
|Val|Ser|Gly|Gly|Ser|Asp|Ile|Ile|Ile|Val|Gly|Arg|Gly|Leu|Phe|Gly|
|225| | | | |230| | | |235| | | |240| | |

|aag|gga|aga|gat|cca|aca|gtg|gaa|ggt|gag|cgt|tat|aga|aaa|gca|ggc| 768
|Lys|Gly|Arg|Asp|Pro|Thr|Val|Glu|Gly|Glu|Arg|Tyr|Arg|Lys|Ala|Gly|
| | | | |245| | | |250| | | |255| | | |

|tgg|gat|gct|tat|ctc|aag|aga|tgc|tca|gct|caa|taa| | | | | 804
|Trp|Asp|Ala|Tyr|Leu|Lys|Arg|Cys|Ser|Ala|Gln| | | | | |
| | | |260| | | |265| | | | | | | | |

<210> SEQ ID NO 36
<211> LENGTH: 267
<212> TYPE: PRT
<213> ORGANISM: Candida utilis

<400> SEQUENCE: 36

Met Val Thr Thr Leu Ser Tyr Thr Glu Arg Ala Ser Gln His Pro Ser
 1               5                  10                  15

Pro Leu Ala Lys Arg Leu Phe Ser Leu Met Glu Ser Lys Lys Thr Asn
            20                  25                  30

Leu Cys Ala Ser Val Asp Val Arg Thr Thr Glu Glu Leu Leu Lys Leu
        35                  40                  45

Val Asp Thr Leu Gly Pro Tyr Ile Cys Leu Leu Lys Thr His Ile Asp
    50                  55                  60

Ile Ile Asp Asp Phe Ser Met Glu Ser Thr Val Ala Pro Leu Leu Glu
65                  70                  75                  80

Leu Ser Lys Lys His Asn Phe Leu Ile Phe Glu Asp Arg Lys Phe Ala
                85                  90                  95

Asp Ile Gly Asn Thr Val Lys Ala Gln Tyr Ala Gly Gly Ala Phe Lys
            100                 105                 110

Ile Ala Gln Trp Ala Asp Ile Thr Asn Ala His Gly Val Thr Gly Ala
        115                 120                 125

Gly Ile Val Lys Gly Leu Lys Glu Ala Ala Gln Glu Thr Thr Asp Glu
    130                 135                 140

Pro Arg Gly Leu Leu Met Leu Ala Glu Leu Ser Ser Lys Gly Ser Leu
145                 150                 155                 160

Ala His Gly Thr Tyr Thr Glu Glu Thr Val Glu Ile Ala Lys Thr Asp
                165                 170                 175

Lys Asp Phe Cys Ile Gly Phe Ile Ala Gln Arg Asp Met Gly Gly Arg
            180                 185                 190

Glu Asp Gly Phe Asp Trp Ile Ile Met Thr Pro Gly Val Gly Leu Asp
        195                 200                 205

Asp Lys Gly Asp Ser Leu Gly Gln Gln Tyr Arg Thr Val Asp Glu Val
    210                 215                 220

Val Ser Gly Gly Ser Asp Ile Ile Ile Val Gly Arg Gly Leu Phe Gly
225                 230                 235                 240

Lys Gly Arg Asp Pro Thr Val Glu Gly Glu Arg Tyr Arg Lys Ala Gly
                245                 250                 255

Trp Asp Ala Tyr Leu Lys Arg Cys Ser Ala Gln
            260                 265

<210> SEQ ID NO 37
<211> LENGTH: 2086
<212> TYPE: DNA
<213> ORGANISM: Candida utilis

<400> SEQUENCE: 37

```
ggatccaatc gttgaaagtg atcaagctga ttacaaaagt aagtatgaaa agagccaatg      60
ttgagagtct caggaaccac atcgacttct tcgtgccatc ctcccacatt ctgaagccca     120
agaacccaca aatcatcaaa caccaacacg atgcggacgc caacccgagt tgtaacgcca     180
caaagtacgg gtacgaccct gttccaggag ggctcacgcc gcaatcaaca accaaagtcg     240
ccacgatcaa cgccagtatc aagtaaaaga agaatagcat ctccagtctt ccgatagctg     300
tgtacttcga tctgacgttg tagatgatga tgatcatgat cacgagggca ccaatgttga     360
caaaggcgtt accaatctgg aatatcacgg tattggcaac gtctatcgga cgggcgtagc     420
actcagggat gatcccttcg ttcaggtgcg tgaactgctc gttcgtcgtt gccttcacaa     480
cctggcacaa cgggagcggc gtgttgtggc atagcgagtt gaaatcaccg aatgccattg     540
tgttttatcg ttagggagac ctgtttgaag ctgacagcgg gatgaagatg aggaaggaga     600
gcacaacagc tgagcggaag tctctgtgat gcttggtgga ccgggtgtag gtggaatctc     660
cctggtgagc gtacttgcaa cggtgctcag cgacttcttc tcgagaggaa acgtaaacaa     720
agaggtttca atgttgatgt tgatgtgtat ttttgttaca aaagcagaaa ttgtaaacaa     780
aaaggtataa ttagggctct ggtgtaatga tgggcacgtg acgttaccgt gctggtcgat     840
tttagggcta ttggttcgcg tcccgctggt gtccgggtta gcgtgtcaat gtggcgcctc     900
ccgattatta cataagaaaa cacccaccca cgcaacacct ggtgtctgga tgttgacgct     960
ttgtatgcgt gtgtgtgttt tttcttccgt cttgttgggc cactctgcgc gagcgttggc    1020
gactcaccgg tgaaatttat cgaaaacttt caggctcagg cccttttcaa cactaccctt    1080
tgagatcaca tcaagcagta atcaaacaca atgggtatgt gggaaacgac gacgtgtgcg    1140
gtgtgtgaat gccattagtg ggatatgtgg tagtctcgag cgtggatatt atcgataggg    1200
atggtgcttg ttctatacgt cttgctggga aggaagaaag cgatgaagta tgtgggaaga    1260
aggggtggtt taagagagga agtagacatg taacaagtgt gttcagagaa caaggacgga    1320
aatatcacct atatgacgta cacatcacga actgctcctg gaggaagcga caagatgaat    1380
atcaacaggc atcatcatat ctctacaatg gctcgttccc aaagcacacg cacaaacaaa    1440
tccgagactt tgtactaac agctgtatct ctgacaaata gttaacgttc caagaccag     1500
aagaacctac tgtaagggta aggagtgcag aaagcacact caacacaagg ttacccagta    1560
caaggctggt aaggcttccc tctttgccca gggtaagcgt cgttatgacc gtaagcaatc    1620
cggttacggt ggtcaaacca agccagtttt ccacaaaaag gctaaaacca ccaagaaggt    1680
tgttttgcgt ttggagtgtg ttgtctgcaa gaccaaggcc caattggctt tgaagcgttg    1740
taagcacttc gagttgggtg gtgacaagaa gcaaaagggt caagctttgc aattctaagc    1800
ttaagacaat tgttgaaagt tttattatta tcactacact gtgttttga tgtcatctaa     1860
tgtaaaagcg tttatattac cacttggttc ggtatcctgt agaagaatac ggcctgtagc    1920
gtagcattcc cacaggagga tcacagcaac atagaccaaa caatgtcacg cacgggatc     1980
gaacgcggaa ccaaacctct ccctcctccc cctttcaccg cggttatttt gttatgggca    2040
cacacagggg aaggaaaaaa atgcacacac gcacaaaagc gagctc                   2086
```

<210> SEQ ID NO 38
<211> LENGTH: 688
<212> TYPE: DNA
<213> ORGANISM: Candida utilis
<220> FEATURE:
<221> NAME/KEY: CDS
<222> LOCATION: join(1..4, 372..685)

<400> SEQUENCE: 38

```
atg g gtatgtggga aacgacgacg tgtgcggtgt gtgaatgcca ttagtgggat         54
Met
  1 atgtggtagt ctcgagcgtg gatattatcg atagggatgg tgcttgttct atacgtcttg  114 ctgggaagga agaaagcgat gaagtatgtg ggaagaaggg gtggtttaag agaggaagta  174
gacatgtaac aagtgtgttc agagaacaag gacggaaata tcacctata tcacgaactg ctcctggagg aagcgacaag atgaatatca acaggcatca tcatatctct  294
acaatggctc gttcccaaag cacacgcaca aacaaatccg agactttg gtatctctga caaatag tt aac gtt cca aag acc aga aga acc tac tgt      403
                Val Asn Val Pro Lys Thr Arg Arg Thr Tyr Cys
                  5                  10 aag ggt aag gag tgc aga aag cac act caa cac aag gtt acc cag tac    451
Lys Gly Lys Glu Cys Arg Lys His Thr Gln His Lys Val Thr Gln Tyr
 15                  20                  25 aag gct ggt aag gct tcc ctc ttt gcc cag ggt aag cgt cgt tat gac    499
Lys Ala Gly Lys Ala Ser Leu Phe Ala Gln Gly Lys Arg Arg Tyr Asp
 30                  35                  40 cgt aag caa tcc ggt tac ggt ggt caa acc aag cca gtt ttc cac aaa    547
Arg Lys Gln Ser Gly Tyr Gly Gly Gln Thr Lys Pro Val Phe His Lys
 45                  50                  55                  60 aag gct aaa acc acc aag aag gtt gtt ttg cgt ttg gag tgt gtt gtc    595
Lys Ala Lys Thr Thr Lys Lys Val Val Leu Arg Leu Glu Cys Val Val
                 65                  70                  75 tgc aag acc aag gcc caa ttg gct ttg aag cgt tgt aag cac ttc gag    643
Cys Lys Thr Lys Ala Gln Leu Ala Leu Lys Arg Cys Lys His Phe Glu
                 80                  85                  90 ttg ggt ggt gac aag aag caa aag ggt caa gct ttg caa ttc              685
Leu Gly Gly Asp Lys Lys Gln Lys Gly Gln Ala Leu Gln Phe
                 95                 100                 105 taa                                                                  688
```

<210> SEQ ID NO 39
<211> LENGTH: 106
<212> TYPE: PRT
<213> ORGANISM: Candida utilis

<400> SEQUENCE: 39

```
Met Val Asn Val Pro Lys Thr Arg Arg Thr Tyr Cys Lys Gly Lys Glu
  1               5                  10                  15

Cys Arg Lys His Thr Gln His Lys Val Thr Gln Tyr Lys Ala Gly Lys
                 20                  25                  30

Ala Ser Leu Phe Ala Gln Gly Lys Arg Arg Tyr Asp Arg Lys Gln Ser
         35                  40                  45

Gly Tyr Gly Gly Gln Thr Lys Pro Val Phe His Lys Lys Ala Lys Thr
     50                  55                  60

Thr Lys Lys Val Val Leu Arg Leu Glu Cys Val Val Cys Lys Thr Lys
 65                  70                  75                  80

Ala Gln Leu Ala Leu Lys Arg Cys Lys His Phe Glu Leu Gly Gly Asp
                 85                  90                  95

Lys Lys Gln Lys Gly Gln Ala Leu Gln Phe
            100                 105
```

<210> SEQ ID NO 40
<211> LENGTH: 1113
<212> TYPE: DNA
<213> ORGANISM: Candida utilis -continued

```
<400> SEQUENCE: 40
ggatccaatc gttgaaagtg atcaagctga ttacaaaagt aagtatgaaa agagccaatg      60
ttgagagtct caggaaccac atcgacttct tcgtgccatc ctcccacatt ctgaagccca     120
agaacccaca aatcatcaaa caccaacacg atgcggacgc caacccgagt tgtaacgcca     180
caaagtacgg gtacgaccct gttccaggag ggctcacgcc gcaatcaaca accaaagtcg     240
ccacgatcaa cgccagtatc aagtaaaaga agaatagcat ctccagtctt ccgatagctg     300
tgtacttcga tctgacgttg tagatgatga tgatcatgat cacgagggca ccaatgttga     360
caaaggcgtt accaatctgg aatatcacgg tattggcaac gtctatcgga cgggcgtagc     420
actcagggat gatcccttcg ttcaggtgcg tgaactgctc gttcgtcgtt gccttcacaa     480
cctggcacaa cgggagcggc gtgttgtggc atagcgagtt gaaatcaccg aatgccattg     540
tgttttatcg ttagggagac ctgtttgaag ctgacagcgg gatgaagatg aggaaggaga     600
gcacaacagc tgagcggaag tctctgtgat gcttggtgga ccgggtgtag gtggaatctc     660
cctggtgagc gtacttgcaa cggtgctcag cgacttcttc tcgagaggaa acgtaaacaa     720
agaggtttca atgttgatgt tgatgtgtat ttttgttaca aaagcagaaa ttgtaaacaa     780
aaaggtataa ttagggctct ggtgtaatga tgggcacgtg acgttaccgt gctggtcgat     840
tttagggcta ttggttcgcg tcccgctggt gtccgggtta gcgtgtcaat gtggcgcctc     900
ccgattatta cataagaaaa cacccaccca cgcaacacct ggtgtctgga tgttgacgct     960
ttgtatgcgt gtgtgtgttt tttcttccgt cttgttgggc cactctgcgc gagcgttggc    1020
gactcaccgg tgaaatttat cgaaaacttt caggctcagg cccttttcaa cactacccct    1080
tgagatcaca tcaagcagta atcaaacaca atg                                 1113

<210> SEQ ID NO 41
<211> LENGTH: 90
<212> TYPE: DNA
<213> ORGANISM: Artificial Sequence
<220> FEATURE:
<223> OTHER INFORMATION: Description of Artificial Sequence: Primer

<400> SEQUENCE: 41
ggtctagata tgaccttcgc ttacaagatc gatggtaacg aggttatctt cactttgtgg      60
gctccatacc aaaagtccgt taagttgaag                                       90

<210> SEQ ID NO 42
<211> LENGTH: 89
<212> TYPE: DNA
<213> ORGANISM: Artificial Sequence
<220> FEATURE:
<223> OTHER INFORMATION: Description of Artificial Sequence: Primer

<400> SEQUENCE: 42
ataccaaaag tccgttaagt tgaaggtctt ggagaagggt ttgtacgaga tggagagaga      60
cgagaagggt tacttcacca tcactttga                                        89

<210> SEQ ID NO 43
<211> LENGTH: 90
<212> TYPE: DNA
<213> ORGANISM: Artificial Sequence
<220> FEATURE:
<223> OTHER INFORMATION: Description of Artificial Sequence: Primer

<400> SEQUENCE: 43
ggccttggac tcttggatga tttgagatgg accgtggaca ccctctggtt ggtatctgga      60
```
agctgggtct gggatctcgg aagcatcgtc                                              90

<210> SEQ ID NO 44
<211> LENGTH: 87
<212> TYPE: DNA
<213> ORGANISM: Artificial Sequence
<220> FEATURE:
<223> OTHER INFORMATION: Description of Artificial Sequence: Primer

<400> SEQUENCE: 44
ggtctgggat ctcggaagca tcgtccaaaa cgtacttgta tctgtctctg accttgacgt         60
tgttcaaagt gatggtgaag taaccct                                             87

<210> SEQ ID NO 45
<211> LENGTH: 100
<212> TYPE: DNA
<213> ORGANISM: Artificial Sequence
<220> FEATURE:
<223> OTHER INFORMATION: Description of Artificial Sequence: Primer

<400> SEQUENCE: 45
aaccaaggag ttcaacaacg agaccttctt gaagaaggag gacttgatca tctacgagat         60
ccacgtcggt actttcaccc cagagggtac tttcgagggt                              100

<210> SEQ ID NO 46
<211> LENGTH: 100
<212> TYPE: DNA
<213> ORGANISM: Artificial Sequence
<220> FEATURE:
<223> OTHER INFORMATION: Description of Artificial Sequence: Primer

<400> SEQUENCE: 46
ccccagaggg tactttcgag ggtgtcatca gaaagttgga ctacttgaag gatttgggta         60
tcaccgctat cgagatcatg ccaatcgctc aattcccagg                              100

<210> SEQ ID NO 47
<211> LENGTH: 100
<212> TYPE: DNA
<213> ORGANISM: Artificial Sequence
<220> FEATURE:
<223> OTHER INFORMATION: Description of Artificial Sequence: Primer

<400> SEQUENCE: 47
aagtagacaa cgtccaagat aacacccaaa cccttcttgt gagcctcatc aaccaacttt         60
ctgaaaccct ctggaccacc gtaggagttt tggacagcgt                              100

<210> SEQ ID NO 48
<211> LENGTH: 100
<212> TYPE: DNA
<213> ORGANISM: Artificial Sequence
<220> FEATURE:
<223> OTHER INFORMATION: Description of Artificial Sequence: Primer

<400> SEQUENCE: 48
accgtaggag ttttggacag cgtacaagta aacaccatcg taccccagt ctctcttacc         60 tgggaattga gcgattggca tgatctcgat agcggtgata                              100

<210> SEQ ID NO 49
<211> LENGTH: 74
<212> TYPE: DNA
<213> ORGANISM: Artificial Sequence
<220> FEATURE:

```
<223> OTHER INFORMATION: Description of Artificial Sequence: Primer

<400> SEQUENCE: 49
atgtctacaa ccatgttggt ccagagggta actacatggt taagttgggt ccatacttca      60
gtcaaaagta caag                                                       74

<210> SEQ ID NO 50
<211> LENGTH: 80
<212> TYPE: DNA
<213> ORGANISM: Artificial Sequence
<220> FEATURE:
<223> OTHER INFORMATION: Description of Artificial Sequence: Primer

<400> SEQUENCE: 50
catacttcag tcaaaagtac aagaccccat ggggtttgac cttcaacttc gacgacgctg      60
agtccgatga ggtcagaaag                                                 80

<210> SEQ ID NO 51
<211> LENGTH: 75
<212> TYPE: DNA
<213> ORGANISM: Artificial Sequence
<220> FEATURE:
<223> OTHER INFORMATION: Description of Artificial Sequence: Primer

<400> SEQUENCE: 51
agctcgagga tgtgctttgg agaggtgtcg atgatagcgt ggacagcgtc aatctgaaa      60 ccatcaacgt tgtac                                                      75

<210> SEQ ID NO 52
<211> LENGTH: 73
<212> TYPE: DNA
<213> ORGANISM: Artificial Sequence
<220> FEATURE:
<223> OTHER INFORMATION: Description of Artificial Sequence: Primer

<400> SEQUENCE: 52
aaccatcaac gttgtactcc ttgatccagt attcaacgtt ctccaagatg aactttctga     60
cctcatcgga ctc                                                        73

<210> SEQ ID NO 53
<211> LENGTH: 69
<212> TYPE: DNA
<213> ORGANISM: Artificial Sequence
<220> FEATURE:
<223> OTHER INFORMATION: Description of Artificial Sequence: Primer

<400> SEQUENCE: 53
tcctcgagga gatcgctgat gttgtccaca agtacaacag aatcgttatc gctgagtccg     60
acttgaacg                                                             69

<210> SEQ ID NO 54
<211> LENGTH: 68
<212> TYPE: DNA
<213> ORGANISM: Artificial Sequence
<220> FEATURE:
<223> OTHER INFORMATION: Description of Artificial Sequence: Primer

<400> SEQUENCE: 54
gctgagtccg acttgaacga cccacgtgtt gttaacccaa aggagaagtg tggttacaac     60
atcgacgc                                                              68
```

```
<210> SEQ ID NO 55
<211> LENGTH: 69
<212> TYPE: DNA
<213> ORGANISM: Artificial Sequence
<220> FEATURE:
<223> OTHER INFORMATION: Description of Artificial Sequence: Primer

<400> SEQUENCE: 55
tggatatcgt ccaagttacc gaagtcagtg tagtaacctt gtctctcacc ggtcaagtaa     60
gcgtggata                                                             69

<210> SEQ ID NO 56
<211> LENGTH: 67
<212> TYPE: DNA
<213> ORGANISM: Artificial Sequence
<220> FEATURE:
<223> OTHER INFORMATION: Description of Artificial Sequence: Primer

<400> SEQUENCE: 56
ggtcaagtaa gcgtggatag agtggtggaa atcgtcaacc cattgagcgt cgatgttgta     60
accacac                                                               67

<210> SEQ ID NO 57
<211> LENGTH: 100
<212> TYPE: DNA
<213> ORGANISM: Artificial Sequence
<220> FEATURE:
<223> OTHER INFORMATION: Description of Artificial Sequence: Primer

<400> SEQUENCE: 57
cagatatcgt taagtcctac aaggacgtct tcgtttacga tggtaagtac tccaacttca     60
gaagaaagac ccacggtgag ccagttggtg agttggatgg                          100

<210> SEQ ID NO 58
<211> LENGTH: 100
<212> TYPE: DNA
<213> ORGANISM: Artificial Sequence
<220> FEATURE:
<223> OTHER INFORMATION: Description of Artificial Sequence: Primer

<400> SEQUENCE: 58
aagtcgacga gcttaatgat tctctcaccc ttacctctgt taccgacttg atcgtggttt     60
tggatgtaaa cgacgaagtt acaaccatcc aactcaccaa                          100

<210> SEQ ID NO 59
<211> LENGTH: 76
<212> TYPE: DNA
<213> ORGANISM: Artificial Sequence
<220> FEATURE:
<223> OTHER INFORMATION: Description of Artificial Sequence: Primer

<400> SEQUENCE: 59
tcgtcgacag agagtcctac aagatcgctg ctgctttgta cttgttgtct ccatacatcc     60
caatgatctt catggg                                                     76

<210> SEQ ID NO 60
<211> LENGTH: 76
<212> TYPE: DNA
<213> ORGANISM: Artificial Sequence
<220> FEATURE:
<223> OTHER INFORMATION: Description of Artificial Sequence: Primer

<400> SEQUENCE: 60
```

```
catcccaatg atcttcatgg gtgaggagta cggtgaggag aacccattct acttcttctc      60
tgacttctcc gactcc                                                     76

<210> SEQ ID NO 61
<211> LENGTH: 75
<212> TYPE: DNA
<213> ORGANISM: Artificial Sequence
<220> FEATURE:
<223> OTHER INFORMATION: Description of Artificial Sequence: Primer

<400> SEQUENCE: 61
tcatcgatct tccaagacaa cttggaagcg ttgaaggtgg actcgtcttg tggatcagtg     60
tcttgaccgt tctcc                                                      75

<210> SEQ ID NO 62
<211> LENGTH: 77
<212> TYPE: DNA
<213> ORGANISM: Artificial Sequence
<220> FEATURE:
<223> OTHER INFORMATION: Description of Artificial Sequence: Primer

<400> SEQUENCE: 62
cagtgtcttg accgttctcc ttctttctac cctctctaac accttggatc aacttggagt     60
aggagaagtc agagaag                                                    77

<210> SEQ ID NO 63
<211> LENGTH: 82
<212> TYPE: DNA
<213> ORGANISM: Artificial Sequence
<220> FEATURE:
<223> OTHER INFORMATION: Description of Artificial Sequence: Primer

<400> SEQUENCE: 63
agatcgatga ggagattttc agtttctaca agatccttat caagatgaga aaggagttgt     60
ccatcgcttg tgacagaaga gt                                              82

<210> SEQ ID NO 64
<211> LENGTH: 91
<212> TYPE: DNA
<213> ORGANISM: Artificial Sequence
<220> FEATURE:
<223> OTHER INFORMATION: Description of Artificial Sequence: Primer

<400> SEQUENCE: 64
ccatcgcttg tgacagaaga gtcaacgttg tcaacggtga gaactggttg atcatcaagg     60
gtagagaata cttctccttg tacgtcttca g                                    91

<210> SEQ ID NO 65
<211> LENGTH: 80
<212> TYPE: DNA
<213> ORGANISM: Artificial Sequence
<220> FEATURE:
<223> OTHER INFORMATION: Description of Artificial Sequence: Primer

<400> SEQUENCE: 65
cgagatctgc tacaacttgt acaaagcgaa acccttgtcg aactcgtact taccctcctc     60
gatgtgttgt gggaaactgt                                                 80

<210> SEQ ID NO 66
<211> LENGTH: 92
<212> TYPE: DNA
<213> ORGANISM: Artificial Sequence
```

```
<220> FEATURE:
<223> OTHER INFORMATION: Description of Artificial Sequence: Primer

<400> SEQUENCE: 66
cgatgtgttg tgggaaactg ttgttggaag acaacaacaa ggtaccactg tacttaacct      60
cgatggagga cttactgaag acgtacaagg ag                                    92
```

YEAST VECTOR AND METHOD OF PRODUCING PROTEINS USING THE SAME

This application is a divisional of application Ser. No. 09/242,690 filed Feb. 23, 1999, now U.S. Pat. No. 6,284,536, which claims the benefit of National Stage Application No. PCT/JP97/02924 filed Aug. 22, 1997, all of which are incorporated by reference herein in their entirety including all figures, tables, and drawings.

BACKGROUND OF THE INVENTION

1. Field of the Invention

The present invention relates to a vector which is integrated into the chromosome of yeast, specifically *Candida utilis*, with a high number of copies and which can be stably maintained even under nonselective culture conditions. The present invention also relates to heterologous gene expression, specifically the high-level expression of a single chain monellin and amylase, using said vector, and further relates to a method for isolating and purifying a single-chain monellin from single-chain monellin-producing recombinant yeast cells.

2. Background Art

In order to prepare gene products in large quantities using recombinant DNA procedures, it is necessary not only to select an appropriate host but also to increase the number of gene transcripts, to improve the translation efficiency, and to improve the stability of proteins produced in the various steps of gene expression. In order to increase the number of gene transcript for high-level production of gene products, it is necessary to use a highly effective transcription promoter and it is also important to increase the number of copies of the gene-expression unit which consists of the transcription promoter/terminator sequence and the gene to be expressed, thereby increasing the number of transcripts as a whole. Furthermore, for industrial scale production, it is extremely important that the gene-expression unit be stably maintained in the microbial cells. Plasmid vectors are at a disadvantage in this regard and generally stabilized by integration into a chromosome.

Regarding several yeast species other than *C. utilis*, it has been recently reported that dozens of copies of a vector could be integrated into the ribosomal RNA gene (rDNA) regions by using the vector carrying a transformation marker gene in which the promoter region was trancated to reduce the expression level (Lopes T. S. et al., Gene, 79, 199–206, 1989; Bergkamp R. J. M. et al., Curr. Genet., 21, 365–370, 1992; Le Dall M. T. et al., Curr. Genet., 26, 38–44, 1994).

However, it has been shown that to achieve high-copy-number integration into the chromosome, it is necessary to integrate the vector into the ribosomal RNA gene regions; otherwise, a large number of copies will not be obtained when the vector is integrated into other gene loci (Lopes T. S. et al., Gene, 105, 83–90, 1991). It has further been reported that the introduced genes might not be sustained due to recombination between their repetitive sequences because the integrated vectors existed in a tandem form in the chromosome (Lopes T. S. et al., Yeast, 12, 467–477, 1996). In particular, when microbial cells are cultured under nonselective conditions or microbial growth is slow (for example, when the expression product is present in abundance in the microbial cells), successive cultivation for generations will result in an increase in the ratio of cells without vectors. Accordingly, when recombinant yeasts are cultured under nonselective conditions (particularly in a large-scale culture), stable maintenance of the integrated vectors is of extreme importance. It has been reported that an expression unit integrated into the chromosome was stabilized by shortening the size of vector DNA (Lopes T. S. et al., Yeast, 12, 467–477, 1996).

*Candida utilis*, a yeast which efficiently assimilates pentoses such as xylose, has been approved to use as a food additive by the Food and Drug Administration (FDA) along with *Saccharomyces cerevisiae* and *S. fragilis*. A transformation system for *Candida utilis* using homologous recombination was developed recently, and heterologous protein production was reported (WO/95/32289). However, further improvements as to high-copy-number introduction of the vector into the chromosome and stabilization of the expression units are still to be achieved.

Sweet proteins are expected to be extensively used as a highly safe, low calorie sweetener, food additive, or sweetening agent in foods, drugs and the like, and even animal feed. Examples of such sweet proteins include monellin and thaumatin.

Thaumatin is a protein which can increase the palatability of food (i.e., enhance flavor and aroma) and is extracted from seed coats of the fruit of plant, *Thaumatococcus daniellii* Benth. However, although it is commercially available, the industrial use of plant-derived thaumatin is extremely limited because of the scarce availability of fruit for extraction. Although the production of thaumatin in a number of microbial hosts has been tried to date, published reports would indicate that expression of the protein was extremely difficult, and the protein so obtained was of minimal sweetness (Zemanek E. C. and Wasserman B. P., Critical Reviews in Food Science and Nutrition, 35, 455–466, 1995).

Monellin, a protein found in the fruit of the tropical plant *Dioscoreophyllum cumminsii*, is more than 2,000 times sweeter than sucrose on a weight basis, and its amino acid sequence is known. This protein comprises two nonhomologous subunits, A and B, and its tertiary structure has been reported (Hudson G. et al., Biochem. Biophys. Res. Comm., 71, 212–220, 1976; Ogata C. et al., Nature, 328, 739–742, 1987; van der Wel H., FEBS Letters, 21, 88–90, 1972; Morris J. A. et al., Biochim. Biophys. Acta. 261, 114–122, 1972; Bohak Z. et al., Biochim. Biophys. Acta., 427, 153–170, 1976; Frank G. Hoppe-Seyler's Z. Physiol. Chem., 357, 585–592, 1976). Natural monellin rapidly loses its sweetness at high temperatures at acidic pHs. Attempts are under way to produce a more thermally stable protein which retains its sweetness by linking the two chains comprising monellin, namely, linking the N-terminal of the subunit A with the C-terminal of the subunit B to make a single polypeptide chain (Japanese Patent 1990/504028; Japanese Patent Laid-open 1993/70494; Kim S -H. et al., Protein Engineering, 2, 571–575, 1989). This single-chain monellin having excellent properties is being expected for use in food as a low calorie, highly stable protein sweetener, a food additive in place of conventional sweetening agents, or a sweetening agent.

However, as long as the present inventors know, the large-scale microbial production of monellin has not been reported.

SUMMARY OF THE INVENTION

It has been shown that, when the cycloheximide-resistance L41 gene is used as a marker gene in *C. utilis*, the number of integrated vectors (copies) into the host by homologous recombination is generally about 3 to 10 (at most about 20). The present inventors have now found that the number of the copies increases to as much as 20 to 90 when the promoter which is operably linked to the marker gene is shortened.

It has also been known that the number of copies in yeast cells other than *C. utilis* could be increased only by targeting rDNA sequences for the integration. Even when rDNA sequences is targeted for the integration, the expression units are inevitably excised. The present inventors have now found that, in addition to shortening the promoter linked to the marker gene, targeting of the sequence homologous to the chromosomal DNA at gene loci other than rDNA sequences would not only further increase the number of the copies (exceeding the number achieved with rDNA target sequences), but would also stabilize the expression units on the chromosome.

The present inventors have also found that proteins (in particular, single-chain monellin and amylase) can be expressed abundantly by using the vector and that when the extract obtained from single-chain monellin-producing cells is treated with heat and/or acid, monellin remains in solution while most undesirable proteins derived from the yeast will precipitate.

The present inventors have further found that the frequency of usage of codons in the amylase gene (derived from the thermophilic bacteria *Sulfolobales solfataricus*) for expression in *C. utilis* differs markedly from that in the structural gene of glyceraldehyde-3-phosphate dehydrogenase (GAP), which is one of the proteins best expressed in *C. utilis*. Moreover, modification of the amylase gene sequence markedly increases the level of amylase expression. The present invention is based on these findings.

Accordingly, an object of the present invention is to provide a vector which can be integrated in a high number of copies into the yeast chromosome. Another object of the present invention is to provide a modified vector which can be integrated in a high number of copies into a yeast chromosome and of which expression units maintain stably on the chromosome.

Another object of the present invention is to provide a method for transformation using said vector, a host transformed by said vector, a method of producing proteins by culturing said host, and a method of purifying the single-chain monellin.

Furthermore, another object of the present invention is to provide a shortened promoter to improve the number and stability of the vector to be integrated, and an amylase gene modified to be highly expressed in *C. utilis*.

The vector according to the present invention is a vector which comprises a marker gene for selecting transformants, a shortened promoter sequence which is operably linked to the marker gene and a sequence homologous to the chromosomal DNA of *C. utilis* ("homologous DNA sequence"), and optionally a heterologous gene or a gene derived from *C. utilis*, wherein the vector is linearized by cleaving within said homologous DNA sequence or at both ends of the homologous DNA sequence with restriction enzymes, and wherein the heterologous gene or the gene derived from *C. utilis* can be integrated into the chromosomal DNA of *C. utilis* by homologous recombination.

The vector according to the present invention is a vector which comprises a gene conferring cycloheximide-resistance, a heterologous gene or a gene derived from *C. utilis*, and optionally a promoter sequence and a terminator sequence which are operably linked to the heterologous gene or the gene derived from *C. utilis*, wherein the heterologous gene or the gene derived from *C. utilis*, and optionally the DNA sequence containing the promoter and the terminator are flanked at both ends by the gene conferring cycloheximide-resistance, and wherein the vector is linearized by cleaving within the gene sequence conferring cycloheximide resistance or at both ends of said gene sequence with restriction enzymes, and the heterologous gene or the gene derived from *C. utilis* can be integrated into the chromosomal DNA of *C. utilis* by homologous recombination.

BRIEF DESCRIPTION OF DRAWINGS

FIG. 2 shows the structures of ribosomal DNAs, the strategy for DNA sequence determination, and the structures of subcloned plasmids.

FIG. 2(*a*) shows structures of plasmids pCRE1, pCRE2, pCRE3, pCRX1, pCRX2, pCRX3, and pCRX4, and FIG. 2(*b*) shows the restriction enzyme cleavage map of an approximately 13.5 kb DNA fragment containing ribosomal DNAs of *C. utilis*.

FIG. 5 shows the sequence (SEQ ID NO: 34) of a DNA fragment containing the URA3 gene.

FIG. 6 shows the amino acid sequence (SEQ ID NO: 36) deduced from the DNA sequence of the URA3 gene and the sequence of the DNA encoding for the amino acid sequence.

FIG. 7 shows the amino acid sequence (SEQ ID NO: 36) deduced from the DNA sequence of the URA3 gene and the sequence (SEQ ID NO: 35) of the DNA encoding for the amino acid sequence (continued from FIG. 6).

FIG. 9 shows the sequence of (SEQ ID NO: 37) a DNA fragment containing the L41 gene.

FIG. 10 shows the amino acid sequence (SEQ ID NO: 39) deduced from the DNA sequence of the L41 gene and the sequence (SEQ ID NO: 38) of DNA coding for the amino acid sequence.

FIGS. 13*a*–13*b* shows the structure of plasmid pCLRE2.

FIG. 13*b* shows locations of the 5' terminal in the cycloheximide-resistance L41 gene promoter (SEQ ID NO: 40) of plasmids pCLRE11, pCLRE15, pCLRE16, pCLRE17, pCLRE18, and pCLRE19.

FIG. 14 shows results of Southern blot analysis of transformants with plasmids pCLRE11, pCLRE15, pCLRE16 and pCLRE17 (photographs of electrophoresis) and the number of copies of integrated vectors.

FIG. 15 shows the construction of plasmids pCLR215, pCLR216 and pCLR217.

FIG. 20 shows the construction of plasmids pCLRM215, pCLRM216, pCLRM217, pRM10, pRM11, pUM10, and pUM11.

FIG. 21 (1) is a photograph showing results of the analysis of soluble proteins of C. utilis transformants with plasmids pCLRE4, pCLRM216, pRM11, and pUM11 using SDS-polyacrylamide gel electrophoresis.

FIG. 21 (2) is a photograph showing results of the analysis of soluble proteins of S. cerevisiae transformants with plasmid pCTMNY1 using SDS-PAGE.

FIG. 24 shows primers used in the synthesis of segments A-1 (SEQ ID NOS: 41–44) and A-2 (SEQ ID NOS: 45–48) of the modified amylase gene.

FIG. 25 shows primers used in the synthesis of segments A-3 (SEQ ID NOS: 49–52) and A-4 (SEQ ID NOS: 53–56) of the modified amylase gene. FIG. 26 shows primers used in the synthesis of segments A-5, (SEQ ID NOS: 57–58) A-6, (SEQ ID NOS: 59–62) and A-7 (SEQ ID NOS: 63–66) of the modified amylase gene.

DETAILED DESCRIPTION OF THE INVENTION

Shortened Promoter

Figure 1:
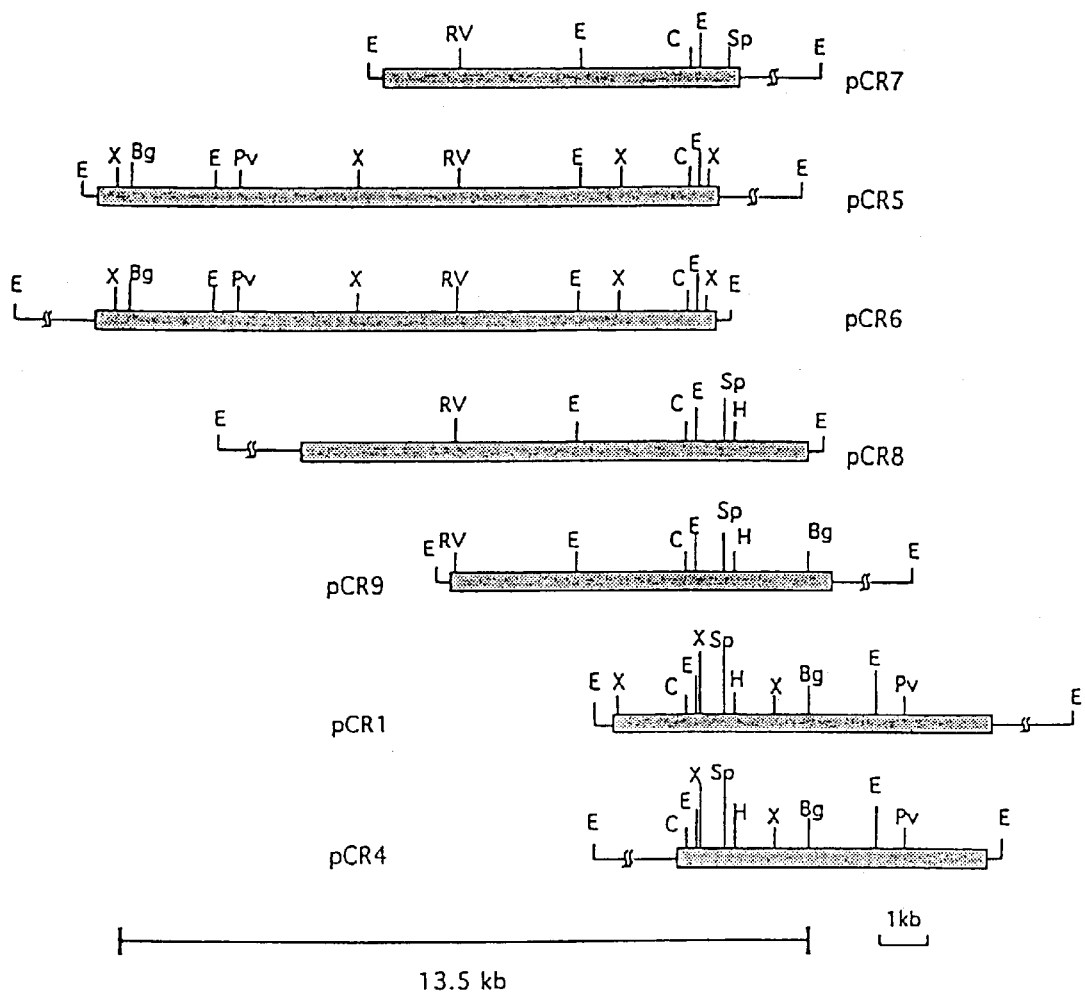
FIG. 1 shows restriction enzyme cleavage maps of plasmids containing ribosomal DNAs.

The term "shortened promoter" as used herein refers to a promoter trancated at its 5' side, which decreases the transformation frequency of the vector by decreasing the level of expression of the marker gene but increases the number of copies of the vector in the host cells.

As shown in the Examples, a vector having a marker gene to be expressed by a promoter shortened by trancating its 5'-end region is characterized in that its transformation frequency is reduced by decreasing the level of expression of the marker gene but is present in a higher copy number in the transformed host cells, as compared to a vector ligated with a marker gene to be expressed by a promoter of normal length.

The shortened promoter in the present invention can be selected from those which can be operably linked to a marker gene usable in C. utilis.

Examples of such promoters include those derived from the L41 gene of C. utilis, the phosphoglycerate acid kinase (PGK) gene, the glyceraldehyde-3-phosphoric acid hydrogenase (GAP) gene, and the plasma membrane proton ATPase (PMA) gene.

When the promoter is obtained from the L41 gene, the shortened promoter sequence contains the DNA sequence X to 192 of SEQ ID NO. 1. X herein refers to an integer from 1 to 111. The DNA sequences of SEQ ID NO. 2 and NO. 3 are those obtained by trancating the 5' end sequence of the DNA sequence of SEQ ID NO. 1.

The shortened promoter derived from the L41 gene is a novel DNA sequence. Accordingly, another aspect of the present invention provides the DNA sequence X to 192 (wherein X represents an integer from 1 to 111) of SEQ ID NO. 1 and the DNA sequences of SEQ ID NO.2 and NO. 3. These sequences are useful as the promoter sequence for a selective marker gene of vectors for chromosomal integration.

In the present invention, the shortened promoter is operably linked to the marker gene. In certain cases, a terminator sequence may be added downstream of the marker gene.

Homologous DNA Sequence

The vector according to the present invention has a homologous DNA sequence for homologous recombination into a host chromosome.

Examples of such homologous DNA sequences in the present invention include the rDNA (ribosomal DNA) sequence, the URA3 gene sequence, the L41 gene sequence, the PGK gene sequence, the GAP gene sequence, the PMA gene sequence, and partial DNA sequences thereof. A sequence derived from the chromosome of C. utilis is preferable. Genes from C. utilis other than the genes described above can similarly be used. A heterologous gene can be integrated at any site on the chromosome depending on a function of the sequence being used. The term "rDNA sequence" as used herein also refers to a series of rRNA genes.

According to the present invention, a gene sequence other than the rDNA sequence from C. utilis is preferably used as a homologous DNA sequence. It is advantageous to use a gene sequence other than the rDNA sequence because it not only increases the number of vector copies but also remarkably improves the stability of the vector on the chromosome. Examples of such a sequence include the URA3 gene sequence, the L41 gene sequence, the PGK gene sequence, the GAP gene sequence, and the PMA gene sequence derived from C. utilis, and partial DNA sequences thereof. Genes other than the rDNA sequence from C. utilis can also be used.

This vector is linearized for use by digestion at an appropriate restriction enzyme cleavage site in a homologous DNA sequence in the vector (plasmid DNA). This enables a plasmid DNA fragment to be integrated into the C. utilis chromosome by homologous recombination.

In a preferred embodiment of the present invention, within a vector, a DNA sequence comprising a marker gene and a heterologous gene is flanked at both ends by the homologous DNA sequence described above. According to this embodiment, the homologous DNA sequence of the vector DNA is cleaved at both ends by restriction enzymes to obtain a DNA fragment containing the marker gene and the heterologous gene having the homologous DNA sequence at both ends. The DNA fragment thus obtained can also be integrated into the C. utilis chromosomal DNA by homologous recombination. It is advantageous from a safety point of view to use a vector which is linearized in this manner by cleaving at the restriction enzyme cleavage sites corresponding to both ends of the homologous sequence because no DNA derived from the plasmid is integrated into the chromosome (namely, there is no possibility to produce unknown gene products derived from bacteria).

The expression "a DNA fragment (or sequence) is integrated in the C. utilis chromosome by homologous recombination" as used herein means that as long as the DNA fragment is integrated into the C. utilis chromosome, its actual mode of integration is not restricted, but at least, the following modes are included:

(1) Homologous recombination occurs between the DNA sequence of the C. utilis chromosome and the homologous DNA sequence at both ends of the DNA fragment and the DNA fragment is "inserted" at the cleaved site.
(2) Homologous recombination occurs between the DNA sequence of the C. utilis chromosome and the homologous DNA sequence at both ends of the DNA fragment such that the vector DNA fragment is "substituted" with a part of the C. utilis chromosome.

In mode (2), stability of the integrated DNA fragment in the chromosome is further improved because no repetitive sequence of the target sequence is formed before or after the inserted DNA fragment.

Marker Gene

According to the present invention, the marker gene can be a drug-resistance gene. Examples of drug resistance genes include those which can select C. utilis transformants, such as a gene conferring cycloheximide resistance (e.g., the modified cycloheximide-resistance L41 gene), a gene conferring antibiotic G418 resistance (e.g., the aminoglycoside-3'-phosphotransferase (APT) gene derived from bacterial transposon Tn903), a gene conferring hygromycin B resistance (e.g., the hygromycin B phosphotransferase (HPT) gene derived from an E. coli plasmid).

The L41 gene codes for the ribosomal protein L41 which is sensitive to cycloheximide. The modified cycloheximide-resistance L41 gene is a gene in which Pro at position 56 of the amino acid sequence of L41 is substituted with Gln. L41 cycloheximide resistance is conferred by this substitution (WO/95/32289).

In addition to the G418-resistance gene and hygromycin B phosphotransferase gene, examples of drug resistance genes derived from bacteria which can be used as a selective marker for transformants include antibiotic-resistance genes, such as the chloramphenicol acetyl transferase gene (chloramphenicol resistance) (Hadfield, C. et al., Gene, 45, 149–158, 1986), the blasticidin deaminase gene (blasticidin resistance) (Izumi, M. et al., Exp. Cell Res., 197, 229–233, 1991), and the phleomycin-resistance gene (Wenzel, T. J. et al., Yeast, 8, 667–668, 1992). Other usable known drug-resistance genes are the dehydrofolate reductase gene (methotrexate resistance) (Miyajima, A. et al., Mol. Cell Biol., 4, 407–414, 1984), sulfometuronmethyl-resistance gene, a dominant gene derived from yeast (Casey, G. P. et al., J. Inst. Brew., 94, 93–97, 1988), the CUP1 gene (copper resistance) (Henderson, R. C. A. et al., Current Genet., 9, 133–138, 1985), and the CYH2 gene (cycloheximide resistance) (Delgado, M. et al., EBC Congress, 23, 281–288, 1991).

Heterologous Genes and Genes Derived from C. utilis

According to one embodiment of the present invention, a heterologous gene or a gene derived from C. utilis ("structural gene") is ligated into the vector according to the present invention to construct a vector carrying the structural gene. These structural genes can be stably integrated into the C. utilis chromosome by transforming C. utilis using this vector. The protein encoded by a structural gene can be produced using C. utilis by culturing a transformant thus obtained in an appropriate medium, isolating the expressed product of the structural gene from the culture, and purifying it by a method appropriate for the expressed product. A method for expressing the structural gene in C. utilis is provided. The term "heterologous gene" as used herein refers to a gene which does not exist in the host C. utilis chromosome, or a partial DNA thereof.

The structural gene is preferably combined with a regulatory region which independently controls the expression of the gene, or it can be expressed under a regulatory region of the gene itself which is disrupted during transformation. Such sequences are needed to function in C. utilis and preferable examples of such sequences include the promoter sequences and the terminator sequences of the PGK gene, GAP gene, and the PMA gene according to the present invention as mentioned after.

As shown in Examples, heterologous genes such as the single-chain monellin gene, the GIF gene and the amylase gene were successfully expressed using the promoter sequence and the terminator sequence of the GAP gene, in accordance with the present invention.

Furthermore, it will be appreciated by those skilled in the art that structural genes (for example, genes coding for albumin, α- or β-globulin, factor VIII, factor IX, fibronectin, α-1-antitrypsin, interleukin, interferon, G-CSF, GM-CSF, PDGF, EGF, FGF, erythropoietin, thrombopoietin, insulin, antigen polypeptides derived from viruses for vaccine production, proteins having immune suppression activity (e.g., glycosylation inhibiting factor (GIF)), chymosin, amylase, lipase, cellulose, protease and pectinase) can be expressed using the promoter and terminator sequences of the phosphoglycerate kinase gene, the promoter and terminator sequences of the glyceraldehyde-3-phosphate dehydrogenase gene, or the promoter and terminator sequences of the plasma membrane proton ATPase gene. It will also be appreciated by those skilled in the art that characteristics of C. utilis can be modified by expressing structural genes in C. utilis.

Heterologous genes or genes derived from C. utilis can be modified to be highly expressed in C. utilis. The gene can be modified to enable high level expression in C. utilis by optimizing the gene sequence to correlate with those codons most frequently used in C. utilis. For example, the gene sequence can be optimized according to the codons used with genes which are highly expressed in C. utilis.

A modified gene is synthesized by altering bases in codons without changing the amino acid sequence which the gene encodes. Specifically, those codons coding for the 18 amino acids, other than methionine and tryptophan, which are most frequently found in highly expressed genes such as the glyceraldehyde-3-phosphate-dehydrogenase (GAP) gene derived from C. utilis are used. It is desirable to design the structural gene in such a manner that appropriate restriction enzyme cleavage sites are located at intervals of about 250 to 300 bp so that the gene can be synthesized as several partitioned segments.

For example, the synthesized gene can be constructed as follows:

A DNA sequence is designed in such a manner that appropriate restriction enzyme cleavage sites are located in the structural gene at intervals of about 180 to 320 bp so that the structural gene synthesized as several partitioned segments can be ligated utilizing the restriction enzyme cleavage sites. Using the DNA sequence designed for the gene, a pair of single-stranded oligonucleotides having about 50 to 100 bases are synthesized by the conventional method and then a double-stranded segment is synthesized by PCR using these fragments as templates. Specifically, in synthesizing a 180-bp double-stranded DNA, a pair of 100 base oligonucleotides, which are overlapped about 20 bp at their 3' ends, are synthesized. The targeted double-stranded DNA is then obtained by a PCR reaction using these oligonucleotides as templates under the standard conditions. To synthesize a double-stranded DNA of about 340 bp, a second PCR reaction is carried out using as templates the double-stranded DNA obtained as described above and a pair of oligonucleotides of 100 bases, which are synthesized to have overlapped sequences of about 20 bp with the double-stranded DNA at their 3' ends. This final synthesized double-stranded DNA is designed to have specific restriction enzyme cleavage sites at both ends and preferably to have additional sequences of some 2 nucleotides outside of the restriction enzyme cleavage sites of both ends to facilitate digestion by the restriction enzymes.

One example of a modified heterologous gene is the amylase gene of SEQ ID NO: 14. The DNA sequence of SEQ ID NO: 14 is a novel sequence. Accordingly, another aspect of the present invention provides the amylase gene consisting of the DNA sequence of SEQ ID NO: 14. This amylase gene can be highly expressed in yeast such as *C. utilis* (see Examples).

Furthermore, the vector according to the present invention can be used for transformation of cells other than *C. utilis*. It is preferable to select an appropriate DNA fragment for transformation when cells other than *C. utilis* are used as host cells. Examples of such DNA fragments for *E. coli* include bacterial plasmid DNAs such as pBluescript and pUC19. For yeast of family Saccharomyces, yeast-*E. coli* shuttle vectors such as YEp13 and YCp50 (Methods in Enzymology, 194, 195–230, Academic Press, 1991) can be used.

A preferable embodiment of the vector according to the present invention is a vector which comprises a marker gene conferring cycloheximide resistance, a shortened promoter comprising the DNA sequence X-192 (wherein X represents an integer from 1 to 111) of SEQ ID NO. 1 operably linked to the marker gene, a sequence homologous to the chromosomal DNA of *C. utilis* other than the rDNA sequence ("homologous DNA sequence"), and a heterologous gene (e.g., the single-chain monellin gene, the amylase gene, or the glycosylation inhibiting-protein gene, which may be modified to be highly expressed in *C. utilis*) or a gene derived from *C. utilis*, and optionally a promoter sequence and a terminator sequence derived from *C. utilis* which are operably linked to the heterologous gene or the gene derived from *C. utilis*, wherein the vector is linearized by cleaving within or at both ends of the homologous DNA sequence with restriction enzymes, and wherein the heterologous gene or the gene derived from *C. utilis* can be integrated into the chromosomal DNA of *C. utilis* by homologous recombination.

More preferably, the DNA sequence containing a marker gene, a shortened promoter, a heterologous gene or a gene derived from *C. utilis*, and optionally a promoter and a terminator, is flanked by the URA3 gene at both ends.

The homologous DNA sequence can preferably be the URA3 gene sequence or a partial DNA sequence thereof.

Another aspect of the present invention provides a vector which comprises a gene conferring cycloheximide resistance, a heterologous gene or a gene derived from *C. utilis*, and optionally a promoter sequence and a terminator sequence derived from *C. utilis* which are operably linked to the heterologous gene or the gene derived from *C. utilis*, and wherein the vector is linearized by cleaving within or at both ends of the gene sequence conferring cycloheximide resistance by restriction enzymes, and wherein the heterologous gene or the gene derived from *C. utilis* can be integrated into the chromosomal DNA of *C. utilis* by homologous recombination.

The DNA sequence containing the heterologous gene or the gene derived from *C. utilis*, and optionally the promoter and the terminator, is flanked by the 5' end part and the 3' end part of the gene conferring cycloheximide resistance. When such vectors are integrated into the chromosomal DNA of *C. utilis* in a tandem form, the gene conferring cycloheximide resistance divided into the 5' end part and the 3' end part becomes united on the chromosome. As a result, transformants regain cycloheximide resistance and can be selected on a selective medium. The gene conferring cycloheximide resistance in the vector functions not only as a "homologous DNA sequence" for integration into the chromosome but also as a marker gene to select the transformants.

The term "vector" as used herein includes plasmids derived from bacteria.

Transformation

Transformants according to the present invention can be obtained by introducing a vector DNA (plasmid DNA) into a host such as *C. utilis* and selecting transformants which have become drug resistant.

Host cells are treated to enable them to incorporate foreign DNAs by methods conventionally used for transformation of *C. utilis*, such as the electric pulse method, the protoplast method, the lithium acetate method, and modified methods thereof.

In the electric pulse method, cells cultured up to the logarithmic growth phase are washed and then suspended in 1 M sorbitol. Pulsing can be performed under the conditions which would yield a time constant (time required to lower the voltage to about 37% of the maximum value) of about 10 to 20 milliseconds and cell viability of about 10 to 40% after pulsing. For example, the time constant and cell viability can be attained and about 500 to 1,400 transformants per 1 μg of DNA can be obtained at a capacitance of 25 μF, a resistance of 600 to 1,000 ohms, and a voltage of 3.75 to 5 KV/cm.

Furthermore, it is preferable to add a YPD medium containing 1 M sorbitol to the cell suspension after pulsing, and then incubate the suspension at 30° C. with shaking. There were occasions when no colony appeared on the selective medium plate containing cycloheximide when the cells were plated without this cultivation. An appropriate incubation time is about 4 to 6 hours; further extended incubation results in significant growth of transformants. It is also preferable to improve the transformation frequency of the transformation system according to the present invention; for example, by the addition of a carrier DNA such as salmon sperm DNA upon the contact of DNA with the cells, or by the addition of polyethylene glycol.

The lithium acetate method (Ito et al., J. Bacteriol., 153, 163–168, 1983) is extensively used for transformation of yeast of genus Saccharomyces because of its simplicity and convenience and various improved methods are reported. It has been confirmed that *C. utilis* can also be transformed using these methods (WO/95/32289). In particular, *C. utilis* can be transformed by the modified lithium method in which ethanol is added (Soni et al., Current Genet., 24, 455–459, 1993). It is also possible to increase transformation frequency by using the optimum conditions for *C. utilis* transformation, which can be determined experimentally by altering various conditions for the transformation; for example, cell density at cell harvest, lithium concentration, kind and concentration of polyethylene glycol, or the kind, form and amount of carrier DNA.

Examples of the host to be transformed with the vector according to the present invention include yeasts such as *C. utilis*. Examples of *C. utilis* strains include ATCC9256 (IFO 0626), ATCC9226 (IFO 1086), ATCC9950 (IFO 0988), IFO 0396, IFO 0619, IFO 0639, and KP-2059P.

All of the strains described above have been confirmed to produce transformants and express heterologous genes although three strains, ATCC9256, ATCC9226 and ATCC9950, show chromosomal polymorphism (Stoltenburg et al., Curr. Genet., 22, 441–446, 1992) (WO/95/32289). From these observations, it will be appreciated by those skilled in the art that the vector according to the present invention can be universally used with *C. utilis*.

Method of Producing Proteins

According to another embodiment of the present invention, *C. utilis* cells transformed with the vector according to the present invention are cultured and the expression product of a structural gene is isolated from the culture and purified to obtain a protein.

In a further embodiment of the present invention, the target protein can be prepared by culturing *C. utilis* cells transformed with the vector according to the present invention which carries the single-chain monellin gene or the amylase gene as a heterologous gene and isolating and purifying single-chain monellin or amylase from the culture. These genes may be modified to be highly expressed in the host cells.

When the rDNA was used as the target sequence, the vector alone was stable. However, the expression level decreased after 50 generations of cultivation because of a high level expression of protein. On the other hand, host cells having vectors which use sequences other than rDNA, such as the URA3 gene or the L41 gene, as the integration target stably maintained the vectors and the expression level remained high even after about 50 generations of cultivation (see Examples).

It was shown that the use of a vector which used the URA3 gene or the L41 gene as the integration target not only increased the number of copies but also remarkably improved the stability of the gene integrated into the chromosome.

The single-chain monellin, which is successfully expressed at a high level in the present invention, was proven to have a sweetness equivalent to natural monellin and a remarkably improved thermal stability in a low pH range (Japanese Patent Laid-open 1993/70494). In this molecule, chain A and chain B of natural monellin are connected by a glycine residue. The single-chain monellin primarily consists of a single chain in which subunit B of natural monellin is connected via its C terminal to the N terminal of subunit A of natural monellin by a covalent bond linker. Specifically, the single-chain monellin contains the amino acid sequence of SEQ ID NO: 6.

It is well known that the properties of proteins are virtually conserved even when their structural amino acids are partially deleted or substituted or other amino acids are added. This fact has also been confirmed with the single-chain monellin (Japanese Patent Publication 1990/504028, Japanese Patent Laid-open 1993/70494).

Accordingly, the term "single-chain monellin" as used herein includes monellin which has an amino acid sequence substantially equivalent to that of the single-chain monellin molecule. The term "substantially equivalent amino acid sequence" refers to a peptide which has a sweetness equivalent to natural monellin even if substitution, deletion or addition of amino acids occurs. Therefore, for example, an amino acid sequence in which Glu at position 50 and Asn at position 51 of SEQ ID NO: 6 are substituted with Asn and Glu, respectively (the amino acid sequence of SEQ ID NO: 5) is called a "substantially equivalent amino acid sequence," and a protein containing this sequence is called a "single-chain monellin." Further, the terms "peptide" and "protein" as used herein mean the same.

Once an amino acid sequence of a protein is given, a DNA sequence coding for the amino acid sequence can be readily determined and one can select it from a variety of possible DNA sequences. Accordingly, the term "single-chain monellin gene" refers to those DNA sequences encoding the amino acid sequence of the single-chain monellin including substantially equivalent amino acid sequences) which have degenerate codons in the sequence, in addition to the DNA sequence of SEQ ID NO: 4 and the DNA sequence coding for the amino acid sequence of SEQ ID NO: 6.

It will be appreciated by those skilled in the art that the use of those amino acid codons most suitable to the applicable yeast within the DNA sequence coding for the single-chain monellin will further improve the expression level.

The single-chain monellin which is expressed as a soluble protein in cells of yeast, including *C. utilis*, can be easily purified by heat treatment or acid treatment.

The heat treatment can be carried out at 50 to 70° C., preferably at about 60° C. to efficiently precipitate other undesirable proteins. The acid treatment can be carried out below pH 5, preferably at pH 4 to 5 to efficiently precipitate other undesirable proteins. Either of these treatments can increase the purity of the monellin to more than 80%.

Furthermore, the purity of the monellin can be increased to almost 100% by combining the heat treatment and acid treatment. The order of the treatments is not particularly restricted.

Furthermore, it will be appreciated by those skilled in the art that known purification procedures such as cation exchange chromatography can be used alone or in combination with the treatments described above.

Furthermore, it is preferable to make the protein concentration of the extract less than 10 mg/ml (preferably less than 3 mg/ml) to prevent coprecipitation of the single-chain monellin.

The soluble protein fraction is extracted and subjected to heat treatment or acid treatment or a combination of these treatments. The crude monellin thus obtained can be used as food or animal feed without further purification. Furthermore, monellin can be provided in combination with yeast, which is by itself an excellent food rich in various vitamins and dietary fibers, simply by an appropriate heat treatment of disrupted cells.

The methods can save time and costs for the protein purification process, which is particularly advantageous when the protein is to be used for animal feed.

EXAMPLES

The present invention is further specifically described with reference to the following examples, but it is not limited to the examples.

In this disclosure, restriction enzyme sites in the restriction enzyme maps of genes are represented by the following. Af;AflII, Ap; ApaI, Asp;Asp718, B; BamHI, Bg; BglII, C; ClaI, E; EcoRI, RV; EcoRV, H; HindIII, Hp; HpaI, K; KpnI, P; PstI, Pv; PvuII, S; SalI, Se; SpeI, Sm; SmaI, Sc; SacI, ScII; SacII, Sp; SphI, X; XbaI, and Xh; XhoI.

The methods used in the following examples are as follows:

Example 1

Preparation of *Candida utilis* Chromosomal DNA

The extraction of *Candida utilis* chromosomal DNA was carried out by the following procedure. ATCC 9950 strain of *Candida utilis* was inoculated in 30 ml of YPD medium and cultured at 30° C. early stationary phase. The cells were collected by centrifugation, washed with sterilized water, and collected again by centrifugation. After the cells were suspended in 3 ml of Zymolyase buffer (0.9 M sorbitol, 0.1 M EDTA, 50 mM DTT, pH 7.5), 200 μl of 0.9 M sorbitol containing 25 mg/ml Zymolyase 100T was added, and the mixture was incubated at 37° C. under shaking. After the formation of protoplast was confirmed by microscopic observation, the protoplasts were collected by centrifugation. After 3 ml of lysis buffer (50 mM Tris-HCl, 50 mM EDTA, pH 8.0) was added and the protoplasts were suspended gently and sufficiently in the buffer, 0.3 ml of 10% SDS was added, and the mixture was incubated at 65° C. overnight. Then, 1 ml of a 5 M potassium acetate solution was added, and the mixture was left standing on ice for 1 hour. Precipitates were then removed by centrifugation, 4 ml of cold ethanol was added, and the mixture was centrifuged to precipitate DNA. The precipitate was washed with 50% ethanol, dried, dissolved in 3 ml of an RNase A buffer (10 mM Tris-HCl, 1 mM EDTA, 50 μg/ml RNase A, pH 7.5), and incubated at 37° C. for 30 minutes. Finally, 3 ml of 2-propanol was added and the mixture was centrifuged to remove the supernatant. Precipitates thus obtained were washed with 50% 2-propanol and dried. The precipitate was dissolved in 0.5 ml of a TE buffer and used as a *Candida utilis* chromosomal DNA sample.

After the partial digestion of the *Candida utilis* chromosomal DNA with a restriction enzyme Sau3AI, the digested mixture was layered on a 10–50% sucrose density gradient containing 0.8 M NaCl, 20 mM Tris-HCl, 10 mM EDTA (pH 8.0), and centrifuged under 120,000×g for 14 hours to fractionate the DNA fragments. Among these fragments, 10–20 kb chromosomal DNA fragment was ligated overnight with dephosphorylated λ-phage vector DASHTMII (Stratagene Cloning Systems) which had been digested with BamHI, and then subjected to in vitro packaging to construct a *Candida utilis* genomic DNA library.

Example 2

Isolation of the rDNA

A 400 ng portion of 5–10 kb Sau3AI partially digested DNA fragments of *Candida utilis* ATCC 9950 genomic DNA obtained by the sucrose density gradient centrifugation described in Example 1, and 200 ng of vector plasmid pBR322 digested with BamHI and dephosphorylated were ligated overnight with T4 DNA ligase. *E. coli* DH5 was transformed with this DNA solution to construct a *Candida utilis* genomic DNA library.

Filters were prepared for about 10,000 colonies according to the method described in Molecular Cloning, 2nd edition, Sambrook et al., p12, 21–23, Cold Spring Harbor Laboratory (1989), and screened with the 1.8 kb $^{32}$P-labelled HindIII—EcoRI fragment containing *S. cerevisiae* 18S rRNA gene as a probe. The rDNA fragment used as the probe was prepared from a plasmid obtained from a genomic DNA library of *Saccharomyces cerevisiae* S288C [α, suc2, ma1, ga12, CUP1] with a $^{32}$P-labelled oligomer corresponding to the fragment of nucleotides 4-32 at 5'-terminal of the 5.8S rRNA gene as a probe (Sone et al., Japanese Patent Publication No. 14865/1994).

Over 200 positive clones were obtained. Restriction enzyme maps of plasmids from seven clones, pCR1, pCR4, pCR5, pCR6, pCR7, pCR8 and pCR9 were constructed and aligned for comparison. The restriction enzyme maps at the both terminals were accorded (FIG. 1). It has been found from this fact that the region containing the rRNA gene of *Candida utilis* has an about 13 kb repetitive structure.

From these plasmids, fragments cut out by digestion with EcoRI or XbaI were subcloned into pBluescript SK– to construct plasmids pCRE1, pCRE2, pCRE3, pCRX1, pCRX2, pCRX3 and pCRX4 (FIG. 2(a)). Furthermore, these plasmids were digested with a variety of restriction enzymes and recyclized to construct a variety of deletion plasmids. DNA sequences were determined on the insertion fragments of these plasmids and the regions where the DNA sequence was determined are shown by arrows in the figure. The analysis of the DNA sequences revealed the presence of the regions which have high homology with the 18S, 5.8S and 25S rRNA genes. Thus, the location and transcriptional direction of the three rRNA genes were determined (FIG. 2(b)).

Example 3

Isolation of the Orotidine 5'-phosphate Decarboxylase Gene (URA3 Gene)

A 100 ng portion of 5–10 kb Sau3AI partially digested DNA fragments of *Candida utilis* ATCC 9950 genomic DNA obtained by the sucrose density gradient centrifugation described in Example 1, and 100 ng of vector plasmid YEp13 (Methods in Enzymol., 194, 195–230, 1991) digested with BamHI and dephosphorylated were ligated overnight with T4 DNA ligase. *E. coli* DH5 was transformed with this DNA solution to construct a genomic DNA library. After the plasmid mixture was extracted from the transformants, *Saccharomyces cerevisiae* YPH 500 (α his3, trp1, leu2, ade2, lys2, ura3) (Stratagene Cloning Systems) which is a ura3-strain was transformed with the plasmid DNA mixture and the transformants which did not require uracil for growth were selected on a minimal medium. Transformation of *S. cerevisiae* was conducted according to the lithium method described in Methods in Yeast Genetics—A Laboratory Course Manual—Rose M. D. et al., p. 122–123, Cold Spring Harbor Laboratory Press, NY (1990).

Five Ura$^+$ strains were obtained from 10 μg of DNA by this procedure. Plasmid DNA was prepared from each of these transformants according to the method described in Methods in Yeast Genetics—A Laboratory Course Manual—Rose M. D. et al., p. 130, Cold Spring Harbor Laboratory Press, NY (1990). *E. coli* was transformed with the DNA, and a plasmid DNA was prepared. Restriction enzyme maps were constructed on the plasmids pCURA3-3 containing a 6.1 kb insert and pCURA3-5 containing a 8.1 kb insert at the BamHI site of YEp13, respectively.

Example 4

Characterization of URA3 Gene Region and Determination of DNA Sequence

Figure 3:
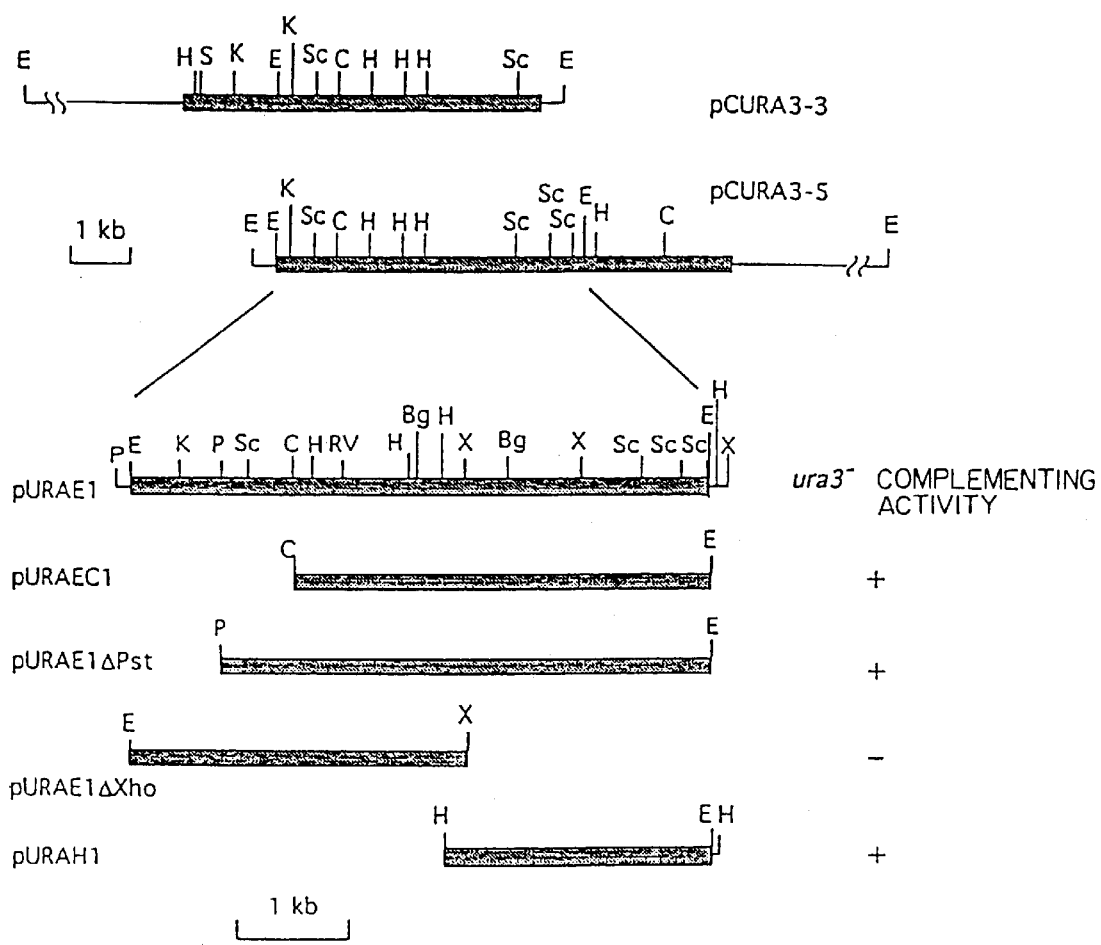
FIG. 3 shows restriction enzyme cleavage maps of plasmids containing the URA3 gene and the complementing activity of these plasmids with *S. cerevisiae* ura3$^-$ mutation.

In order to characterize the URA3 gene region, a 5 kb EcoRI fragment containing a region common to the plasmids pCURA3-3 and pCURA3-5 was cut out from a plasmid pCURA3-5 and ligated to the EcoRI site of a plasmid pRS314 (Stratagene Cloning Systems) to prepare a plasmid pURAE1 (FIG. 3). The YPH 500 strain was transformed with the plasmid by the lithium method. As a result, URA⁺ transformants were obtained in high frequency. This indicates that URA3 gene is present in the 5 kb EcoRI fragment, and one copy of the gene can complement the ura3⁻ mutation of *Saccharomyces cerevisiae*.

The plasmid pURAE1 was then digested with XhoI or PstI and recyclized by the T4 ligase reaction to give plasmids pURAE1 ΔXho and pURAE1 Pst.

Furthermore, the 3.5 kb EcoRI-ClaI fragment and the 2.3 kb HindIII fragment cut out from the plasmid pURAE1 were inserted between EcoRI and ClaI sites, or at the HindIII site of the pRS314, respectively, to prepare plasmids pURAEC1 and pURAH1 (FIG. 3).

The YPH500 strain was transformed with five plasmids described above by the lithium method to examine the complementarity of ura3⁻ mutation and thus to examine whether these fragments contain the URA3 gene or not. The result is shown in FIG. 3. The results showed that the URA3 gene is located in 2.3 kb region between the EcoRI and HindIII.

Figure 4:
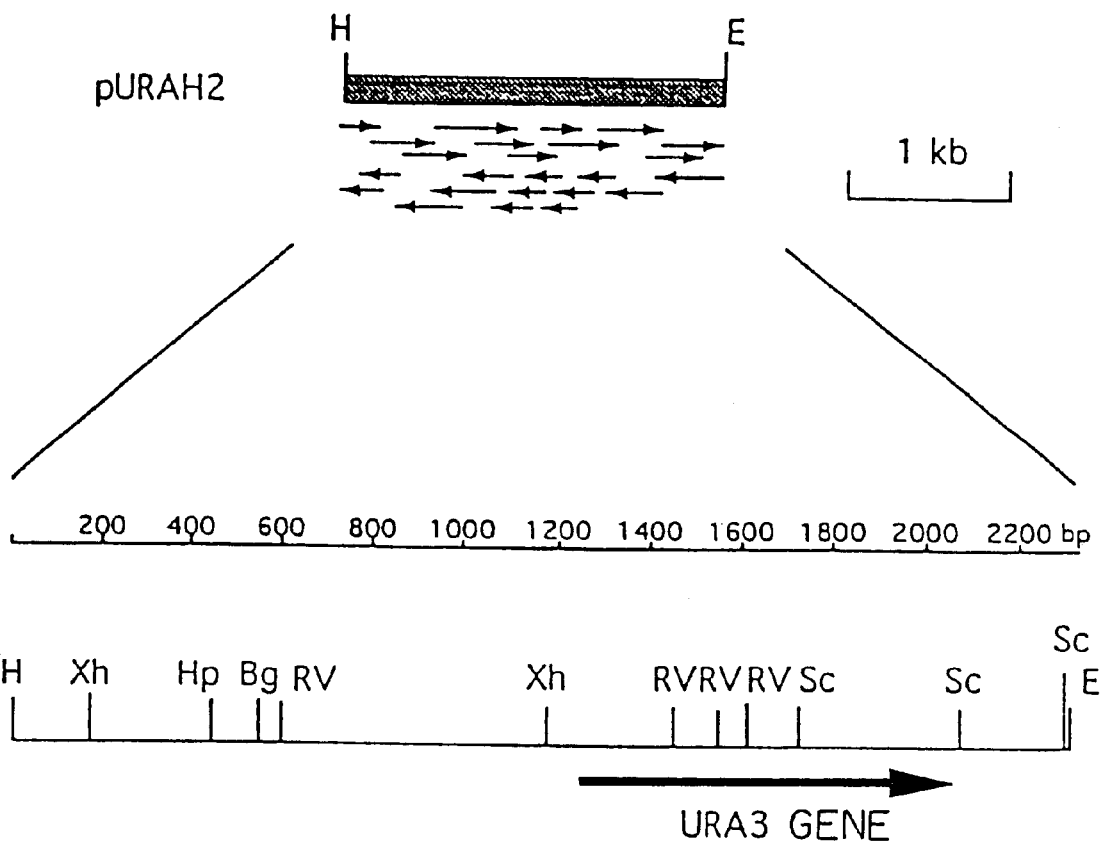
FIG. 4 shows the strategy for determination of DNA sequence of the URA3 gene and the restriction enzyme cleavage map.

Furthermore, the 2.3 kb HindIII fragment containing the URA3 gene was ligated to the HindIII site of the plasmid pBluescrip SK- to prepare a plasmid pURAH2. By the deletion mutation with ExoIII nuclease and mung bean nuclease from both ends of the inserted fragment, plasmids having deletion mutation were prepared, and the DNA sequence was determined. The restriction enzyme map which has been clarified by the DNA sequence and the sequence strategy are shown in FIG. 4. The 2330 bp DNA sequence thus obtained is shown in FIG. 5, and the deduced amino acid sequence of the polypeptide consisting of 267 amino acid residues is shown in FIGS. 6 and 7.

The amino acid sequence of the polypeptide was compared with that of the URA3 protein of the other yeasts, showing high homologies, for example 73.4% to *Saccharomyces cerevisiae*, 76.3% to *Kluyveromyces lactis*, and 75.1% to *Candida albicans*.

Example 5

Cloning of the L41 Gene and Determination the DNA Sequence of a DNA Fragment Containing the L41 Gene Filters were prepared for about 30,000 colonies of the library prepared in Example 2 according to the method described in Molecular Cloning, 2nd edition, Sambrook et al., p. 12, 21–23, Cold Spring Harbor Laboratory (1989), and screened with a 1.1 kb ³²P-labelled XbaI-Sau3AI fragment containing *Candida maltosa* L41 gene, RIM-C, as a probe (Kawai et al., J. Bacteriol., 174, 254–262 (1992)).

Figure 8:
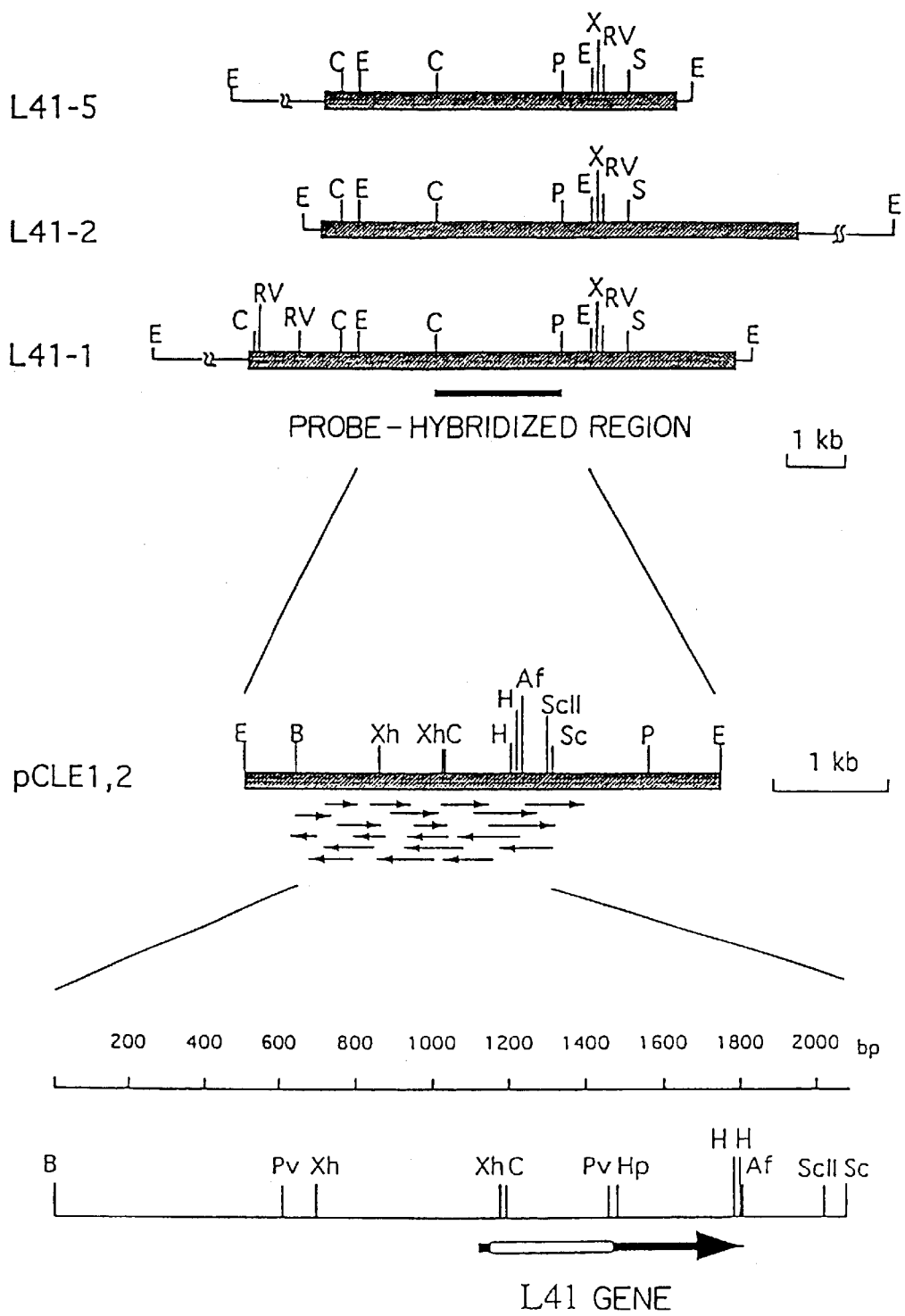
FIG. 8 shows restriction enzyme cleavage maps of the plasmids containing the L41 gene and the strategy for DNA sequence determination.

Five positive clones were thus obtained. Restriction enzyme maps of the three clones, pCL41-1, pCL41-2 and pCL41-5 were constructed and compared with each other. These clones have a 4 kb EcoRI fragment in common (FIG. 8). Southern hybridization analysis of these plasmid DNA has revealed that a region which shows homology to the L41 gene of Candida maltosa is present in the 1.4 kb ClaI-PstI fragment within the 4 kb EcoRI fragment.

The 4 kb EcoRI fragment was inserted into the EcoRI site of pBluescript SK⁻ to prepare plasmids pCLE1 and pCLE2 in which the fragment is inserted to an opposite direction with each other. From these two plasmids, a variety of plasmids having deletion mutations were obtained by preparing deletion mutants with HindIII, XhoI or ClaI having a site within the EcoRI fragment or by preparing deletion mutants with ExoIII nuclease and mung bean nuclease in order to determine the 2086 bp DNA sequence from the BamHI site to the SacI site (FIG. 9).

Southern analysis revealed that a 318 bp open reading frame interrupted by a 367 bp intron is present in the region in which the presence of an L41 structural gene is deduced (FIGS. 8 and 10). At the 5' and 3' terminals and in the neighborhood of the 3' terminal in the region which was deduced to be an intron, sequence (SEQ ID NO: 16) GTATGT-TACTAAC-AG which is common to intron was observed. Furthermore, the sequences were located at immediately after the initiation codon as well as six L41genes of the other yeasts described by Kawai et al., J. Bacteriol., 174, 254–262 (1992); Pozo et al., *Eur. J. Biochem.*, 213, 849–857 (1993)). The deduced amino acid sequence of the *Candida utilis* L41 polypeptide was compared with those of the L41 proteins of some other yeasts, showing high homologies, for example 93.4% to *Saccharomyces cerevisiae* L41, 89.6% to *Candida tropicalis* L41, and 85.8% to *Candida maltosa* L41.

Example 6

Preparation of Cycloheximide-resistance L41 Gene by Site-specific Mutation

The amino acid at 56 position of the L41 protein of a cycloheximide-resistant yeast is glutamine, while the amino acid at the corresponding position in the L41 protein of a cycloheximide-sensitive yeast is proline. It has been reported that the sensitivity to cycloheximide of the yeast is determined by this amino acid residue of the L41 protein (Kawai et al., J. Bacteriol., 174, 254–262 (1992)). In addition, the amino acid at 56 of the L41 protein of a cycloheximide-sensitive *Candida utilis* was proline like that of a cycloheximide-sensitive *Saccharomyces cerevisiae*. The codon encoding the proline at the 56 position of the L41 gene was changed into a glutamine codon by site-specific mutagenesis in order to convert the L41 protein encoded by the gene into a cycloheximide-resistant protein, which was used as a selectable marker of transformation.

Figure 11:
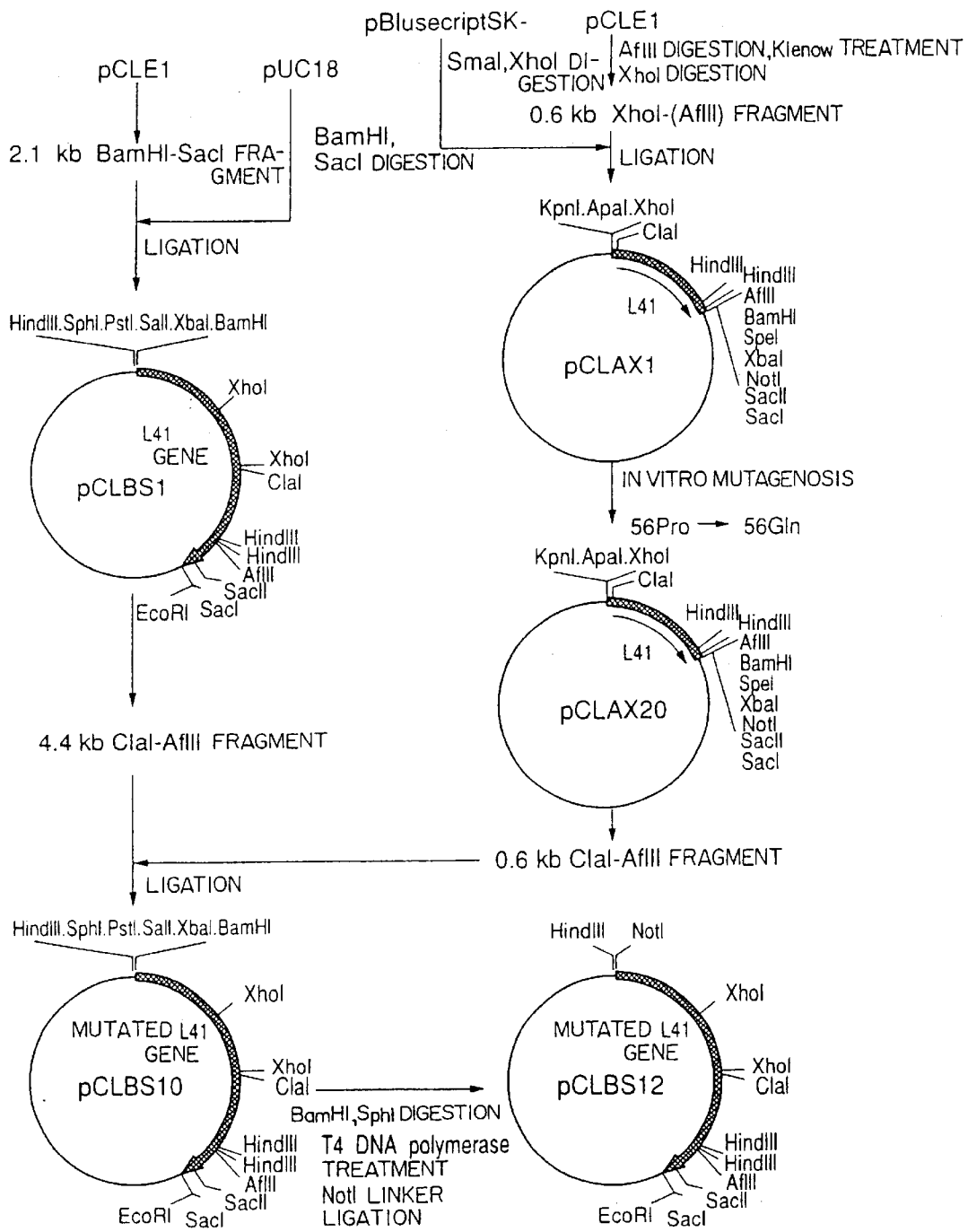
FIG. 11 shows the construction of plasmids pCLBS10 and pCLBS12.

Firstly, a 2.1 kb BamHI-SacI fragment obtained from the plasmid pCLE1 was inserted between the BamHI and SacI sites of pUC18 to prepare a plasmid pCLBS1 (FIG. 11).

Furthermore, 0.6 kb fragment obtained by digesting the plasmid pCLE 1 with AflII, treating with Klenow enzyme to form blunt ends and further digesting with XhoI was inserted between the SmaI and XhoI sites of pBluescript SK⁻ to prepare pOLAX1. In this plasmid, the AflII site is regenerated by the ligation of the blunt AflII end of the 0.6 kb fragment and the SmaI end of a vector. A single stranded DNA was prepared from pCLXA1 with a helper phage, and a mutant plasmid was prepared with a synthetic oligonucleotide 5'-TG TGG AAA ACT TGC TTG GTT TGA-3' (SEQ ID NO: 17) and a Sculptor In Vitro Mutagenesis Kit (Amersham). DNA sequence of the 0.6 kb insertion fragment on the candidate plasmid thus obtained was determined, and a plasmid pCLAX20 in which no mutation in the DNA sequence was found except that the 56$^{th}$ proline codon CCA had been mutated into a glutamine codon CAA was obtained.

A 0.6 kb insertion fragment was cut out as a ClaI-AflII fragment from pCLAX20 and ligated with a 4.4 kb fragment obtained by digesting the plasmid pCLBS1 with ClaI and AflII to construct a plasmid pCLBS10 containing a mutated L41 gene.

The plasmid pCLBS10 was digested with BamHI and SphI, treated with T4 DNA polymerase to form blunt ends, and NotI linkers (5'-AGCGGGCGCT-3' (SEQ ID NO: 18) were inserted to prepare a plasmid pCLBS12 (FIG. 11).

It was examined whether the mutated L41 gene thus obtained confers yeast resistance to cycloheximide or not. A 2.1 kb BamHI-SacI fragment containing the mutated L41 gene which was obtained from the plasmid pCLBS10 was inserted between the BamHI and SacI sites of YEp13K, a YEp vector (Sone et al., Appl. Environ. Microbiol., 54, 38–42 (1988)), to prepare a plasmid pYECL10. On the other hand, a 2.1 kb BamHI-SacI fragment containing the wild type L41 gene obtained from pCLBS1 was cloned into the YEp13K to prepare a plasmid pYECL1 as a control.

A Saccharomyces yeast strain YPH 500 was transformed with these plasmids according to the lithium acetate method described in Methods in Yeast Genetics—A Laboratory Course Manual—Rose M. D. et al., pp 122–123, Cold Spring Harbor Laboratory Press, NY (1990). Leucine non-requirement strains were selected as transformants. These transformants were grown on YPD plate containing cycloheximide. As a result, the strain retaining pYECL10 grew on the YPD plate containing cycloheximide. On the contrary, the strain retaining pYECL1 did not grow on the YDP plate containing cycloheximide. It was thus proved that the mutated L41 gene thus prepared conferred resistance to the cycloheximide-sensitive yeast.

Example 7

Figure 12:
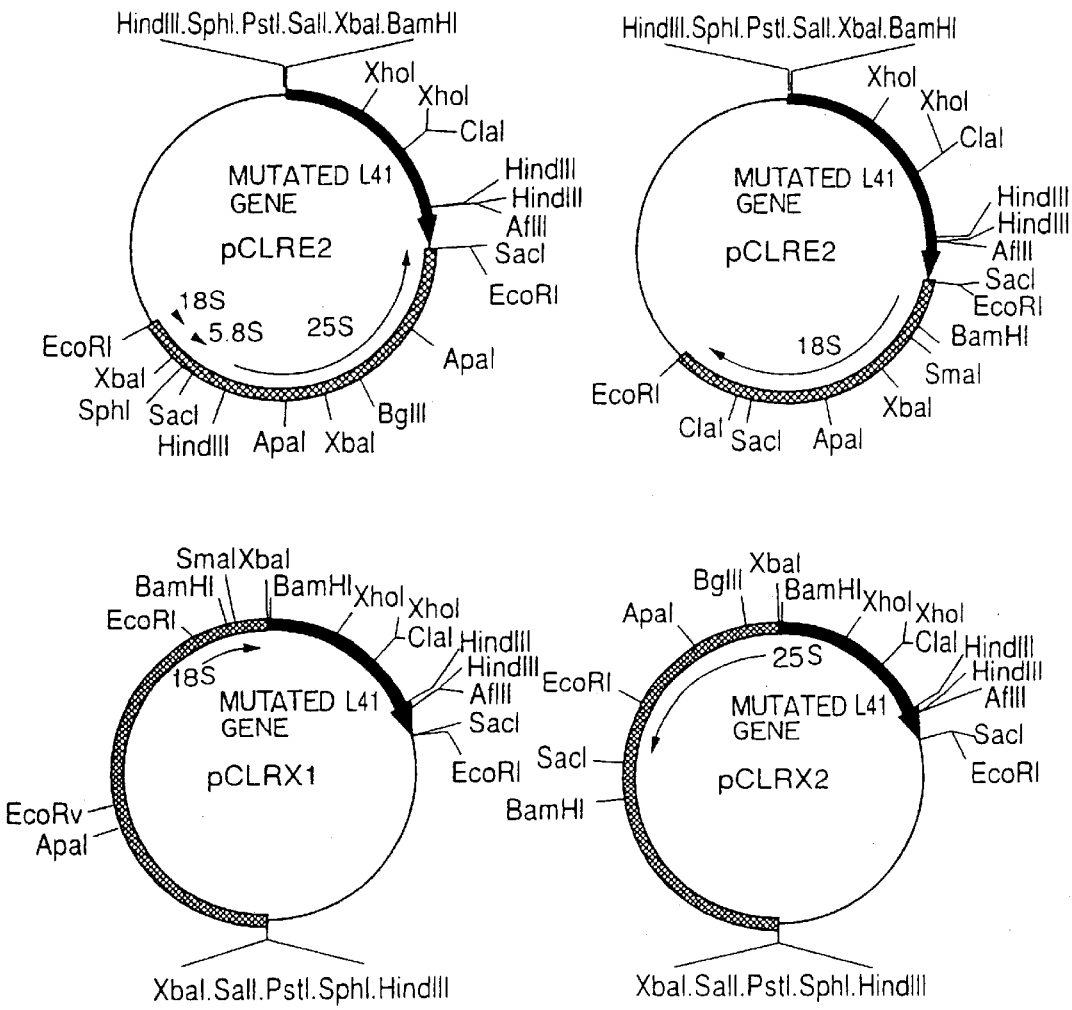
FIG. 12 shows the structure of plasmids pCLRE2, pCLRE3, pCLRX1 and pCLRX2.

High-copy-number Integration of Vectors by Trancating the L41 Gene Promoter (1) Construction of Promoter-deficient Mutants Four kinds of rDNA fragments which were excised from plasmids pCRE2, pCRE3, pCRX1, and pCRX2 as shown in Example 2 (FIG. 2) by EcoRI or XbaI were inserted into the EcoRI and XbaI sites of the plasmid pCRBS10 (FIG. 11) described in Example 6 to construct plasmids pCLRE2, pCLRE3, pCLRX1, and pCLRX2 (FIG. 12). The structure of the plasmid pCLRE2 containing the C. utilis L41 gene, which is made to confer cycloheximide resistance by introducing site-specific mutation, and the C. utilis ribosomal DNA fragment is shown in FIG. 13a.

This plasmid (5 μg) was digested with PstI and BamHI, then extracted with phenol/chloroform to recover DNA by ethanol precipitation. The DNA was dissolved in 100 μl of ExoIII buffer (50 mM Tris-HCl (pH8.0), 100 mM NaCl, 5 M MgCl$_2$, 10 mM 2-mercaptoethanol), 180 units of ExoIII nuclease were added, then the solution was maintained at 37° C. A sample (10 μl) was taken every minute and transferred into 10 μl of MB buffer (40 mM sodium acetate, 100 mM NaCl, 2 mM ZnCl$_2$ and 10% glycerol (pH 4.5)) in an ice-cold tube. Ten tubes thus prepared were maintained at 65° C. for 10 minutes to inactivate the enzymes, 5 units of mung bean nuclease was added, and the mixture was reacted at 37° C. for 30 minutes. After the reaction, the level of deletion was confirmed by agarose gel electrophoresis, and DNA fragments were recovered from five reaction solutions. The recovered DNA fragments were treated with Klenow enzyme to create blunt ends, a ligation reaction was carried out at 16° C. overnight, then transformation of E. coli was performed.

(2) Transformation and Analysis of Transformants

Transformation was carried out using a plasmid carrying the modified L41 gene containing −411 XhoI to +976 SacI and a plasmid carrying the modified L41 gene containing −1110 BamHI to +976 SacI. The transformation frequencies with these plasmids were virtually the same. Thus, the region downstream from the −411 XhoI site (where A at the initiation codon ATG is +1) was satisfactory as a promoter region for the expression of the L41 gene. Accordingly, 10 plasmids, pCLRE11 to pCLRE20 with deletions ranging from near the XhoI site to near the 3' downstream translation initiation codon were selected.

About 10 μg each of these plasmids were digested with BglII and used for transformation of C. utilis ATCC9950. Plasmids pCLRE11 to pCLRE20 were constructed in the same manner as pCLRE2. The transformation was carried out by the electric field pulse method (see WO/95/32289). Pulsing was performed at a capacitance of 25 μF, a resistance of 1,000 ohms, and a voltage of 5 KV/cm. Results showed that the transformation frequency decreased as the extent of deletion in the promoter region of the cycloheximide-resistance L41 gene increased. Specifically, the transformation frequencies were virtually the same with plasmids pCLRE11, pCRE12 and pCRE13, in which the extent of deletion was almost the same, but decreased with pCLRE14 to about 30%, with pCLRE15 and pCLRE16 to about 15%, and with pCLRE17 to about 0.3% of the frequency with pCLRE11 or 12. No transformants were obtained with pCLRE18, pCLRE19 and pCLRE20.

In FIG. 13b, the 5' ends of the L41 gene promoter region of the plasmids pCLRE11, pCLRE15, pCLRE16, pCLRE17, pCLRE18, pCLRE19 are indicated by arrows.

DNAs were prepared from the four independent clones, the transformants obtained with PCLRE15, pCLRE16 and PCLRE17 as well as pCLRE11. The DNAs were subjected to Southern blot analysis. A chromosomal DNA was prepared according to the method described in Methods in Yeast Genetics—A Laboratory Course Manual—Rose M. D. et al., pp131–132, Cold Spring Harbor Laboratory Press NY. The DNA thus prepared was digested with HindIII, subjected to agarose gel electrophoresis and then transferred to Hibond N+Filter (Amersham) to prepare a filter for Southern hybridization. The filter on which the DNA was immobilized was prehybridized in a hybridization solution (6×SSC, 5×Denhardt solution, 0.2% SDS) at 65° C. for 2 hours.

Hybridization was next carried out using a 0.6 kb ClaI-HindIII fragment, which contained the L41 gene labeled with [α-$^{32}$P]dCTP (110 TBq/mmol) using Megaprime DNA labeling systems (Amersham), as a probe DNA at 65° C. for 16 hours. After the hybridization, the filter was washed in 1×SSC and 0.1% SDS at 65° C. for 2 hours and then subjected to autoradiography where signals were detected. A thick band derived from the integrated vectors was observed along with a band derived from the endogenous L41 gene. The number of copies of the integrated plasmids was estimated by comparing the intensity of the bands, assuming that the intensity of the band derived from the endogenous L41 gene corresponds to two copies since the number of copies for the C. utilis L41 gene has previously been proven to be 2 per cell. The intensity of the bands was measured using a BAS 2000 imaging analyzer (Fiji Film). FIG. 14 shows the results of Southern blot analysis and a graph showing the number of copies.

While the number of copies of the plasmid pCLRE11 carrying the promoter region up to −420 was 9 to 14, the number of copies of the plasmids in which the promoter region was cut up to −190 (pCLRE15), −180 (pCLRE16) and −80 (pCLRE17) were 14 to 30 (pCLRE15), 17 to 42 (pCLRE16), and 35 to 90 (pCLRE17), respectively. Thus, it was shown that the number of copies integrated into the chromosome increased upon transformation in several vectors in which the marker gene, i.e., the promoter region of the cycloheximide-resistance L41 gene, was shortened.

Example 8

Construction of the Vectors for High-copy-number Chromosome Integration (1) Construction of the Vectors Targeted at the rRNA Gene Locus An approximately 1.2-kb fragment containing the ribosomal DNA obtained by digesting plasmid pCLRE2 with ApaI was cloned at the ApaI site of pBluescript SK (Stratagene) to construct plasmid pCRA1. This pCRA1 was then digested with XhoI and treated with Klenow enzyme to create blunt ends and then SphI linkers (5'-GGCATGCC-3') were added to construct pCRA2. SphI-EcoRI fragments containing the L41 gene excised from plasmids pCLRE15, pCLRE16 and pCLRE17 were cloned between the SphI site and the EcoRI site of this plasmid to construct plasmids pCLR215, pCLR216 and pCLR217, respectively (FIG. 15).

Figure 16:
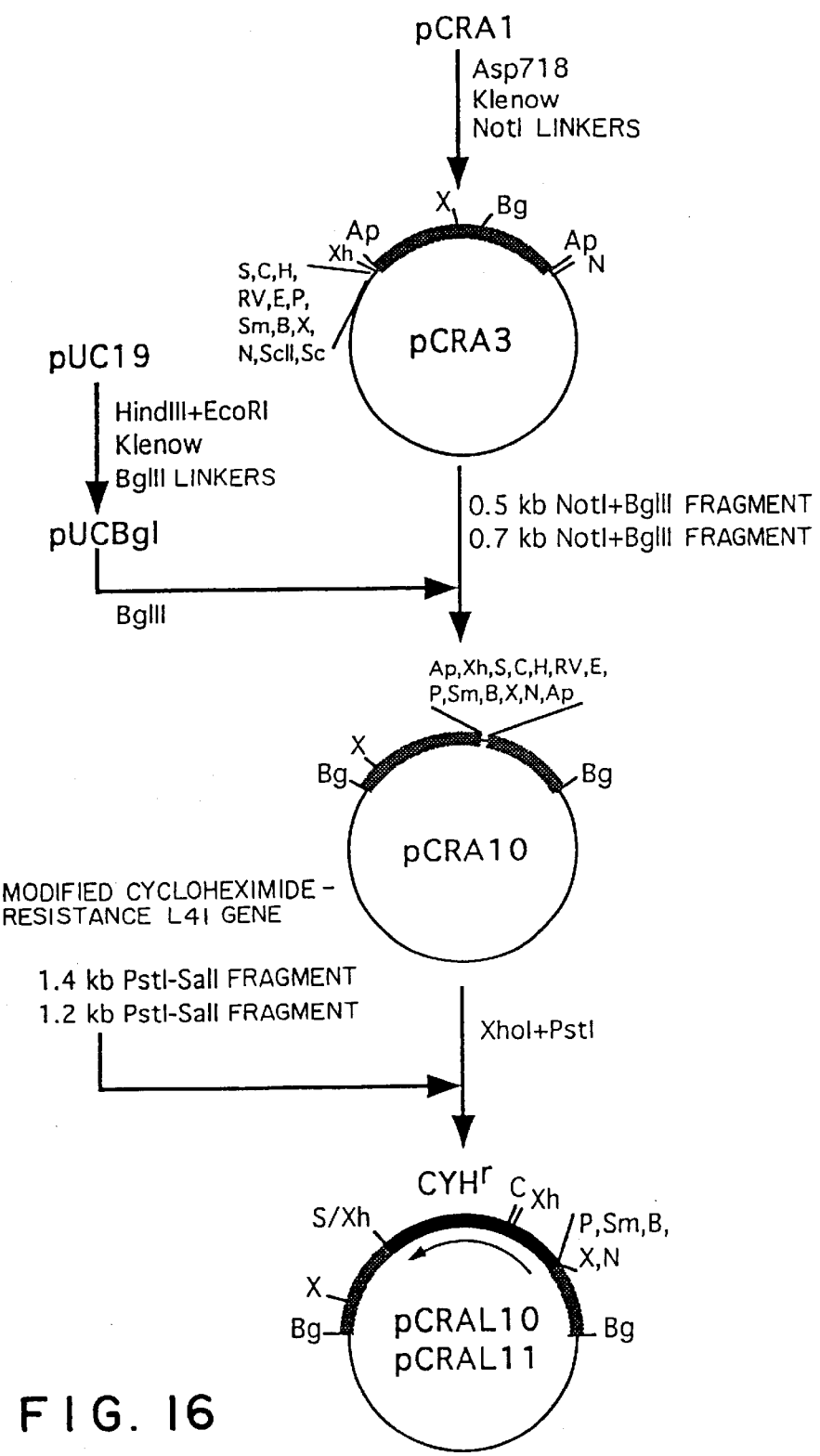
FIG. 16 shows the construction of plasmids pCRAL10 and pCRAL11.

Also, pCRA1 was digested with Asp718 and treated with Klenow enzyme to create blunt ends and then NotI linkers (5'-AGCGGCCGCT-3') (SEQ ID NO: 18) were added to construct pCRA3. This plasmid was digested with NotI and BglII to obtain 0.5-kb and 0.7-kb NotI-BglII fragments. Moreover, pUC19 (Takara Shuzo) was digested with HindIII and EcoRI and treated with Klenow enzyme to create blunt ends and then BglII linkers (5'-CAGATCTG-3') were added to construct plasmid pUCBgI. After digesting this plasmid with BglII, the two types of NotI-BglII fragments were cloned to construct pCRA10 (FIG. 16). In order to control the number of copies to be integrated into the chromosome, two fragments, with different lengths of promoter region, of the cycloheximide-resistance L41 gene, used as marker genes, were obtained by PCR. Specifically, the fragment from −405 to +974 and the fragment from −184 to +974 were obtained (where A in the initiation codon ATG is +1). These fragments were almost identical to the L41 gene fragment in plasmid pCLRE11 in which about 10 copies were integrated and that in plasmid pCLRE16 in which about 20 to 40 copies were integrated, respectively. In this case, the primers were designed to have an additional PstI site at the 5' end of the primer and a SaiI site at the 3' end of the primer. Sequences of the primers used for the PCR were as follows:

5'-side primers for the L41 gene:

5'-CCTGCAGGAAACGTAAACAAAGAGGTTTCA-3' (SEQ ID NO: 19)

5"-CCTGCAGGCCCACGCAACACCTGGTGTCTG-3' (SEQ ID NO: 20)

3'-side primer for the L41 gene:

5'-DGGTCGACTCGCTTTTGTGGGTGTGTGCATT-3' (SEQ ID NO: 21).

pCLRE2 was used as a template. Two amplified fragments were cloned into plasmid pT7Blue using the TA cloning kit (Invitrogen). These two kinds of fragments were excised as PstI-SalI fragments from the plasmids thus constructed and then ligated with pCRA10 to construct plasmid pCRAL10 containing the long L41 gene fragment and plasmid pCRAL11 containing the short L41 gene fragment.

In these plasmids pCRAL10 and pCRAL11, the integration target rDNA fragment is divided into two segments, and a sequence derived from plasmid pUC containing the Amp-resistance gene is integrated between the segments. Since this vector is used for transformation after digestion at the BglII site, the resulting transformant incorporates the target DNA sequence and the marker gene therein, but not the DNA sequence derived from the plasmid pUC.

(2) Construction of the Vectors Targeted at the URA3 Gene Locus

Primers were designed based on the URA3 gene sequence of *C. utilis* (see Example 4), and two kinds of fragments containing the 5' side and 3' side of the URA3 gene were obtained by PCR.

A fragment from +4 to +354 (where A in the initiation codon ATG is +1) was obtained as the 5' side fragment of the URA3 gene. In this case, the primers were designed to have an additional SalI site at the 5' end of the primer and a BglII site at the 3' end of the primer. Sequences of the primers were as follows:

5'-GGGTCGACATGTCACCACGTTATCGTACAC-3' (SEQ ID NO: 22)

5'-GGAGATCTGCCCATTGCGCAATCTT-3' (SEQ ID NO: 23)

A fragment from +356 to +685 was obtained as the 3'-side fragment of the URA3 gene. In this case, the primers were designed to have a BglII site at the 5' end of the primer and a Asp718 (KpnI) site at the 3' end of the primer. Sequences of the primers were as follows:

5'-GGAGATCTCACCAACGCCCACGGTGT-3' (SEQ ID NO: 24)

5'-GGGGTACCTAGCCACCACTGACAACCTCAT-3' (SEQ ID NO: 25)

Figure 17:
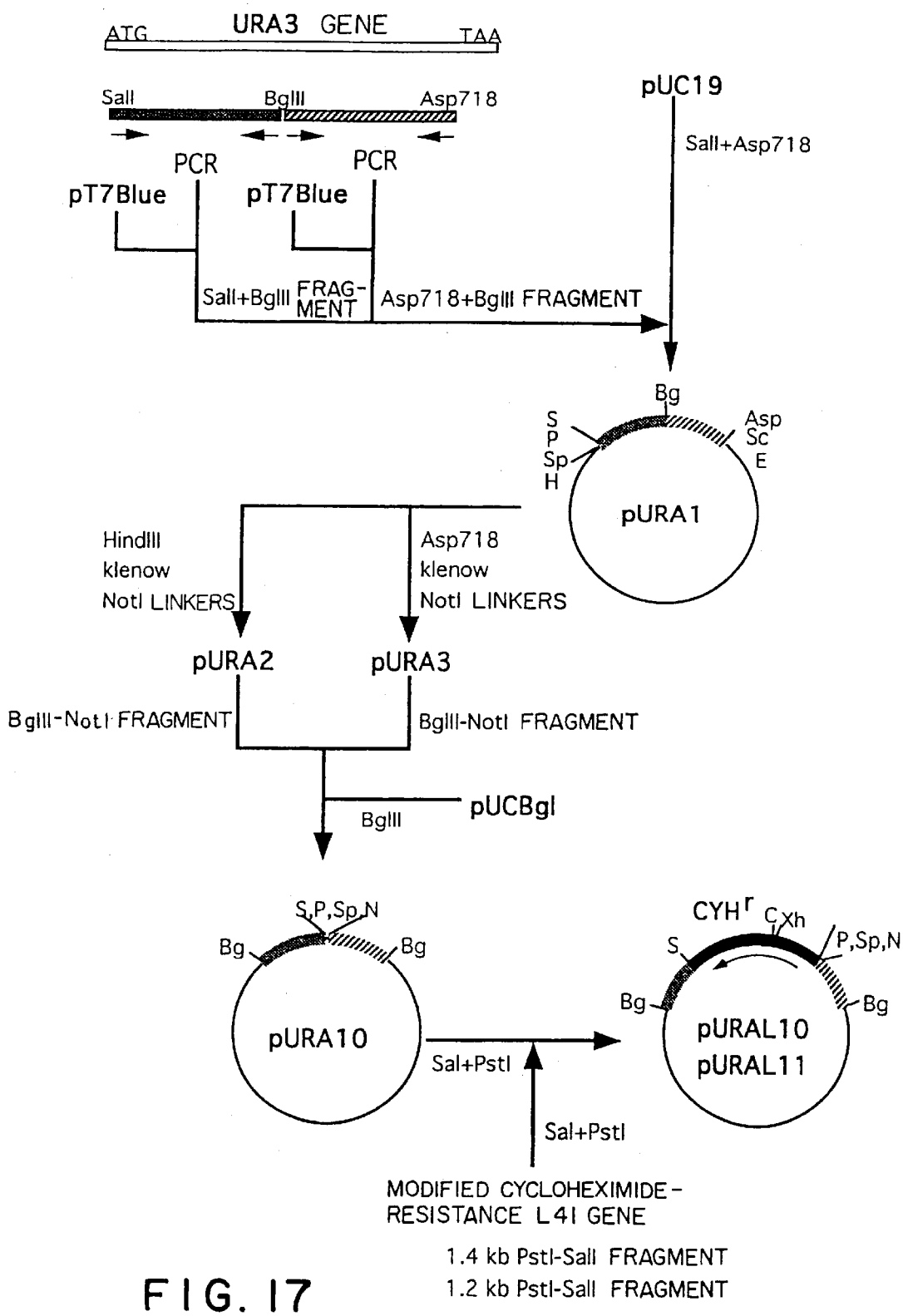
FIG. 17 shows the construction of plasmids pURAL10 and pURAL11.

The two amplified fragments thus obtained were cloned into plasmid pT7Blue using the TA cloning kit (Invitrogen). The 5'-side fragment and the 3'-side fragment of the URA3 gene were excised from the two kinds of constructed plasmids as a SalI-BglII fragment and a BglII-Asp718 fragment, respectively, and inserted between the SalI site and the Asp718 site of pUC19 (Takara Shuzo) to construct plasmid pURA1. The plasmid was modified to have a BglII site by changing the base A located at +355 in the open reading frame of the URA3 gene to C. The plasmid could be integrated into the URA3 gene on the chromosome by digesting the plasmid with BglII. Furthermore, the URA3 gene of pURA1 has a structure having partial deletions at the 5'-end region and 3'-end region of the open reading frame.

pURA1 was digested with Asp718 and treated with Klenow enzyme to create blunt ends and then Not linkers (5'-AGCGGCCGCT-3') (SEQ ID NO: 18) were ligated to construct plasmid pURA2. Furthermore, pURA1 was digested with HindIII and treated with Klenow enzyme to create blunt ends and then NotI linkers (5'-AGCGGCCGCT-3') (SEQ ID NO: 18) were ligated to construct plasmid pURA3. Furthermore, pURA2 and pURA3 were digested with NotI and BglII to obtain two kinds of approximately 0.35-kb NotI-BglII fragments. These fragments were then cloned into the BglII-digested pUCBg1 to construct pURA10 (FIG. 17).

Furthermore, two kinds of fragments of different length and containing the cycloheximide-resistance L41 gene obtained by PCR in (1) were ligated with pURA10 to construct plasmid pURAL10 containing the long L41 gene fragment and plasmid pURAL11 containing the short L41 gene fragment.

These plasmids pURAL10 and pURAL11 have the structure in which the integration target URA3 fragment is divided into two segments, and the sequence derived from plasmid pUC containing the Amp-resistance gene is integrated between the segments. Since this vector is used for transformation after digestion at the BglII site, the resulting transformant does not incorporate the DNA sequence derived from plasmid pUC.

(3) Construction of the Vector Targeted at the L41 Gene Locus

Vectors targeted at the (cycloheximide-resistance) L41 gene locus were constructed as follows. Two (cycloheximide-resistance) L41 gene fragments, approximately 380-bp (−85 to +292) and approximately 680-bp (+288 to +971), were obtained by PCR. The position of the 5' end of the 5'-side fragment is almost identical to that of the 5' end of the (cycloheximide-resistance) L41 gene promoter in pCLRE17. As such, for the fragment from −85 to +292, a PstI site was added to its 5' side and a BglII site was constructed at the 3' side by substituting T at +289 with G. Primers used for PCR were as follows:

5'-CCTGCAGACCGGTGAAATTTATCGAAA-3' (SEQ ID NO: 26)

5'-GAGATCTGATGATGCCTGTTGATATTCATC-3' (SEQ ID NO: 27)

As for the fragment from +288 to +971, PstI and NotI sites were added to its 3' side and a BglII site was constructed at the 5' side by substituting T at +289 with G. Primers used for PCR were as follows:

5'-GAGATCTCTACAATGGCTCGTTCCCA-3' (SEQ ID NO: 28)

Figure 18:
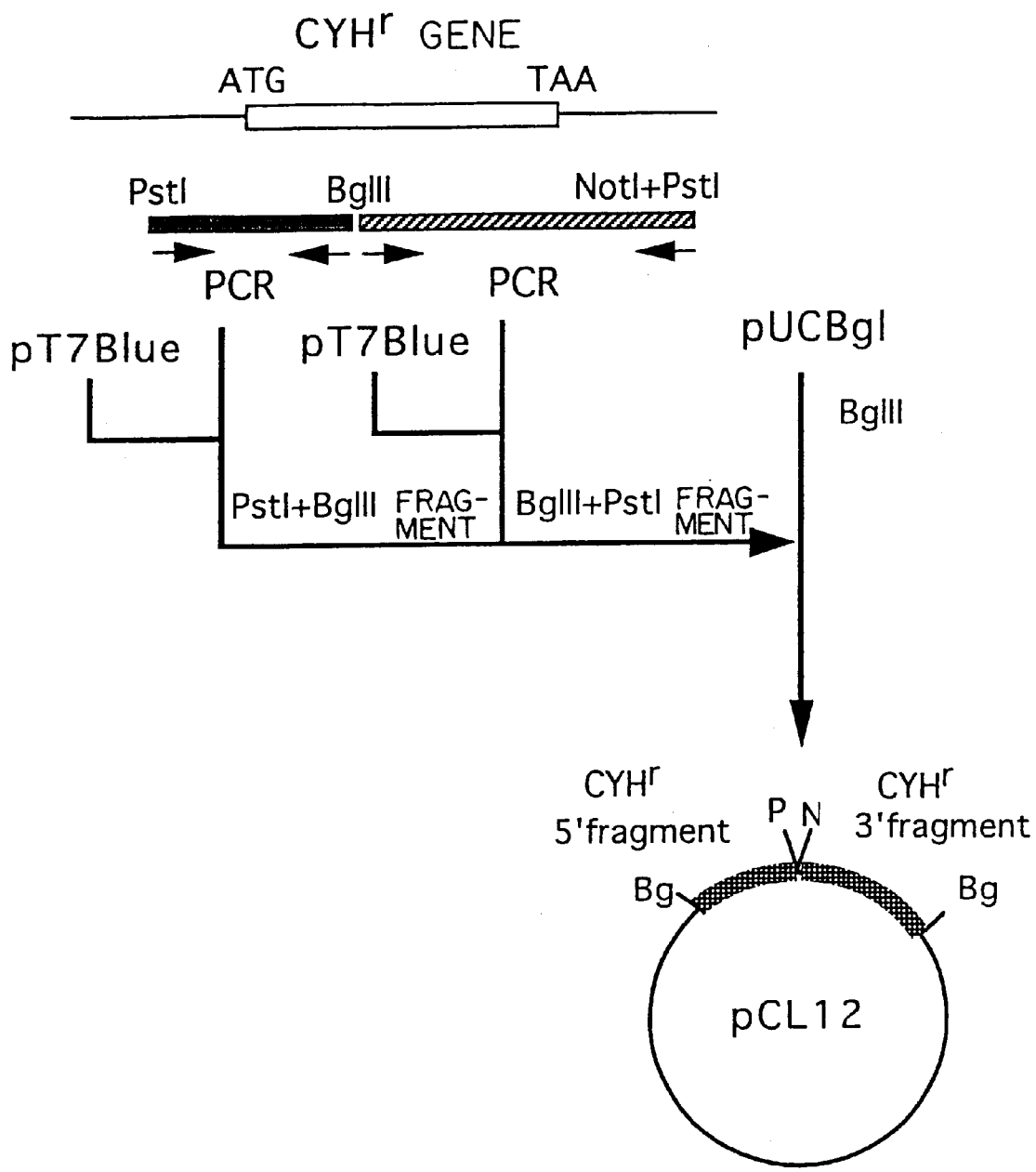
FIG. 18 shows the construction of plasmid pCL12.

5'-CCTGCAGGGCGGGCGCTTTTGTGCGTGTGTGCATTT-3' (SEQ ID NO: 29)

pCLRE2 was used as a template. Two amplified fragments were cloned into plasmid pT7Blue using the TA cloning kit (Invitrogen). These two kinds of fragments were excised as PstI-SalI fragments from the plasmids thus constructed and cloned into a BglII-digested pUCBgl to construct plasmid pCL12 (FIG. 18).

The plasmid pCL12 has the structure in which the L41 gene fragment, the integration target sequence, is divided into two segments, and the sequence derived from plasmid pUC containing the Amp-resistance gene is integrated between the fragments. Since this vector is used for transformation after the digestion at the BglII site, it is characterized in that the resulting transformants incorporate the target DNA sequences and the heterologous gene therein but not the DNA sequence derived from the plasmid pUC. Furthermore, since the marker gene is divided by the sequence derived from the plasmid pUC on the vector, cycloheximide-resistant transformants can be obtained only when this plasmid is integrated into the chromosome in a tandem form.

Example 9

Figure 19:
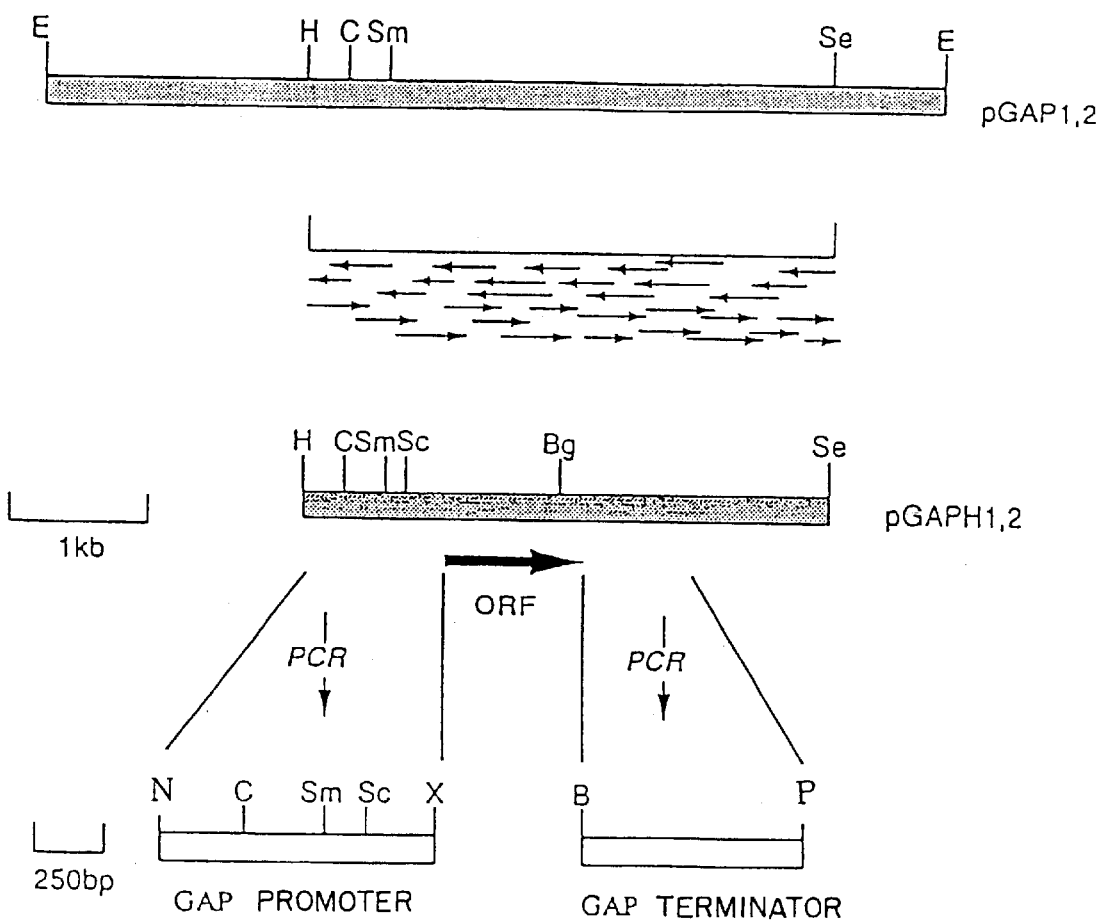
FIG. 19 shows the restriction enzyme cleavage map of a plasmid containing the glyceraldehyde-3-phosphate dehydrogenase (GAP) gene, the strategy for DNA sequence determination, and a method for obtaining a promoter fragment and a terminator fragment by PCR.

Construction of the Monellin Expression Plasmid (1) Cloning of the Glyceraldehyde-3-phosphate Dehydrogenase (GAP) Gene The glyceraldehyde-3-phosphate dehydrogenase (GAP) gene from C. utilis was cloned by the hybridization method in which a known GAP gene from other organisms was used as a probe. The DNA library of the C. utilis chromosome constructed in Example 1 was used as the gene library. A filter was prepared by adsorbing about 20,000 plaques of phage DNA of the gene library according to the method described in Molecular Cloning 2nd Edition, p2, 95–121, Cold Spring Harbor Laboratory, 1989. An approximately 1-kb AsuII-AflII fragment was then excised from the pUC18 plasmid carrying a 2.1 kb HindIII fragment containing the GAP gene of S. cerevisiae (Yamano et al., Journal of Biotechnology, 32, 165–171, 1994) as a DNA fragment containing most of the GAP gene. This fragment was labeled with $^{32}P$ and hybridization was carried out using this fragment as a probe. As a result, three positive plaques were isolated. A phage DNA of one of these plaques was subcloned and a 6.5-kb EcoRI fragment contained in this phage DNA was isolated and then integrated at the EcoRI site of the plasmid vector pBluescript IISK+ to construct plasmids pGAP1 and pGAP2 (FIG. 19).

(2) Construction of Plasmids Containing the GAP Gene Promoter/Terminator

The promoter and terminator fragments of the C. utilis glyceraldehyde-3-phosphate hydrogenase (GAP) gene were obtained by PCR using the plasmid pGAP1 as a template. For the promoter, a 974-bp fragment from −976 upstream of the initiation codon to −1 immediately before the initiation codon (where A in the initiation codon is +1) was obtained using the following primers.

5'-AGCGGCCGCTAGCTTACAGCGAGCACTCAAATCTGCCC-3' (SEQ ID NO: 30)

5'-GGGATCCTCTAGATATGTTGTTTG-TAAGTGTGTTTTGTATC-3' (SEQ ID NO: 31)

In these primers, a NotI site was added to the end of the 5'-side primer and a XbaI and BamHI sites were added immediately before the 3'-side initiation codon. A 723-bp fragment from +1006 to +1728 immediately after the termination codon was obtained as the terminator. The following primers were used, and a BamHI site was added immediately after the termination codon at the 5' side and a PstI site was added to the 3' side.

5'-GGGGATCCATTGTATGACTTTTATTTATGG-3' (SEQ ID NO: 32)

5'-CCCTGCAGGGATYAAAGCTGAAGAATAAT-3' (SEQ ID NO: 33)

Two amplified fragments thus obtained were cloned into plasmid pT7Blue using the TA cloning kit (Invitrogen). These two fragments were obtained as a NotI-BamHI fragment and a BamHI-PstI fragment, which were then cloned between the NotI and PstI sites of the pBluescript SK− to construct plasmid pGAPPT10 (FIG. 20).

(3) Construction of the Plasmids for Expression of the Monellin Gene and Transformation The monellin gene was excised as a DraI-BglII fragment from the plasmid pMNY1 containing a synthetic DNA sequence corresponding to the amino acid sequence shown in SEQ ID NO: 5. Briefly, pMNY1 can be obtained by inserting a chemically synthesized DNA fragment corresponding to the amino acid sequence of SEQ ID NO: 5 between the EcoRI site and the HindIII site of pUC18 (Pharmacia) (see Japanese Patent Laid-open 1993/70494). The plasmid pGAPPT10 was digested with XbaI, treated with Klenow enzyme to create blunt ends, then further digested with BamHI. The resulting fragment was ligated with the DraI-BglII fragment containing the monellin gene to construct plasmid pGAPM3 (FIG. 20). Furthermore, the NotI-PstI fragments excised from pGAPM3 were ligated into the PstI and NotI sites of plasmids pCLR215, pCLR216, pCLR217, pCRAL10, pCRAL11, pURAL10, and pURAL11 described in Example 2 to construct plasmids pCLRM215, pCLRM216, pCLRM217, pRM10, pRM11, pUM10, and pUM11 (FIG. 20). These seven kinds of plasmids thus constructed were digested with BglII and then used for transformation of C. utilis strain ATCC9950 by the electric field pulse method as described in Example 1. As a result, transformants with pCLRM215, pCLRM216, pRM10, pRM11, pUM10, and pUM11 were obtained. No transformant was obtained for pCLRM217.

Example 10

Expression of Monellin in Yeast Transformants

Four strains each of the transformants with pCLRM215, pCLRM216, pRM10, pRM11, pUM10, and pUM11 were cultured in 10 ml of YPD medium for 24 hours with shaking. Cells were collected by centrifugation, suspended in 50 mM Tris (pH 7.5), 15 mM NaCl, 1 mM DTT, and 1 mM PMSF, and then disrupted by vortexing with glass beads. Cell debris and insoluble precipitates were removed by centrifugation at 15,000×g for 10 minutes to derive soluble proteins. The soluble proteins thus prepared were subjected to 15/25% SDS-PAGE and the expression was analyzed. A band was found for all plasmids at a position corresponding to a molecular weight of about 10,000 which corresponds to monellin. The results further showed that transformants with high-copy-type pCLRM215, pCLRM216, pRM11, and pUM11 were expressed at a remarkably higher level as compared to transformants with low-copy-type pRM10 and pUM10. Whole soluble proteins of two strains each of C. utilis transformants with pCLRM216, pRM11 and pUM11 were subjected to electrophoresis on 15/25% SDS-PAGE. Results are shown in FIG. 21 (1).

As a control, transformants with plasmid pCLRE4 containing the rDNA fragment and the cycloheximide-resistance L41 gene were similarly treated. The pCLRE4 was constructed by inserting a 3.5-kb EcoRI fragment obtained from pCRE2 (FIG. 2) described in Example 2 into the EcoRI site of the plasmid pCLBS12 (FIG. 11) described in Example 6. The gel was stained with Coomassie Brilliant Blue after electrophoresis, dried and then scanned by a densitometer to calculate the percentage of monellin in the total soluble proteins. It was found that monellin had accumulated to a level of about 50% of the cellular soluble proteins in C. utilis transformants with pCLRM216, pRM11 and pUM11, and that the expression level tended to increase in transformants with pUM11 and pRM11 in which sequences derived from bacteria were deleted.

On the other hand, monellin expression in yeast S. cerevisiae was studied using yeast TD4 (a mutant strain (a, his, ura, leu, tryp) of S. cerevisiae S288c (ATCC 26108)) (see Japanese Patent Laid-open 1993/70494) which was transformed with the plasmid pCTMNY1 containing an expression cassette consisting of "GAP promoter+monellin gene+PGK terminator" and the TRP1 gene as a marker, and the full length of yeast 2 μm DNA. Two strains of transformants thus transformed were cultured in 10 ml of SD medium (0.67% yeast nitrogen base (free of amino acid), 2% glucose) containing histidine, uracil and leucine (20 μg/ml each) at 30C for 24 hours with shaking.

Furthermore, cells of the parent strain TD4 were similarly cultured in the abovementioned medium supplemented with tryptophan. Soluble protein fractions were prepared and subjected to electrophoresis on 15/25% SDS-PAGE. Results are shown in FIG. 21 (2). Monellin expression was calculated to be about 5% of the total soluble protein by quantitative densitometer measurements. It was shown that the level of monellin expression of S. cerevisiae transformants with pCTMNY1 was remarkably low as compared to expression of C. utilis transformants in spite of the fact that monellin was expressed in S. cerevisiae transformants with YEp-type plasmids deemed to be present in more than 50 copies per cell using the powerful GAP promoter. Furthermore, the amount of monellin expressed was about 10% of the cellular proteins when the monellin gene was expressed in E. coli under the control of the TRP gene promoter (see Japanese Patent Laid-open 1993/70494). From these results, it was revealed that C. utilis is a suitable host for the expression of heterologous proteins.

DNAs were prepared from the four clones, the transformants obtained with pCLRM216, pRM11, and pUM11 and subjected to Southern blot analysis. The DNAs for pCLRM216 and pRM11 were digested with PstI+EcoRI, the DNA for pUM11 was digested with HindIII, and a 0.6-kb ClaI-HindIII L41 gene fragment was used as a probe for the analysis. The number of copies of the integrated plasmids was estimated assuming that the intensity of the band derived from the endogenous L41 gene corresponds to 2 copies. The intensity of the bands was measured using a BAS 2000 imaging analyzer (Fiji Film). The calculated numbers of copies of the integrated plasmids were 10 to 19 copies for the pCLRM216 transformants, 12 to 18 copies for the pRM11 transformants, and 17 to 27 copies for the pUM11 transformants.

Southern blot analysis with the same filter using pUC19 as a probe showed that no DNA sequence from bacteria was integrated into the chromosome for the pRM11 and pUM11 transformants.

Figure 22:
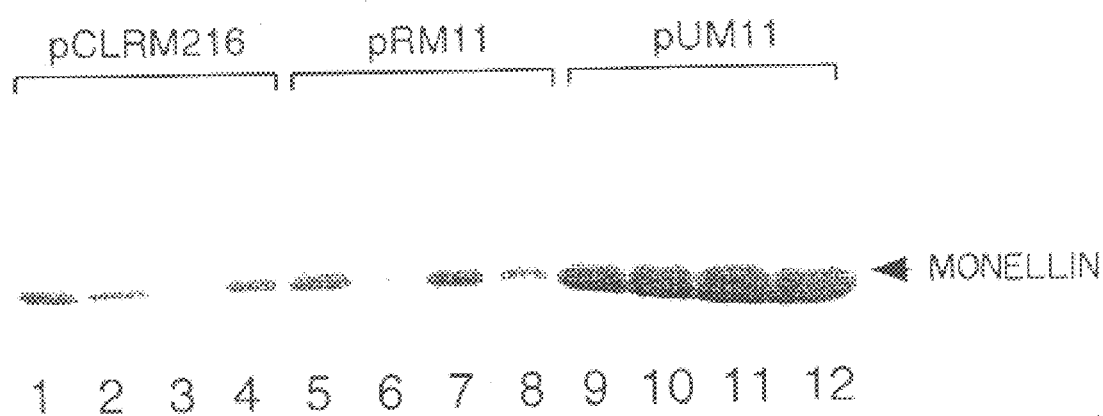
FIG. 22 is a photograph showing results of the analysis of soluble proteins of C. utilis transformants with plasmids pCLRM216, pRM11, and pUM11 after 50 generations of growth, using SDS-polyacrylamide gel electrophoresis.

The four clones each of the pCLRM216, pRM11, and pUM11 transformants were consecutively subcultured in YPD liquid medium to study the stability of the integrated genes. First, cells grown on YPD plate supplemented with cycloheximide were inoculated into 10 ml of YPD liquid medium and cultured to the stationary phase. Then, 10 μl of the resulting culture was inoculated into 10 ml of fresh YPD liquid medium and then cultured to the stationary phase. Subcultures in this nonselective medium were repeated four times for about 50 generations of growth. Cells were collected from the last culture, suspended in 50 mM Tris (pH 7.5), 150 mM NaCl, 1 mM DTT, and 2 mM PMSF, and disrupted by vortexing with glass beads to prepare soluble proteins. The whole soluble proteins from the four clones each of pCLRM216, pRM11, and pUM11 transformants were subjected to 15/25% SDS-PAGE. Results are shown in FIG. 22.

The results show that the level of monellin expression decreased in the strains transformed with pCLRM216 and pRM11, though it was variable, while no marked decrease was observed in the four clones transformed with pUM11. Furthermore, the subculture of 50 generations was diluted and plated on YPD plates and YPD plates supplemented with 40 μg/ml cycloheximide. After incubation for 2 days at 30° C., colonies were counted to estimate the ratio of cells grown on the latter plates to cells-grown on the former plates. Results were 0, 2.0, 2.3 and 4.0% for the four clones of pCLRM216 transformants, 1.0, 1.0, 4.7 and 7.2% for the four clones of pRM11 transformants, and 97.0, 100, 40.2 and 43.5% for the four clones of pUM11 transformants, which showed that pUM11 was extremely stable as compared to the other two plasmids. These results showed that the plasmid pUM11 was particularly superior among the developed vectors in terms of its expected copy number and stability, although observed ratios do not exactly reflect the retention capability of the plasmid because the cells could become cycloheximide sensitive even if only a part of the integrated plasmid is lost from the chromosome.

Example 11

Purification of Monellin

The pUM11 transformants were incubated in YPD medium at 30° C. overnight with shaking and then the resulting cells were collected by centrifugation. To about 10 g by wet weight (corresponding to 2 g by dry weight) of the cells, 17 ml of 0.9 M sorbitol were added, and the resulting cell suspension was incubated at 37° C. for 30 minutes with an addition of 6 ml of Zymolyase 100T (Seikagaku Corp.) with stirring. The cell suspension was treated with a french press (1,000 psi, 3 times) to disrupt the cells. A supernatant fraction was obtained by centrifugation (10,000×g, 20 minutes). The precipitate fraction was washed three times with a sodium phosphate buffer solution (10 mM sodium phosphate (pH 7.0), 100 mM NaCl) to collect another supernatant fraction, which was combined with the previously obtained supernatant fraction. This fraction thus combined was called the french press-treated sample. Similarly, in order to compare disruption efficiency, 10 g (by wet weight) of the cells were destroyed with dynomill for 15 minutes while cooling with 40 ml of a sodium phosphate buffer solution (10 mM sodium phosphate (pH 7.0), 100 mM NaCl) and 60 ml of glass beads (425 to 600 microns, Sigma). A supernatant fraction of this crushed material was collected. The glass beads were thoroughly washed with the abovementioned buffer solution until no protein was extracted. This wash and the previously obtained supernatant fraction were combined, which was called the dynomill-treated sample. The french press-treated fraction and the dynomill-treated fraction were subjected to SDS-PAGE to compare the efficiency of monellin extraction. Results showed there was no significant difference between the two treatments.

Preliminary experiments on acid and heat treatments for monellin purification were performed. The dynomill-treated sample was diluted to a protein concentration of 1.5 mg/ml (all the proteins were quantified by a Bio-Rad protein assay kit using BSA as a standard). Acid treatment was carried out by adjusting the pH of the sample to 4, 4.5, or 5.5 with the addition of a 40 mM sodium acetate buffer solution and maintaining the solution at 4° C. for 12 hours. Heat treatment was carried out by heating the sample at 50° C., 60° C., or 70° C. for 10 minutes. Results showed that undesirable proteins derived from yeast, other than monellin, were copiously precipitated by the acid treatment at pHs 4 and 4.5 or by the heat treatment at 60° C. for 10 minutes.

Figure 23:
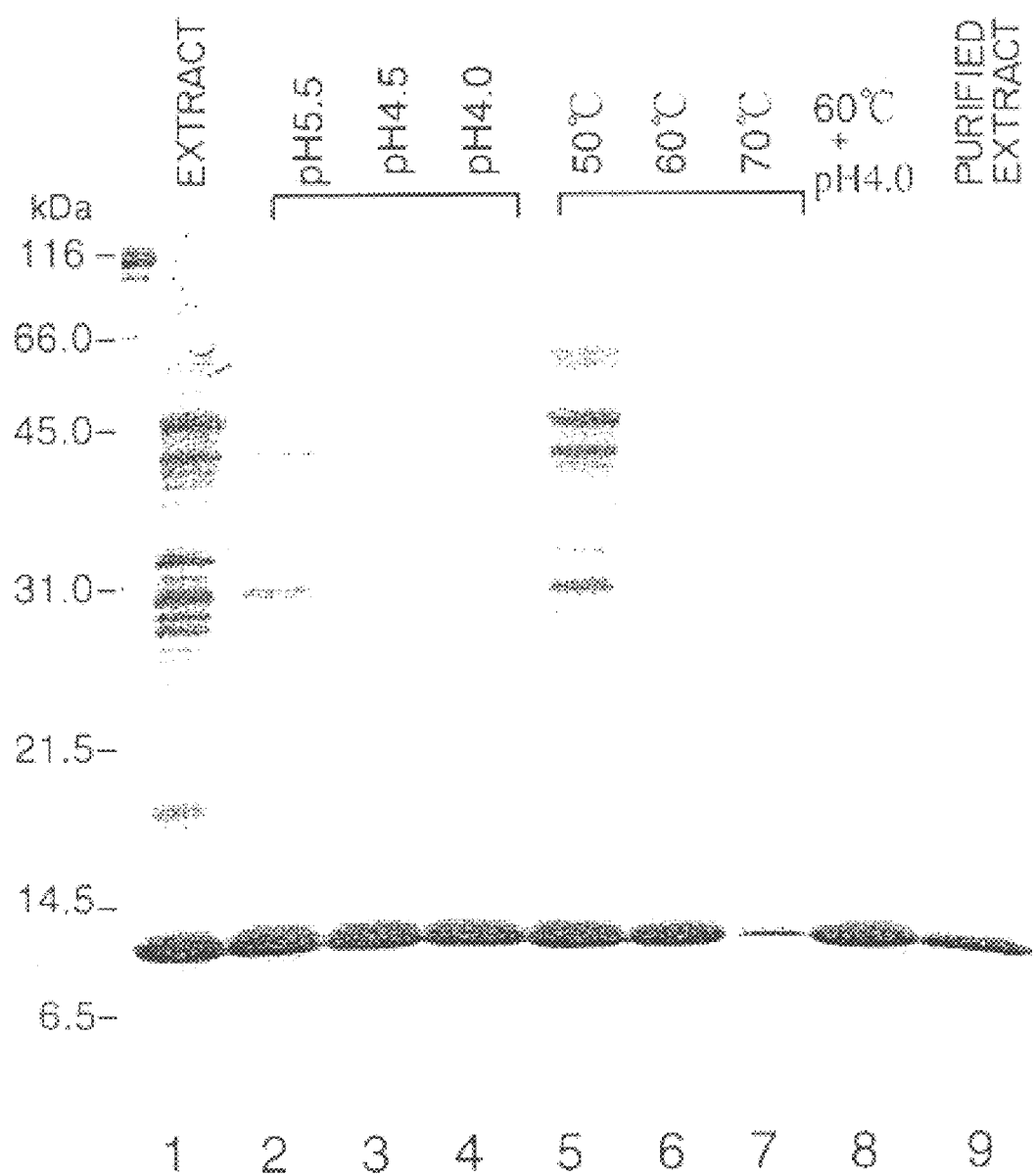
FIG. 23 is a photograph showing results of the analysis of samples of soluble proteins prepared from C. utilis transformants with plasmid pRM11, which were heat-treated or acid-treated, or purified by column chromatography, using SDS-polyacrylamide gel electrophoresis.

It was also found that heat treatment at 50° C. for 10 minutes was not effective, and that heat treatment at 70° C. for 10 minutes precipitated monellin along with other proteins. Furthermore, it was found that nearly 100% of non-monellin proteins could be removed by combining the heat treatment at 60° C. for 10 minutes and the acid treatment at pH 4. Results of SDS-PAGE is shown in FIG. 23.

Based on these experimental results, monellin was purified using the french press-treated sample. The french press-treated sample was diluted with a sodium phosphate buffer solution (10 mM sodium phosphate (pH 7.0), 100 mM NaCl) to adjust the protein concentration to about 2.0 mg/ml and then heated at 50 C. for 10 minute in a water bath. After removing the precipitates by centrifugation, the pH of the resulting solution was adjusted to 4.5 by adding 200 mM sodium acetate buffer (pH 3.0) with stirring, and acid treatment was carried out while cooling. After treatment for about 1 hour, the pH was adjusted to 6.0 by the addition of 200 mM sodium phosphate buffer (pH 7.0). After removing the precipitates by centrifugation, the supernatant fraction was concentrated by ultrafiltration (molecular weight 3,000 cut), then dialyzed against 10 mM sodium phosphate buffer (pH 7.0) overnight. The insoluble fraction was removed by centrifugation followed by filtration through a 0.2 micron filter (Millipore), after which the resulting fraction was passed through a column (50 ml) of CM-Sepharose (Pharmacia) equilibrated with the buffer. The unadsorbed fraction was eluted with the same buffer and the target protein was obtained with a linear gradient of 0 to 0.4 M NaCl solution (150 ml). This target protein was subjected to SDS-PAGE, and with the presence of a single band on the gel, was confirmed to be purified (see FIG. 23).

The circular dichroism spectrum (wave length from 190 nm to 260 nm) of natural monellin shows a strong negative spectrum near 212 nm and a positive spectrum at near 236 nm. A circular dichroism spectrum of the purified recombinant monellin was very similar to that of natural monellin.

Purified single-chain monellin and natural monellin samples were each dissolved in pure water to concentrations of 0.3 $\mu g/\mu l$, 0.2 $\mu g/\mu l$, 0.1 $\mu g/\mu l$, 0.05 $\mu g/\mu l$, and 0.02 $\mu g/\mu l$ and 10 $\mu l$ of each solution were used to evaluate sweetness by a taste test on the tongue.

The sweetness threshold concentrations for the natural and recombinant were the same, 0.05 to 0.1 $\mu g/\mu l$ (i.e., 0.5 to 1 $\mu g$ protein), indicating that monellin produced in yeast had a specific activity equivalent to that of natural monellin.

Example 12

Synthesis of the Amylase Gene

The amino acid sequence encoded by the amylase gene derived from *Sulfolobus solfataricus* KM1 (Kobayashi K. et al., Biosci. Biotech. Biochem., 60(10), 1720–1723, 1966), was converted to the DNA sequence using those codons, except those for methionine and tryptophan, most frequently used in the glyceraldehyde-3-phosphoric acid dehydrogenase (GAP) gene of *C. utilis*. The DNA sequence was designed such that the variation in codons for each amino acid contained in the gene would be as close as possible to that for GAP, that specific restriction enzyme sites would be formed at intervals of about 180 to 320 bases, and that the gene would be constructed as a group of several segments. Some minor codons were also used to conveniently form the restriction enzyme cleavage sites. In addition, the sequence was designed to have an XbaI recognition site on the 5' upstream side one base distant from the translation initiation codon (ATG) of the structural gene and a BglII recognition site on the 3' downstream side one base distant from the translation termination codon. Taking these design parameters into consideration, the gene encoding the amylase from *S. solfataricus* KM1 was constructed to consist of seven segments, A-1 to A-7 (SEQ. ID. NOS: 7 to 13). Each segment has specific restriction enzyme recognition sites at both ends and additional two nonsense nucleotides at both ends of the restriction enzyme recognition sites to enable each segment to be digested directly by the restriction enzymes. Primers used in the synthesis of each segment are shown in FIGS. 24, 25 and 26.

Segment A-1 (SEQ ID NO: 7), a 288-bp fragment having XbaI and StyI sites at both ends was made from four oligonucleotides. First, PCR was carried out using primers A-1-2 and A-1C-2. Another PCR was carried out using the reaction solution obtained by this PCR as a template using primers A-1-1 and A-1C-1 to obtain a 282-bp double-stranded DNA.

Segment A-2 (SEQ ID NO: 8), a 312-bp fragment having StyI and AccI sites at both ends, was also made from four oligonucleotides. First, PCR was carried out using primers A-2-2 and A-2C-2. Another PCR was carried out using the synthesized double-stranded DNAs as a template using primers A-2-1 and A-2C-1 to obtain a 312-bp fragment.

Segment A-3 (SEQ ID NO: 9), a 241-bp fragment having AccI and XhoI sites at both ends, was also made from four oligonucleotides. First, PCR was carried out using primers A-3-2 and A-3C-2. Another PCR was carried out using the synthesized double-stranded DNA as a template using primers A-3-1 and A-3C-1 to obtain a 214-bp fragment.

Segment A-4 (SEQ ID NO: 10), a 214-bp fragment having XhoI and EcoRV sites at both ends, was also made from four oligonucleotides. First, PCR was carried out using primers A-4-2 and A-4C-2. Another PCR was carried out using the synthesized double-stranded DNA as a template using primers A-4-1 and A-4C-1 to obtain a 214-bp fragment.

Segment A-5 (SEQ ID NO: 11), a 184-bp fragment having EcoRV and SalI sites at both ends, was made from two oligonucleotides. PCR was carried out using primers A-5-1 and A-5C-1 to obtain a 184-bp fragment.

Segment A-6 (SEQ ID NO: 12), a 241-bp fragment having SalI and CClaI sites at both ends, was also made from four oligonucleotides. First, PCR was carried out using primers A-6-2 and A-6C-2. Another PCR was carried out using the synthesized double-stranded DNA as a template using primers A-6-1 and A-6C-1 to obtain a 241-bp fragment.

Segment A-7 (SEQ ID NO: 13), a 284-bp fragment having ClaI and BglII sites at both ends, was also made from four oligonucleotides. First, PCR was carried out using primers A-7-2 and A-7C-2. Another PCR was carried out using the synthesized double-stranded DNA as a template using primers A-7-1 and A-7C-1 to obtain a 284-bp fragment.

The seven fragments thus amplified were cloned into pT7Blue vector (Invitrogen), or the HincII site of pUC118 after treated with a Klenow enzyme and phosphorylated. DNA sequence of these seven fragments were determined and confirmed to be identical to the designed sequences. These fragments were digested with individual restriction enzymes which recognized respective ends, recovered using a low melting point agarose gel (FMC BioProducts), and then purified using β-Agarase-I (Japan Gene).

These seven fragments were ligated with each other as follows: Three fragments, segments A-1, A-2, and A-3 were simultaneously inserted into the XbaI and XhoI sites of pBSiIKS +. The resulting plasmid was named pAmy 123. XbaI and XhoI fragments containing segments A-1, A-2, and A-3 were recovered from this plasmid and inserted between the XbaI and EcoRV sites of pBSIIKS + along with segment A-4, i.e., the XhoI-EcoRV fragment. The resulting plasmid was named pAmy1234. The XbaI-EcoRV fragment containing segments A-1 to A-4 was recovered from this plasmid and inserted between the XbaI and SalI sites of pBSIIKS + along with an EcoRV-SalI fragment containing segment A-5. This plasmid was named pAmy12345. A vector (called pBSBg1) was prepared by inserting BglII linkers (CAGATCTG) at the SmaI site of pBSIIKS +. Segments A-6 and A-7 were inserted between the BglII and SalI sites of this vector. The resulting plasmid was named pAmy 67. The HindIII and PstI sites of pUG12 were treated with Klenow enzyme and BglII linkers (CAGATCTG) were inserted; the resulting vector (called pUC12BglII) was digested with XbaI and BglII. The XbaI-SalI region containing segments A-1 to A-5 from the abovementioned pAmy12345 and the SalI-BglII region containing segments A-6 and A-7 from pAmy67 were simultaneously inserted into this plasmid and thus the synthesis of the gene encoding the amylase from *S. solfataricus* KM1 strain (SEQ ID NO: 14) was completed.

Example 13

Construction of the Amylase Expression Cassette and Transformation

Figure 27:
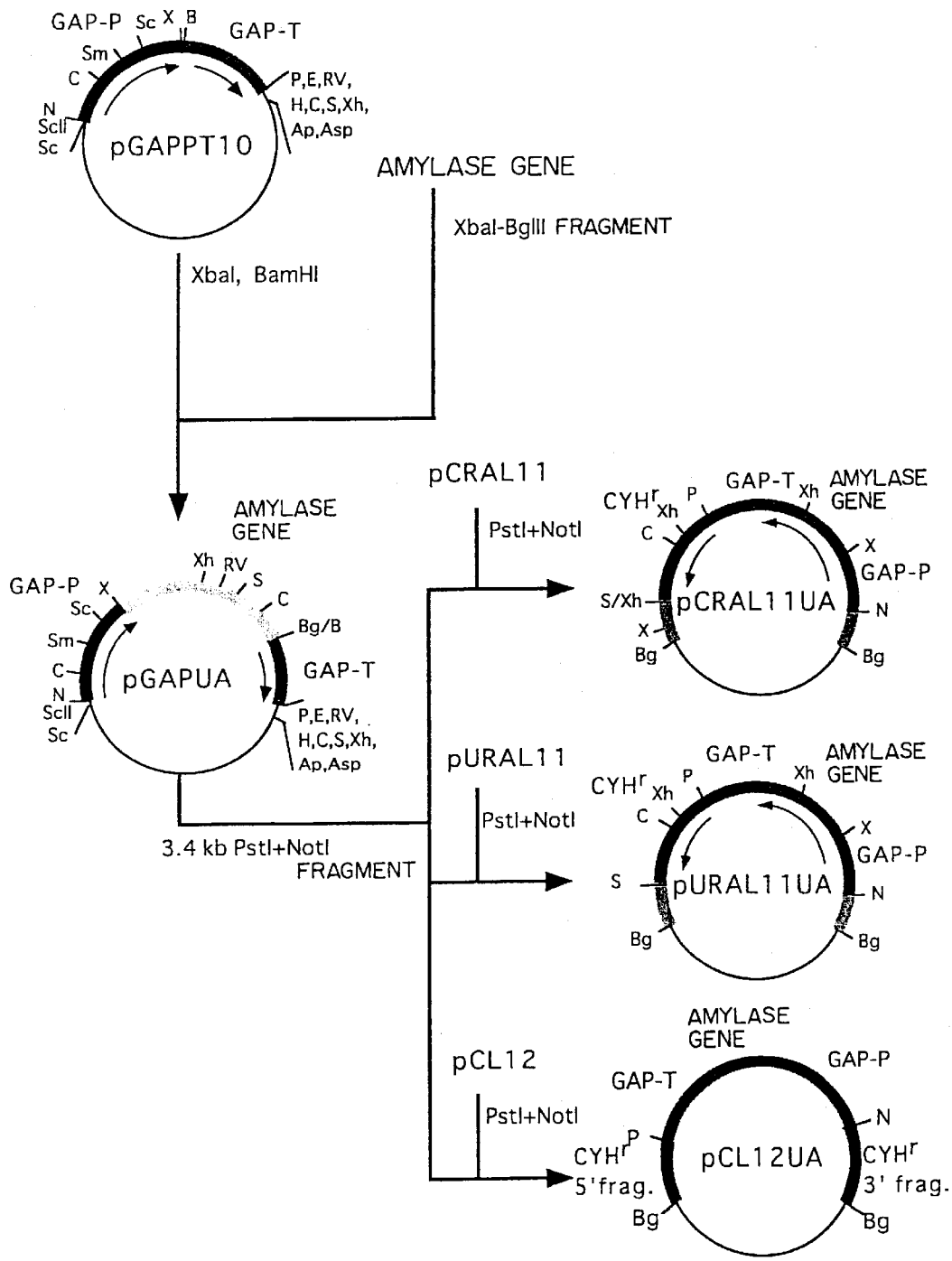
FIG. 27 shows the construction of plasmids pCRAL11UA, pURAL11UA, and pCL12UA.

The XbaI-BglII fragment of the gene encoding amylase derived from *S. solfataricus* KM1 strain was inserted between the XbaI and BamHI sites of pGAPPT10. This plasmid was named pGAPUA. An approximately 3.4-kb expression cassette containing the amylase gene flanked by the GAP promoter and the GAP terminator was recovered as a NotI-PstI fragment. This approximately 3.4-kb fragment derived from pGAPUA was inserted at the PstI/NotI sites of pURAL11, pCRAL11, and pCL12 obtained in Example 8 to construct plasmids pURAL11UA, pCRAL11UA, and pCL12UA, respectively (FIG. 27). After digesting these plasmids with restriction enzyme BglII, cells of *C. utilis* ATCC9950 were transformed by the electric pulse method as described in Example 7. Conditions for pulsing were a capacitance of 25 μF, resistance of 1,000 ohms, and voltage of 5 KV/cm.

Example 14

Expression of Amylase in Yeast Transformants

Figure 28:
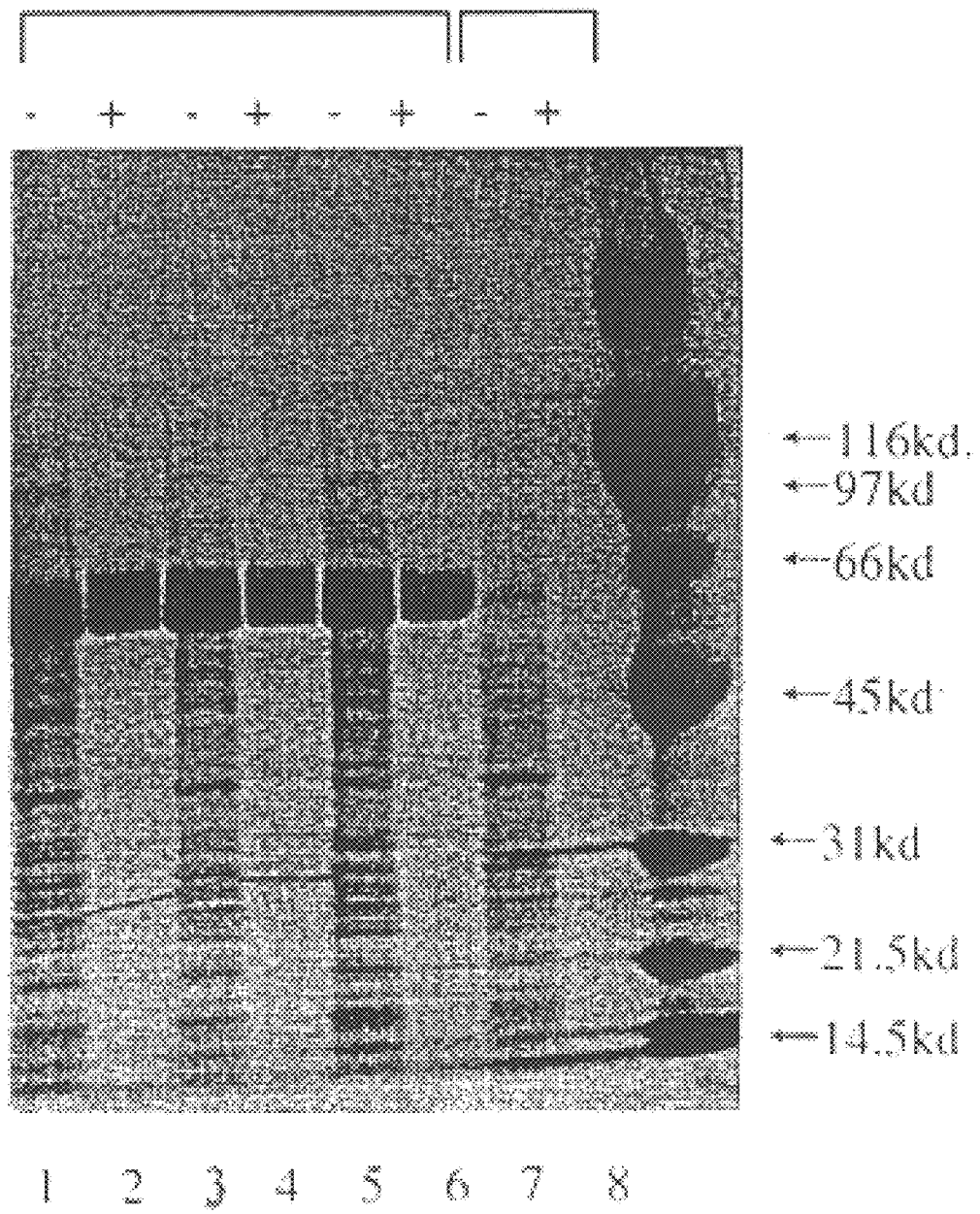
FIG. 28 is a photograph showing results of the analysis of soluble proteins of C. utilis transformants with plasmids pCLRE4 and pURAL11UA, using SDS-PAGE. +: Heat-treated sample; −: non-heated sample.

The transformants with plasmids pURAL11UA, pCRAL11UA, and pCL12UA were cultured in YPD liquid medium for one day, after which soluble proteins were extracted from the collected cells according to the method described in Example 10 and were subjected to SDS-PAGE. In all cases, amylase had accumulated in an amount more than 50% of the soluble proteins. Soluble proteins extracted from three transformants with pURAL11UA and one transformant with a plasmid containing the cycloheximide-resistance gene (pCLRE2) were subjected to 4/20% SDS-PAGE. Since the present amylase is thermostable, samples of these soluble proteins were heated at 70 C. for 30 minutes and were similarly subjected to 4/20% SDS-PAGE. Results are shown in FIG. 28. The heat-treated samples showed the same specific amylase activity as that derived from *S. solfataricus* KM1 strain. There was not much difference between amylase production calculated from the activity based on the specific activity of the purified enzyme standard preparation and the production estimated from the results of SDS-PAGE, which indicated that the amylase produced in the yeast cells was of the active form.

Furthermore, transformants with pCRAL11UA, pURAL11UA, and pCL12UA were cultured for about 50 generations in a nonselective medium according to the method described in Example 10 to study the stability of the integrated genes. Results showed that production markedly decreased in 3 out of 5 clones transformed with pCRAL11UA which used rDNA as the target for integration, while the production did not markedly change in the clones transformed with pURAL11UA and pCL12UA which used the URA3 gene locus and the L41 gene locus respectively, as the target for integration. These results demonstrated that the plasmids integrated using the L41 gene locus as the target for integration were of equal excellence in high level expression of the gene by high-number-copy integration and in degree of stability as those integrated using the URA3 gene locus as the target.

Example 15

Expression of GIF

Human glycosylation inhibiting factor (GIF) is a protein mainly produced in T cells. Comprised of 115 amino acids, it has a molecular weight of 12,500 and is known to have immuno suppressive activity (Mikayama et al., Proc. Natl. Acad. Sci., USA, 90, 10056–10060, 1993). A 348-bp DNA was synthesized based on this amino acid sequence using codons most frequently used in *C. utilis*. An NheI site was added to the 5' end and a BglII site was added to the 3' end.

Figure 29:
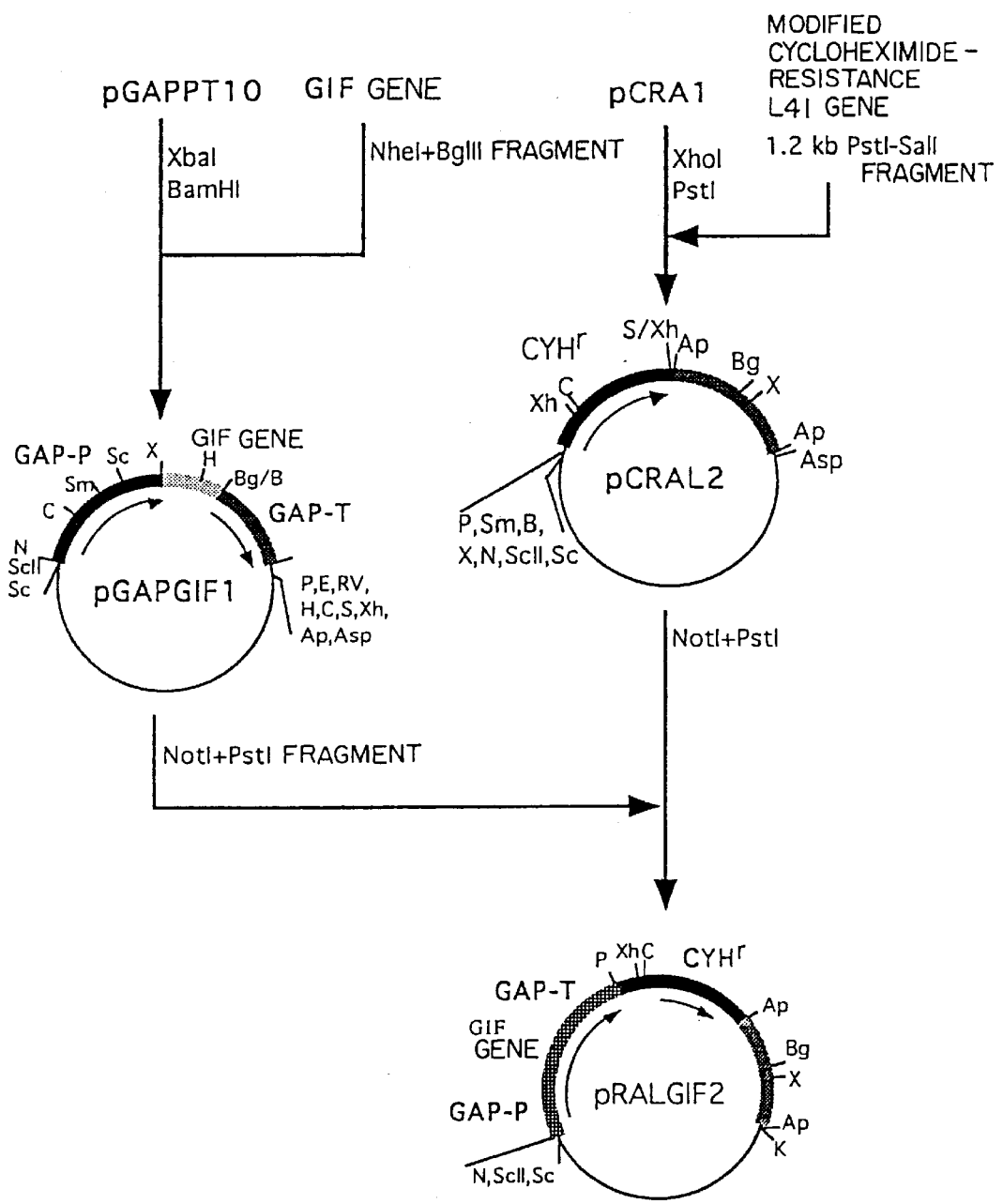
FIG. 29 shows the construction of plasmid pRALGIF2.

The resulting 350-bp fragment was ligated with plasmid pGAPPT10 (Example 3) digested with XbaI and BamHI to construct pGAPGIF1 (FIG. 29).

Also, the 1.2-kb PstI-SalI cycloheximide-resistance L41 gene fragment described in Example 2 was inserted between the XhoI and PstI sites of plasmid pCRA1 to construct plasmid pCRAL2. A GAP promoter+GIF gene+GAP terminator fragment which was excised from plasmid pGAPGIF1 as a NotI-PstI fragment was inserted between the NotI and PstI sites of this plasmid pCRAL2 to construct plasmid pRALGIF2 (FIG. 29).

This plasmid was digested at the BglII site within the rDNA fragment, then cells of C. utilis ATCC 9950 were transformed by the electric pulse method as described in Example 7. Cells of eight clones of the resulting transformants were cultured in 10 ml of YPD medium for 24 hours with shaking. The cells were collected by centrifugation, suspended in 50 mM Tris (pH 7.5), 150 mM NaCl, 1 mM DTT, and 1 mM PMSF, and disrupted by vortexing with glass beads. Cell debris and insoluble precipitates were removed by centrifugation at 15,000×g for 10 minutes to prepare soluble proteins. The resulting soluble proteins were subjected to electrophoresis on 15% to 25% SDS-PAGE to study GIF expression. Results showed the presence of a band at a position corresponding to a molecular weight of about 12,000 which corresponds to GIF.

We claim:

1. A method for transforming *Candida utilis,* comprising the steps of transforming cells of *C. utilis* with a vector that comprises a marker gene for selecting transformants, a shortened promoter sequence that is operably linked to the marker gene, and a homologous DNA sequence that is homologous to chromosomal DNA, other than an rDNA sequence, of *Candida utilis,* and optionally a heterologous gene or a gene isolated from *C. utilis,* wherein the vector is linearized by cleaving within or at both ends of the homologous DNA sequence with a restriction enzyme, wherein the heterologous gene or gene isolated from *Candida utilis* can be integrated into the chromosomal DNA of *Candida utilis* by homologous recombination, and wherein the shortened promoter is a promoter truncated at its 5' terminus to decrease, relative to pCLRE11, the transformation frequency of the vector in host cells of *Candida utilis* and to increase, relative to pCLRE11, copy number of the vector in host cells of *Candida utilis* and then selecting the resulting transformants which show drug resistance.

2. The method of claim 1, wherein the vector is integrated into the *Candida utilis* chromosome and is stably maintained in the chromosome.

3. The method of claim 1, wherein the homologous sequence and, optionally, a DNA sequence comprising the marker gene, the shortened promoter sequence and the heterologous gene or the gene isolated from *Candida utilis,* flanked at both ends by the homologous sequence are integrated into the *Candida utilis,* chromosome and are stably maintained in the chromosome.

4. The method of claim 1, wherein the marker gene is a modified cycloheximide-resistance L41 gene.

5. The method of claim 1, wherein *Candida utilis* is selected from the group consisting of ATCC9256, ATCC9226 and ATCC9950.

6. The method of claim 1, wherein the marker gene, the shortened promoter sequence, and the heterologous gene or the gene isolated from *Candida utilis* are flanked at both ends by the homologous DNA sequence.

7. The method of claim 1, wherein the shortened promoter sequence is isolated from *Candida utilis.*

8. The method of claim 1, wherein the shortened promoter sequence is isolated from the L41 gene of *Candida utilis,* a phosphoglyceric acid kinase (GAP) gene or a plasma membrane proton ATPase (PMA) gene.

9. The method of claim 1, wherein the shortened promoter sequence is isolated from the L41 gene of *Candida utilis.*

10. The method of claim 9, wherein the shortened promoter sequence is a sequence which comprises the DNA sequence of nucleotide X-192 of SEQ ID NO: 1, wherein X represents an integer 1 to 111.

11. The method of claim 9, wherein the shortened promoter sequence is a sequence selected from the group consisting of SEQ ID NO: 1, SEQ ID NO: 2, and SEQ ID NO: 3.

12. The method of claim 1, wherein the homologous DNA sequence is selected from the group consisting of the URA3 gene sequence, the L41 gene sequence, the PGK gene sequence, the GAP gene sequence, the PMA gene sequence, and partial DNA sequences thereof.

13. The method of claim 1, wherein the homologous DNA sequence is the URA3 gene sequence or a partial DNA sequence thereof.

14. The method of claim 1, wherein the marker gene is a drug-resistance marker gene.

15. The method of claim 14, wherein the drug-resistance marker gene is a gene conferring cycloheximide resistance.

16. The method of claim 1, wherein the heterologous gene is a gene coding for a protein or a peptide selected from the group consisting of a single-chain monellin, glycosylation inhibiting factor (GIF), serum albumin, α- or β-globulin, factor VIII, factor IX, fibronectin, α-1-antitrypsin, interleukin, interferon, G-CSF, GM-CSF, PDGF, EFG, FGF, erythropoietin, thrombopoietin, insulin, antigen polypeptides isolated from viruses for vaccine production, proteins having immune suppression activity, chymosin, amylase, lipase, cellulase, protease and pectinase.

17. The method of claim 1, wherein the heterologous gene is a single-chain monellin gene.

18. The method of claim 17, wherein the single-chain monellin gene comprises a DNA sequence coding for the amino acid sequence of SEQ ID NO: 5 or the amino acid sequence of SEQ ID NO: 6.

19. A *Candida utilis* transformant which is transformed with a vector comprising a marker gene for selecting transformants, a shortened promoter sequence that is operably linked to the marker gene, and a homologous DNA sequence that is homologous to chromosomal DNA, other than an rDNA sequence, of *Candida utilis,* and optionally a heterologous gene or a gene isolated from *C. utilis,* wherein the vector is linearized by cleaving within or both ends of the homologous DNA sequence with a restriction enzyme, wherein the heterologous gene or gene isolated from *Candida utilis* can be integrated into the chromosomal DNA of *Candida utilis* by homologous recombination, and wherein the shortened promoter is a promoter truncated at its 5' terminus to decrease, relative to pCLRE11, the transformation frequency of the vector in host cells of *Candida utilis* and to increase, relative to pCLRE11, copy number of the vector in host cells of *Candida utilis.*

20. The transformant of claim 19, wherein the marker gene, the shortened promoter sequence, and the heterologous gene or the gene isolated from *Candida utilis* are flanked at both ends by the homologous DNA sequence.

21. The transformant of claim 19, wherein the shortened promoter sequence is isolated from *Candida utilis.*

22. The transformant of claim 19, wherein the shortened promoter sequence is isolated from the L41 gene of *Candida utilis,* a phosphoglyceric acid kinase (GAP) gene, or a plasma membrane proton ATPase (PMA) gene.

23. The transformant of claim 11 wherein the shortened promoter sequence is isolated from the L41 gene of *Candida utilis.*

24. The transformant of claim 23, wherein the shortened promoter sequence is a sequence which comprises the DNA sequence of nucleotide X-192 of SEQ ID NO: 1 wherein X represents an integer 1 to 111.

25. The transformant of claim 23, wherein the shortened promoter sequence is a sequence selected from the group consisting of SEQ ID NO: 1, SEQ ID NO: 2, and SEQ ID NO: 3.

26. The transformant of claim 19, wherein the homologous DNA sequence is selected from the group consisting of the URA3 gene sequence, the L41 gene sequence, the PGK gene sequence, the GAP gene sequence, the PMA gene sequence, and partial DNA sequences thereof.

27. The transformant of claim 19, wherein the homologous DNA sequence is the URA3 gene sequence or a partial DNA sequence thereof.

28. The transformant of claim 19, wherein the marker gene is a drug-resistance marker gene.

29. transformant The of claim 28, wherein the drug-resistance marker gene is a gene conferring cycloheximide resistance.

30. The transformant of claim 29, wherein the gene conferring cycloheximide resistance is a modified cycloheximide-resistance L41 gene.

31. The method of claim 1 wherein the heterologous gene is a gene coding for a protein or a peptide selected from the group consisting of a single-chain monellin, glycosylation inhibiting factor (GIF), serum albumin, α-or β-globulin, factor VIII, factor IX, fibronectin, α-1-antitrypsin, interleukin, interferon, G-CSF, GM-CSF, PDGF, EFG, FGF, erythropoietin, thrombopoietin, insulin, antigen polypeptides isolated from viruses for vaccine production, proteins having immune suppression activity, chymosin, amylase, lipase, cellulase, protease and pectinase.

32. The method of claim 31, wherein the heterologous gene is a single-chain monellin gene.

33. The method of claim 17, wherein the single-chain monellin gene comprises a DNA sequence coding for the amino acid sequence of SEQ ID NO: 5 or the amino acid sequence of SEQ ID NO: 6.

34. The *Candida utilis* transformant of claim 19 wherein the heterologous gene is a single-chain monellin gene which is optionally modified to be highly expressed in *C. utilis*.

35. The *Candida utilis* transformant of claim 19 wherein the heterologous gene is an amylase gene which is optionally modified to be highly expressed in *C. utilis*.

36. The *Candida utilis* transformant of 19 Wherein *Candida utilis* is selected from the group Consisting of ATCC9256, ATCC9226, and ATCC9950.

37. A method for producing a protein encoded by a heterologous gene or a gene isolated from *Candida utilis,* comprising the steps of culturing the *C. utilis* transformant of claim 19 and isolating and purifying the expression product of the gene from the culture.

38. A method for producing a single-chain monellin comprising the steps of culturing the *Candida utilis* transformant of claim 34 and isolating and purifying the single-chain monellin from the culture.

39. A method for producing an amylase comprising the steps of culturing the *Candida utilis* transformant of claim 35, isolating and purifying the amylase from the culture.

40. The method of claim 38, which further comprises the step of heating cell extract proteins to denature and precipitate undesirable proteins derived from the host.

41. The method of claim 40, wherein the heating step is carried out at 50° C. to 70° C.

42. The method of claim 40, which further comprises the step of treating cell extract proteins with an acid to denature and precipitate undesirable proteins derived from the host.

43. The method of claim 42, wherein the acid treatment is carried out at pH 4 to pH 5.

* * * * *

UNITED STATES PATENT AND TRADEMARK OFFICE
CERTIFICATE OF CORRECTION

PATENT NO.   : 6,610,514 B2
DATED        : August 26, 2003
INVENTOR(S)  : Keiji Kondo and Yutaka Miura It is certified that error appears in the above-identified patent and that said Letters Patent is hereby corrected as shown below:

<u>Title page,</u>
Item [62], Related U.S. Application Data, "6,284,536" should read -- 6,284,534 --.

<u>Column 1,</u>
Lines 1 and 2, should read -- U.S. Pat. No. 6,284,534 --.

Signed and Sealed this

Fourth Day of May, 2004

JON W. DUDAS
*Acting Director of the United States Patent and Trademark Office*